(12) United States Patent
Farb et al.

(10) Patent No.: US 6,623,933 B1
(45) Date of Patent: Sep. 23, 2003

(54) METHODS FOR IDENTIFYING A SUBUNIT SPECIFIC MODULATOR OF N-METHYL-D-ASPARATE RECEPTOR

(75) Inventors: David H. Farb, Cambridge, MA (US); Nader Yaghoubi, Boston, MA (US); Shelley Russek, Cambridge, MA (US); Ming-Kuei Jang, Dedham, MA (US); Terrell T. Gibbs, Jamaica Plain, MA (US)

(73) Assignee: Trustees of Boston University, Boston, MA (US)

( * ) Notice: Subject to any disclaimer, the term of this patent is extended or adjusted under 35 U.S.C. 154(b) by 0 days.

(21) Appl. No.: 09/652,345

(22) Filed: Aug. 31, 2000

Related U.S. Application Data

(60) Provisional application No. 60/151,802, filed on Aug. 31, 1999.

(51) Int. Cl.⁷ ...................... G01N 33/53; G01N 33/567; C12Q 1/68; C07K 14/00
(52) U.S. Cl. ........................... 435/7.1; 435/6; 435/7.21; 530/350
(58) Field of Search ........................... 435/7.1, 6, 7.21; 530/350

(56) References Cited

U.S. PATENT DOCUMENTS 5,849,895 A * 12/1998 Daggett et al. ............ 536/23.5
5,888,996 A    3/1999 Farb
6,083,941 A    7/2000 Farb

OTHER PUBLICATIONS

Durand et al., Proc. Natl. Acad. Sci. USA 89:9359–9363 (1992).*
Durand et al., Proc. Natl. Acad. Sci. USA 90: 6731–6735 (1993).*
Williams et al., Mol. Pharmacol. 45 (5):803–809 (1994).*
Yaghoubi et al., Brain Res. 803:153–160 (1998).*
Traynelis et al, J. Neurosci. 18(16):6163–6175 (1998).*
Masuko et al. Mol. Pharmacol. 55:957–969 (Jun., 1999).*
Nakanishi et al., "Alternative splicing generates functionally distinct N–methyl–D–aspartate receptors", Proc. Natl.. Acad. Sci. USA., Sep. 1992, vol. 89, pp. 8552–8556.

Irwin et al., *Neuro. Letters 141*: 30–34 (1992).
Laurie and Seeburg, *Euro. J. of Pharm.* 268: 335–345 (1994).
McBain and Mayer, *Physio. Reviews* 74: 723–760 (1994).
Farb and Gibbs, Steroids as modulators of amino acid receptor function, in: T.W. Stone (Ed.), CNS Transmitters and Neuromodulators: Neuroactive Steroids, CRC Press, New York, 1996, pp. 23–36.
Irwin et al., *J. Pharmacol. Exp. Ther.* 271: 677–682 (1994).
Park–Chung et al., *Mol. Pharmacol.* 46: 146–150 (1994).
Park–Chung et al., *Mol. Pharmacol.* 52: 1113–1123 (1997).
Wu et al., *Mol. Pharmacol.* 40: 333–336 (1991).
Wisden and Seeburg, *J. Neurosci.* 13: 3582–3598 (1993).
Anson et al., *J. Neurosci.* 18: 581–589 (1998).
Wafford et al., *Mol. Pharmacol.* 47: 374–380 (1995).
Weaver et al., *Brain Res.* 761: 338–341 (1997).
Weaver et al., *Proc. Natl. Acad. Sci. USA* 94: 10450–10454 (1997).
Irwin et al., Neuroscience Letters 141: 30–34 (1992).
Laurie et al., European Journal of Pharmacology 268: 335–345 (1994).
McBain, C. J. and Mayer, M. L. Physiological Reviews 74: 723–760 (1994).

* cited by examiner

*Primary Examiner*—Yvonne Eyler
*Assistant Examiner*—Ruixiang Li
(74) *Attorney, Agent, or Firm*—Fish & Richardson PC

(57) ABSTRACT

Disclosed is a method for identifying a subunit specific modulator of the N-methyl-D-aspartate (NMDA) receptor. The method involves providing a plurality of NMDA receptors which differ in their subunit identity. The receptors are contacted with a neurotransmitter recognition site ligand in the presence and absence of a candidate modulator. Receptor activity is then assayed, with an increase or decrease in activity in at least one, but not all members of the plurality of NMDA receptors, in the presence but not the absence of a candidate modulator, being an indication that the candidate modulator is a subunit specific modulator. The subunit identity of the subset of the NMDA receptors to determine the subunit specificity of the candidate modulator. Various combinations of NMDA receptor subunits are provided.

10 Claims, 45 Drawing Sheets

```
RXR-α   ILE.AELAVEPKTETYVEANMGL.NPSSPNDPVTNIC.QAADKQLFTL
PAR     LCQLGKYTTNSSADHRVQLDLGLWDKFS..ELATK.C..II.K....I
PR      IN.LLM.SIEPDV.IYAGHD.N.TKPDTSSSLLTSL.NQLGERQLLSV
GCR     VS.LLE.VIEPEV.LYAGYD.S.SVPDSTWRIMTTL.NMLGGRQVIAA
ER         SALLD.A.EPPI.LYSEYD.P.TRPFSEASMMGLLTN.LADRELVHM
NR1₀₁₁  IILLVSDDHEGRAA.QKRLETLLEERESKAEKVLQF.DP.GTKNVTAL   207
                        Δ           Δ            Δ

RXR-α   V.EWAKRIPH.FSELPL..DDQVILLRAGWNELLIA..SFSHR.SIA
PAR     V.EFAKRLPG.FTGLSI..ADQITLLKAACLDILML..RICTR.YTP
PR      V.KWSKSLPG.FRNLHI..DDQITLIQYSWM.SLMV.FGLGWR.SYK
GCR     V.KWAKAIPG.FRNLHL..DDQMTLLQYSWM.FLMA.FALGWR.SYR
ER      I.NWAKRVPG.FVDLTL..HDQVHLLECAWLEILMI..GLVWR.SME
NR1₀₁₁  LME.ARELEARVIILSASEDDAATVYRAAAM.LNMTGSGYVWLVGER    252
                          Δ                    Δ

RXR-α   VKDG.IL.LATG.LH.VHR.N          (SEQ ID NO:1)
PAR     EQDT.MT.FSDG.LT.LNR            (SEQ ID NO:2)
PR      HVSGQMLYFAPD.LI.L...N          (SEQ ID NO:3)
GCR     QSSANLLCFAPD.LI.I...N          (SEQ ID NO:4)
ER      H.PGKLL.FAPN.LL.LDR.N          (SEQ ID NO:5)
NR1₀₁₁  EISGNALRYAPDGIIGLQLIN    273   (SEQ ID NO:6)
```

FIG. 23

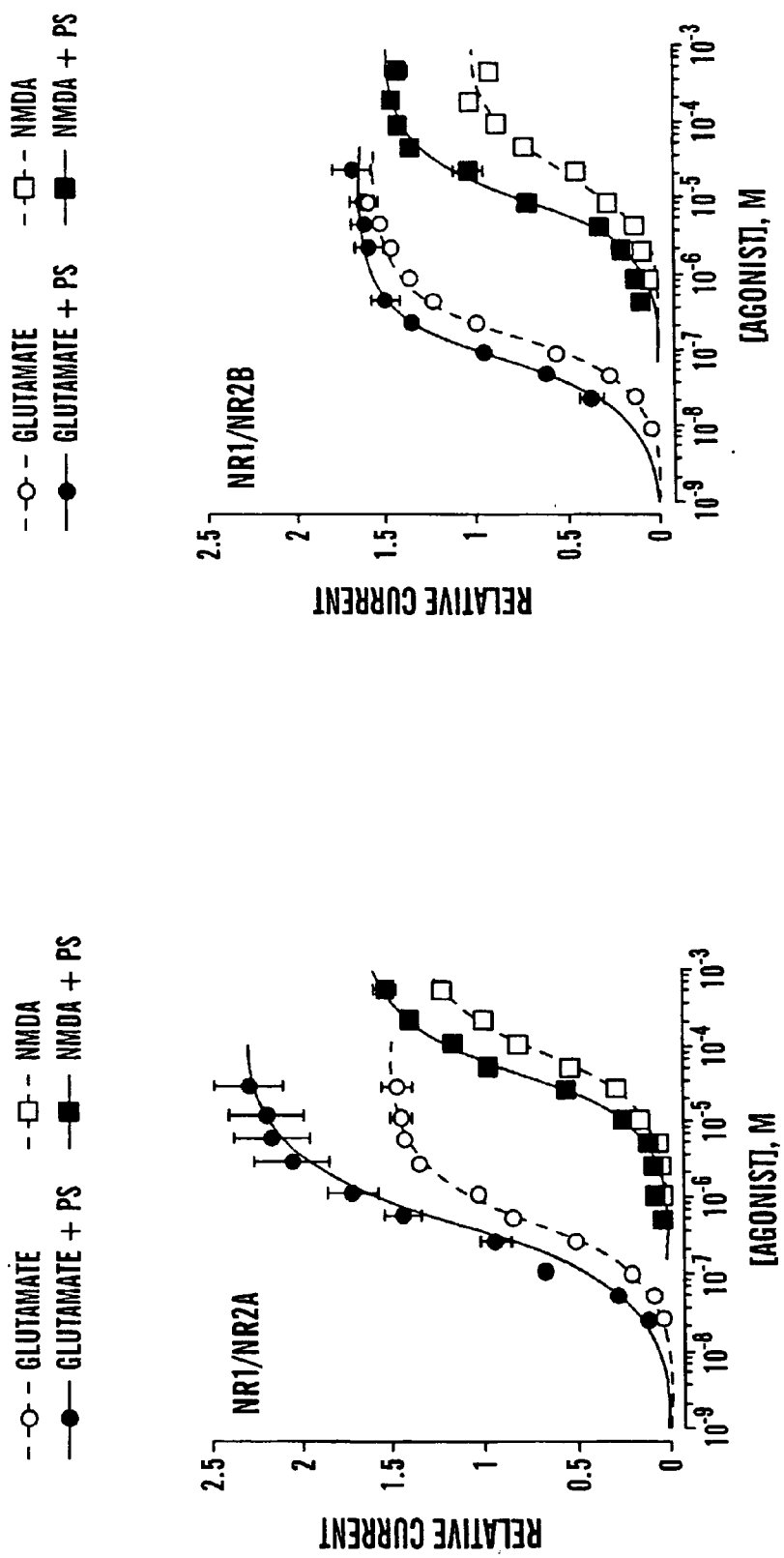

METHODS FOR IDENTIFYING A SUBUNIT SPECIFIC MODULATOR OF N-METHYL-D-ASPARATE RECEPTOR

RELATED APPLICATIONS

The present application claims priority to U.S. Provisional Application No. 60/151,802, filed Aug. 31, 1999.

This invention was made with Government Support under Contract Number MH-49469 awarded by the National Institutes of Health. The Government has certain rights in the invention.

BACKGROUND OF THE INVENTION

The NMDA receptor subtype is known to have a fundamentally important role in CNS function. Ongoing work from many laboratories has established the involvement of NMDA receptors in multiple aspects of brain development, synaptic plasticity associated with long-term potentiation, and pathology related to glutamate-mediated excitotoxicity. In particular, neuropathological mechanisms mediated by NMDA receptors have recently been implicated in neurological disorders including ischemic stroke, kindling epileptogenesis, and schizophrenia.

The NMDA receptor is composed of two different types of subunits, the NR1 and the NR2. The NR1 subunit is ubiquitously expressed throughout the CNS, particularly in the cerebral cortex, hippocampus, and olfactory bulb. While homomeric NMDA receptors composed of NR1 subunits are activated by NMDA, heteromeric receptors composed of both NR1 and NR2 subunits exhibit greater responses to NMDA.

Alternative splicing of three exons, α, β, and γ (also referred to in the art as N1, C1, and C2, respectively) generates eight isoforms of the mRNA encoding the NR1 protein. A schematic of the NR1 splice variants is shown in FIG. 1 in which the presence or absence of any of the three alternatively spliced exons is designated by a subscript within the name. FIG. 2 lists the eight splice variants and the alternatively spliced exons present in each variant. Exons, α, β, and γ, code for 21, 37, and 38 amino acid sequences, respectively. The α exon, which corresponds to exon 5, is located in the extracellular amino-terminal portion of the receptor, whereas the β and γ exons, corresponding to exons 21 and 22, respectively, are located at the carboxy-terminal domain. Interestingly, a stop codon is contained within the γ exon. Its removal by alternative splicing leads to the inclusion of a new 22 amino acid sequence.

The inclusion of any one or a combination of the three exons imparts differential pharmacological properties to the NMDA receptor. For example, inclusion of the N1 exon leads to a decrease in agonist affinity, but an increase in current amplitude. A number of consensus PKC phosphorylation sites have been identified within the C1 exon; however, a functional role for these sites has not been fully elucidated. Other differences imparted by alternative splicing include sensitivity to potentiation by spermine, $Zn^{2+}$, and activators of PKC.

An examination of the levels of NR1 splice variants in the developing rat brain has revealed regional differences in the pattern of expression. This divergent pattern in the expression of the NR1 splice variants may provide a degree of functional diversity in NMDA receptor function that underlies the regional heterogeneity in certain NMDA receptor-dependent processes, including synaptic consolidation, potentiation, and plasticity.

The four subtypes of the NR2 subunit: NR2A, NR2B, NR2C, and NR2D were identified through molecular cloning studies. Studies indicate that the inclusion of different NR2 subtypes within the heteromeric NMDA receptor alters the pharmacological properties of NMDA receptor function providing another level of functional diversity to the receptor. For example, differences in $Ca^{2+}$ permeability, sensitivity to $Mg^{2+}$ block, glycine potentiation, and offset kinetics can be attributed to the presence of specific NR2 subunits in the heteromeric receptor.

The NR2 subunits have about 50% sequence homology between members and have approximately 15% sequence homology with the NR1 subunits. They are incapable of forming functional NMDA-activated channels following homomeric expression, but rather serve to potentiate the NMDA response and modify pharmacological properties when coexpressed with NR1 subunits. Recent work has shown that the NR2A and NR2B subunits are tyrosine-phosphorylated, whereas the NR1 subunits are not.

In situ hybridization experiments have shown that the NR2 subunits exhibit a region-specific and temporal-specific pattern of expression. For example, the NR2B subunit is mainly expressed in the rat forebrain, whereas the NR2C subunit is found predominantly in the cerebellum. Differences in the expression of the NR2 subunits may be responsible for imparting functional diversity to NMDA receptor function from one cell type to the next.

SUMMARY OF THE INVENTION

The present invention relates to a method for identifying a subunit specific modulator of the N-methyl-D-aspartate (NMDA) receptor. The method involves providing a plurality of NMDA receptors which differ in their subunit identity. The receptors are contacted with a neurotransmitter recognition site ligand in the presence and absence of a candidate modulator. Receptor activity is then assayed, with an increase or decrease in activity in at least one, but not all members of the plurality of NMDA receptors, in the presence but not the absence of a candidate modulator, being an indication that the candidate modulator is a subunit specific modulator. The subunit identity of the subset of the NMDA receptors to determine the subunit specificity of the candidate modulator. Various combinations of NMDA receptor subunits are provided.

BRIEF DESCRIPTION OF THE DRAWINGS

FIG. 2 is a compilation of graphical representations of data which indicate that pregnenolone sulfate (PS) inhibits α-amino-3-hydroxy-5-methyl4-isoxazolepropionate (AMPA) and kainate receptor function.

FIG. 23 is a multiple sequence alignment of the ligand binding domains of the human retinoic acid receptor γ (RAR), the human retinoid X receptor α (RXR-α), the human progesterone receptor (PR), the human glucocorticoid receptor (GR), the human estrogen receptor (ER) and the NMDA receptor NR1 subunit ($NR1_{011}$). Conserved identical residues are bold and underlined and similar residues are bold. The triangles (Δ) under the $NR1_{011}$ sequence indicate the five mutation sites in the Penta-mutant. The five mutation sites are R182A, K193A, K202A, R233A, and R252A.

DETAILED DESCRIPTION OF THE INVENTION

Figure 1:
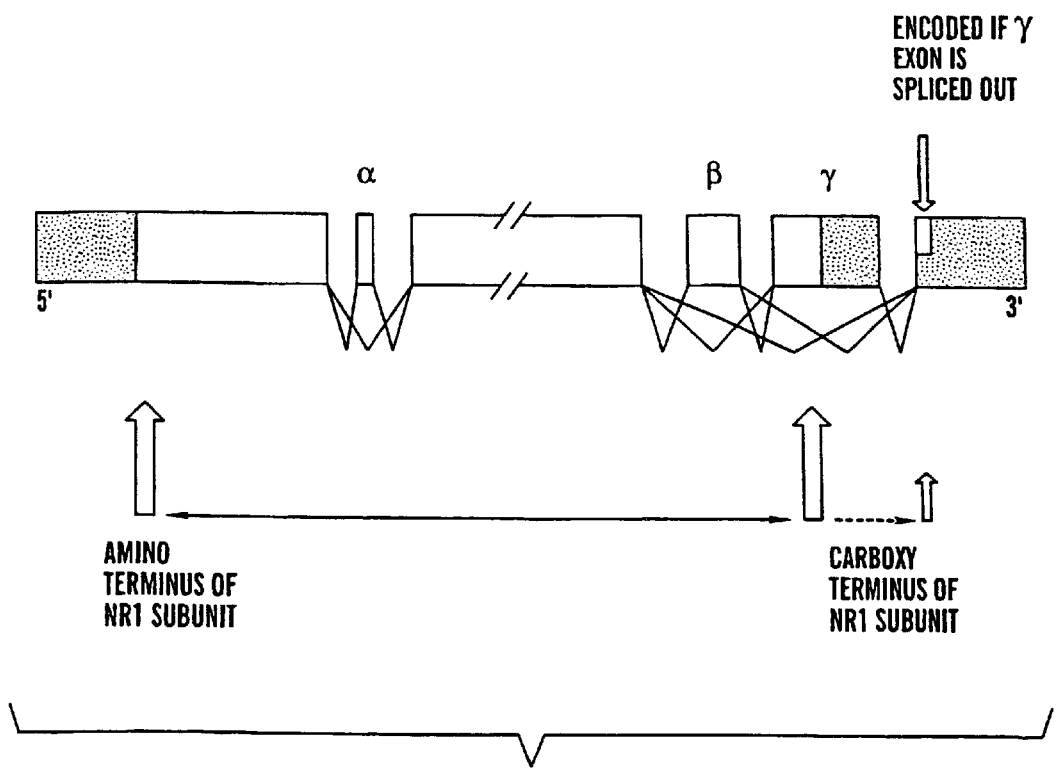
FIG. 1 is a schematic of the proposed structure of the alternative splice variants of the NMDAR1 (NR1) mRNA.

Aspects of the present invention are based on the identification of steroid molecules which exhibit selectivity with respect to NMDA receptor subunit composition. This observation indicates that it is possible to develop or identify drugs (steroid based as well as non-steroid based) that selectively target specific NMDA receptor subtypes to modulate neurotransmitter recognition site ligands. One aspect of the present invention is a method for identifying a subunit specific modulator of the NMDA receptor. This is accomplished through use of a plurality of NMDA receptors which differ in their subunit identity (NR1 and NR2 subunits). The plurality of NMDA receptors is then contacted with a neurotransmitter site agonist (e.g., L-glutamate or NMDA) in the presence and absence of a candidate modulator. Each NMDA receptor is then assayed for receptor activity produced by the neurotransmitter site agonist, in the presence and absence of the candidate modulator. An increase or decrease in activity of the receptor in the presence of the candidate modulator, as compared to the respective activity in the absence of the candidate modulator, indicates modulatory activity on the receptor. Such an increase or decrease in activity in at least one, but not all members of the, plurality of NMDA receptors, is an indication that the candidate modulator is a subunit specific modulator.

The subunit specificity of the candidate modulator is identified by comparing the subunit identity of the subset of NMDA receptors which are subject to modulation by the candidate modulator. The candidate modulator is specific for the subunits, or domains of the subunits, which are common to this subset of receptors and absent or non-functional in the remaining receptors of the plurality. One of skill in the art will readily recognize that the potential subunit specificity of modulators identified by this method is vast, and is only limited by the combination of subunits utilized in the method itself.

Subunit specificity may be for one or more particular isoforms, chimeras or mutants of either the NR1 or NR2 subunit, that is to say it may be independent of one of the subunits. Alternatively, the modulator may be specific for a particular combination of the two subunits.

A modulator of the NMDA receptor is defined herein as binding at a modulatory site, and may be either a positive modulator or a negative modulator, or a null modulator. A positive modulator enhances agonist activity. It has been shown that positive and negative modulators of the NMDA receptor act through distinct sites. Pregnenolone sulfate is a known positive modulator of the NMDA receptor. This is often referred to in the art as a modulatory site agonist. A negative modulator inhibits agonist activity. Examples of known negative modulators of the NMDA receptor are 17β-estradiol and pregnanolone hemisuccinate (3α5βHS), also referred to in the art as inverse agonists. Negative modulators have been shown to be neuroprotective from otherwise lethal exposure to NMDA, whereas positive modulators enhance excitotoxicity. A null modulator has no intrinsic activity in and of itself other than to inhibit the action of a positive and/or negative modulator by competitively binding at the modulatory site.

A neurotransmitter recognition site ligand as the term is used herein refers to a ligand (agonist or antagonist) which binds at the neurotransmitter recognition site. Examples of agonists are NMDA, L-glutamate and glycine.

An increase or decrease in receptor activity in the presence of the candidate modulator, as compared to activity in the absence of the candidate modulator, is identified by a reproducible, statistically significant change in receptor activity in response to ligand (agonist or antagonist). Current methodology is sensitive to the detection of approximately a 5% or greater difference in receptor activity, with an 8% difference or greater being a strong indication of modulatory activity. Preferably, a 10% or greater difference in receptor activity in the presence of candidate modulator is used to identify modulator activity. These sensitivity limitations also apply to identifying a subunit specific affect of a modulator, in that down to a 5% difference in receptor activity can be detected and used to identify subunit specific modulation. However, the larger the discrepancy between modulatory activity on one receptor versus another receptor, the more useful the subunit specific modulator will prove in therapeutic applications.

Subunit identity, as used herein, refers to the specific subunit components NR1 and NR2 used to generate the NMDA receptor. This term encompasses both natural and recombinantly produced subunits and receptors. Preferably, the NMDA receptors used in the method are produced recombinantly as this allows for use of a greater diversity of receptor subunit identities. There are eight known natural isoforms of the NR1 subunit ($NR1_{000}$, $NR1_{001}$, $NR1_{010}$, $NR1_{011}$, $NR1_{100}$, $NR1_{101}$, $NR1_{110}$, and $NR1_{111}$), and four known natural isoforms of the NR2 subunit (NR2A, NR2B, NR2C, and NR2D). Additional isoforms of each subunit will likely be identified in future research, and their use is also encompassed by the present invention. In addition to these natural isoforms, mutant isoforms (e.g., point mutant, deletion mutant, etc.) and also chimeric isoforms are suitable for use in the method. Mutation or other sequence manipulation of an isoform for use in the method should not result in loss of detectable function/activity of the NMDA receptor which is produced.

The receptor subunits used in the experiments detailed below in the Exemplification section were of human origin. The present invention is not however limited to the use of human receptors. Homologous subunits or subunit regions of homologous receptors from other species are also suitable for use in the present invention.

Experiments detailed in the Exemplification section below have identified several useful sites for point mutation of NR1 subunits which contain an α exon encoded protein domain. These sites correspond to residues 182, 193, 202, 233, and 252 of human $NR1_{011}$. One or more of these residues, in any combination, may be mutated in the NR1 subunit to produce the NMDA receptor for use in the present invention. Preferred point mutations are R182A, K193A, K202A, R233A, and R252A. The nature of the specific substituted amino acid may have an effect on mutant function. As such, substitution of any positively charged amino acid into these positions is expected to produce a mutant having a phenotype similar to the penta-mutant characterized in Example 5. However, the location of the mutated amino acid is also thought to have particular relevance. Therefore, a number of different amino acid substitutions at one or more of these sites is expected to produce a mutant with a phenotype reminiscent of that of the penta-mutant of Example 5.

Chimeric NR1 or NR2 subunits used in the present invention preferably retain intact protein domains. Such protein domains are usually contained within individual exons, often being delimited by those exons. The α exon of the NR1 subunit has been identified as encoding a protein domain which is involved in subunit specific modulation of the receptor. It is likely that domains encoded by other exons will also be useful in identifying additional subunit specific modulators which recognize and/or function through those specific domains. Prime candidates are the other two alternatively spliced exons, β and γ, of the NR1 subunit. Some domains of the NR2 subunits identified as useful in the present invention correspond to residues 534–870 of human NR2B, and also residues 548–892 of human NR2D. In addition, the domain which corresponds to residues 703–870 of human NR2B has been identified as necessary and sufficient for stimulation of the receptor by neurosteroids. This domain confers neurosteroid stimulation to the NR2B/NR2D chimera, whereas wild type NR2D is inhibited by the same neurosteroids. The identification of these domains represent the beginnings of a growing understanding of the domains involved in neurosteroid modulation. The use of chimeras made of different combinations of subunit domains in the present invention will identify subunit specific modulators which function through as yet unidentified functional protein domains of the respective subunits.

The specific combinations of NR1 and NR2 subunits used in the method dictates the types of subunit specific modulator which is identified. For instance, it may be useful to vary the identify of one subunit, either NR1 or NR2, in combination with a fixed identity of the other subunit. Any particular combination of the NR1 and NR2 subunits described herein is appropriate for use in the present invention.

Assaying for receptor activity can be by any method known in the art. Preferred assay systems allow expression and utilization of recombinant receptors. A preferred assay system is an *oocyte* expression system.

Candidate modulators may be obtained from a variety of sources. They may be naturally occurring molecules, or alternatively synthetic molecules. Although the modulators provided as examples in the Exemplification section below are steroid based molecules, a subunit specific modulator may also be a non-steroid based molecule. Candidate modulators may be known neuromodulators, or may be otherwise derived from known neuromodulators. In one embodiment, candidate modulators are obtained from a library of small molecules, either natural or synthetic (e.g., produced by rational drug design or randomized combination).

Because the different NMDA receptor subunits are differentially distributed throughout the nervous system, therapeutic effects can be achieved through subunit specific intervention, accomplished by targeting a specific receptor, made up of specific subunits, with a subunit specific modulator identified by the above described method. Such targeting has use in therapeutic intervention in neurological disorders which are linked to glutamate receptor function. For example, receptors consisting of specific subunits can be targeted to inhibit the neurodegeneration which results from cerebral ischemia. Specific inhibition of AMPA/kainate receptor function can also be beneficial in the treatment of ischemic stroke. The neuroactive steroid class of glutamate receptor modulatory agents may also prove to be neuroprotective in brain ischemia.

Several aspects of the present invention are based upon the identification of specific subunits involved in the modulation of the effect of pregnenolone sulfate on ligand gated ion channel activity. Excitatory neurotransmission in the vertebrate central nervous system is mediated primarily by ionotropic glutamate receptors. A variety of endogenous and synthetic steroids have been found to modulate the function of neuronal glutamate receptors (Farb and Gibbs, Steroids as modulators of amino acid receptor function, in: T. W. Stone (Ed.), CNS Transmitters and Neuromodulators: Neuroactive Steroids, CRC Press, New York, 1996, pp. 23–36; Irwin et al., *J. Pharmacol. Exp. Ther.* 271: 677–682 (1994); Park-Chung et al., *Mol. Pharmacol.* 46: 146–150 (1994); Park-Chung et al., *Mol. Pharmacol.* 52: 1113–1123 (1997); Wu et al., *Mol. Pharmacol.* 40: 333–336 (1991)). Pregnenolone sulfate (PS) is an abundant neurosteroid that can potentiate or inhibit ligand gated ion channel activity and thereby alter neuronal excitability. Whereas PS has previously been shown to inhibit Kainate and AMPA responses while potentiating NMDA responses, the dependence of modulation on receptor subunit composition was previously undetermined. To that end, experiments detailed below in Example 1 of the Exemplification section have characterized the effect of PS on recombinant kainate (GluR6), AMPA (GluR1 or GluR3), and NMDA (NR1$_{100}$+NR2A) receptors electrophysiologically with respect to efficacy and potency of modulation. PS is shown to reduce the efficacy of kainate without affecting its potency, when given to *Xenopus oocytes* expressing GluR1, GluR3 or GluR6 receptors. This indicates a non-competitive mechanism of action on these specific receptors. Conversely, PS is shown to enhance the efficacy of NMDA without affecting its potency when given to *oocytes* expressing NR1$_{100}$+NR2A subunits. The modulatory efficacy, but not the potency, of PS is increased two-fold by co-injection of NR1$_{100}$+NR2A cRNAs as compared with NR1$_{100}$ cRNA alone. However, there is little or no effect of the NR2A subunit on efficacy or potency of pregnanolone (or epipregnanolone) sulfate as an inhibitor of the NMDA response. This indicates that the NR2A subunit controls the efficacy of neurosteroid enhancement, but not inhibition, which is consistent with previous findings that potentiating and inhibitory steroids act at distinct sites on the NMDA receptor. These findings represent a first step towards understanding the role of subunit composition in determining neurosteroid modulation of ionotropic glutamate receptor function.

Results presented in Example 1 of the Exemplification section below indicate that selective modulators can be developed which specifically target particular AMPA or kainate receptor subtypes. Only negative steroid modulation of recombinant AMPA and kainate receptors was observed in the experiments described in Example 1 below. At the GluR1, GluR3 and GluR6 receptor subtypes, pregnenolone sulfate reduces the maximum kainate-induced currents without altering the kainate EC50, consistent with a noncompetitive mechanism of inhibition. At GluR1 and GluR3 receptors, 100 μM pregnenolone sulfate produces over 70% inhibition of the response to kainate. However, the same concentration of pregnenolone sulfate inhibited GluR6 receptor response to kainate by only 42%. Notably, the concentration response curve for inhibition of GluR6 receptors by pregnenolone sulfate is more shallow than for GluR1 or GluR3 receptors, which indicates that pregnenolone sulfate inhibits kainate and AMPA receptors by different mechanisms. Such specific modulators are useful in determining the receptor composition of specific cell populations, as well as probing the functional roles of AMPA and kainate receptors in situ (Wisden and Seeburg, *J. Neurosci.* 13: 3582–3598 (1993)).

In order to investigate if the presence of different exons in the NR1 subunit affects NMDA receptor modulation by neurosteroids, an *oocyte* expression system was employed to electrophysiologically assess the neurosteroid effect on NMDA receptors composed of different NR1 subunit isoforms. Experiments detailed in Example 3 indicate NR1 subunit dependent effects of neurosteroid modulation on the NMDA receptor. Of note, the presence of the N-terminal 21 amino acid insert in the NR1 subunit changes the efficacy of neurosteroid positive modulator PS without altering the effect of neurosteroid negative modulator 3α5βS. The fact that uncharged analog of PS, pregnenolone, has little effect on NMDA receptors suggests that some charged amino acids mediate the potentiating effect. The fining of modulation of PS effect by the presence of the n-terminal insert is consistent with this hypothesis because the charged amino acids constitute almost 43% of total of 21 amino acids in the insert. Moreover, empirical analysis of the surface probabilities of amino acids constituting N-terminal insert in the NR1 subunit suggests that most of amino acids in the insert are located on the surface of the protein, that position them as good candidates for direct interaction with charged ions, including negatively charged molecules of pregnenalone sulfate. Inhibitory effect of 3α5βS turned out to be similar for different isoforms of NR1 subunit, suggesting that inhibitory steroids do not interact with the N-terminal insert. This observation is consistent with the finding that stimulatory and inhibitory sulfated neurosteroids have distinct sites of action on NMDA. receptor.

The effect of both potentiating and inhibitory steroids on NMDA receptors was observed at all agonist concentration tested. Furthermore, the potency of agonists L-glutamate, NMDA, and glycine was not changed by neurosteroids indicating that the steroids do not interact with agonist binding sites.

The observed dependence of potentiating effect of steroids on the level of NMDA receptor expression in the membrane of *oocytes* suggests that when too many receptors are expressed in the membrane there are not enough molecules of steroid around the receptor to interact with the receptor. Without being bound by theory, it may be that in order to interact with the receptor the molecules of pregnenolone sulfate must be incorporated into the membrane first, and then, they could approach the receptor's binding site. The molecular structure of pregnenolone sulfate fits this hypothesis quite well. The molecule of pregnenolone sulfate has hydrophobic part that could be incorporated into the membrane, while charged sulfate part remains in aqueous surrounding. According to this hypothesis the molecule of NR1 protein folded so that the N-terminal insert is positioned close to the membrane surface.

The results detailed in Example 6 are the first to indicate that the modulatory effect of PS is contingent upon the NR2 subunit composition of the NMDA receptor, and that PS inhibits, rather than enhances, the function of NR1/NR2C and NR1/NR2D receptors. The finding that potentiation of the NMDA receptor by PS is dependent upon the presence of the NR2A or NR2B subunit indicates that the steroid binding site responsible for potentiation by PS is partially or entirely located on these subunits. Mutagenesis studies suggest that the glutamate/NMDA binding site resides on the NR2 subunit (Anson et al., *J. Neurosci.* 18: 581–589 (1998)), while the glycine site resides on NR1 (Wafford et al., *Mol. Pharmacol.* 47: 374–380 (1995)), so the NMDA responses observed in *oocytes* injected only with NR1 subunits likely reflect coassembly of NR1 with an endogenous NR2A or NR2B-like subunit (Soloviev and Barnard, *J. Mol. Biol.* 273: 14–18 (1997)).

To investigate the structural requirements for steroid inhibition of NMDA-induced neuronal death, 3α5β and stereoisomers of 3α5βS were assayed for activity, as were several related synthetic pregnane steroids. The results detailed in Example 2 indicate that stereochemistry at the A-B ring junction is an important determinant of the activity of pregnanes with a negatively-charged group at C3. Since positive and negative modulation by steroids are mediated by distinct sites, the more planar ring structure of the pregn-5-enes and C5α pregnanes is thought to improve the fit of the steroid molecule to a potentiating modulatory site and/or impairs its fit to an inhibitory modulatory site. Such structural information is useful in the identification or rational drug design of additional modulators. Molecules which exhibit the appropriate molecular structure can be synthesized and/or screened for the corresponding activity with the appropriate isoforms of the NR1 and NR2 subunits.

Results also indicate that the presence of a negative charge adjacent to the C3 position is necessary for the negative modulatory effect of pregnane steroid derivatives on NMDA receptor function. There is limited tolerance for the geometry of the charged group at C3, since a range of lengths (from the relatively short hemioxalate group to the five-carbon hemiglutarate group) is able to confer inhibitory activity. The effects of the pregnane steroids on NMDA responses of *Xenopus oocytes* expressing $NR1_{100}+NR2A$ subunits are in general agreement with results from hippocampal neurons in culture. The development of a full negative charge may not be absolutely necessary for inhibition of the NMDA receptor by steroids, as 3α5βF produces a modest but statistically significant inhibition of the NMDA-induced current. This is consistent with the observation that 17β-estradiol, which has a hydroxyl group at C3, inhibits the NMDA-induced current and $Ca^{2+}$ accumulation, and is neuroprotective against NMDA-induced neuronal death (Weaver, et al., *Brain Res* 761: 338–341 (1997)). A strongly electronegative center attached to C3 is therefore sufficient to support some degree of steroid inhibition of the NMDA receptor. The lack of significant neuroprotection or inhibition of $Ca^{2+}$ accumulation with 3α5βF is thought to reflect eitherthe difficulty of detecting the effect of such a weak inhibitor, or a difference in the interaction of 3α5βF with native NMDA receptors of hippocampal neurons, as compared to the $NR1_{100}$:NR2A subtype used for the electrophysiological studies. These latter results suggest that a negatively charged group at C3 enhances the neuroprotective properties of the pregnane steroid derivatives.

These findings, taken in combination with previous findings reported in U.S. Pat. Nos. 5,888,996, and 6,083,941, the contents of which are herein incorporated by reference, indicate a wider range of compounds which function in the inhibition of NMDA receptor activation, than was previously appreciated. Another aspect of the present invention is the use of a compound represented by the structural formula:

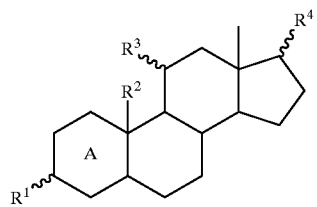

wherein ring A has 0–3 double bonds; $R^1$ is —OH, =O, or a negatively charged group; $R^2$ is —H, —$CH_3$, or is absent when ring A has three double bonds; $R^3$ is —H, OH, =O, or —OR'; $R^1$ is an aliphatic or aromatic group; and $R^4$ is —OH, =O or —$COCH_3$, to inhibit NMDA activity resulting from agonist activation. In one embodiment of the invention, $R^4$ is either hemioxylate, hemisuccinate or hemiglutarate. In preferred embodiments, the compound is either pregnanolone hemioxylate, pregnanolone hemisuccinate, or pregnanolone hemiglutarate.

The ability of compounds with the above structural formula to inhibit agonist activation of the NMDA receptor can be therapeutically applied to inhibit NMDA receptor mediated ion-channel activity in an individual in need thereof by administering an effective amount of the compound to the individual. Effective amounts range from about 1 to about 500 μM, with a preferred range being from about 50 to about 250 μM. Such administration can be used to inhibit the toxic effects associated with activation of the NMDA receptor in neurons of the individual. Another useful application of this method of inhibiting agonist activation of the NMDA receptor is in reducing neuronal cell death resulting from L-glutamate activation of the NMDA receptor. This also is achieved by administration of the compound to an individual as described above. Additional diseases which can be treated by said administration of the compound are neuropathic pain, drug withdrawal/dependency, epilepsy, glaucoma, chronic neurodegenerative diseases, amyotrophic lateral sclerosis, anxiety disorders, brain cell death, ischaemia, stroke, and trauma in an individual when said disease results from NMDA induced NMDA receptor activation. Administration of the compound can also be used to inhibit the excitatory or L-glutamate-mediated synaptic activity in an individual in need thereof.

Results presented in Example 2 which demonstrate that modulation by steroids of NMDA-induced $Ca^{2+}$ uptake is correlated with modulation of NMDA-induced neuronal death, indicate that this rapid functional assay can be usefully employed to identify steroids with neuroprotective activity.

Another aspect of the present invention relates to a method for rationally designing steroid-based therapeutics for the treatment of stroke and disorders arising from the overactivation of the NMDA receptor. The finding that a variety of negatively-charged carboxylic acid esters can substitute for the sulfate ester at the C3 position of the above described molecule offers prospects for modifying the steroid nucleus to optimize pharmacological and pharmacokinetic properties. Carboxylic acid derivatives of neuroactive steroids should offer improved penetration into the CNS and reduced susceptibility to hydrolysis by sulfatases. This is supported by the observation that 3α5βHS is effective at inhibiting the neuronal death that results from middle cerebral artery occlusion in rats, a model of stroke (Weaver et al., *Proc Natl Acad Sci USA* 94:10450–10454 (1997)). Based on the present results, carboxylic acid derivatives of the pregn-5-ene steroids are expected to exhibit memory-enhancing effects such as have been described for pregnenolone sulfate (Isaacson et al., *Behav Neural Biol* 61: 170–176 (1994); Flood et al. *Proc Natl Acad Sci USA* 92: 10806–10810 (1995); Vallee et al., *Proc Natl Acad Sci USA* 94: 14865–14870 (1997)).

Exemplification

Figure 2A:
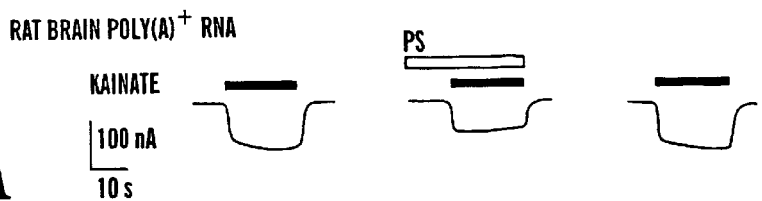
FIGS. 2(A) through 2D are representative traces showing the inhibitory effect of 100 μM PS on kainate-induced currents of *oocytes* injected with (A) rat brain poly(A)+ RNA, (B) GluR1 cRNA, (C) GluR3 cRNA, (D) GluR6 cRNA. The kainate concentration used in (A)–(C) was 100 μM, and in (D) was 10 μM. The solid bar represents the period of kainate (KA) application; the open bar indicates the period of PS exposure.

EXAMPLE 1
Modulation of Recombinant AMPA and Kainate Receptors by PS and Related Steroids In addition to altering currents through NMDA receptors, PS inhibits AMPA- and kainate-induced currents recorded from chick spinal cord neurons (Wu et al., *Mol. Pharmacol.* 40: 333–336 (1991)). Similarly, PS produces a 49±3% (n=4) reduction in kainate-evoked responses from *oocytes* injected with rat brain poly(A)$^+$ RNA (FIG. 2A). The observation that onset of inhibition is rapid (<10 s), strongly suggests a direct interaction between PS and the AMPA/kainate receptor. However, these results cannot exclude the possibility that PS acts indirectly through some other neuronal receptor or transduction system that is co-expressed from rat brain poly(A)$^+$ RNA. Therefore, the ability of steroids to modulate the function of recombinant AMPA and kainate receptors was examined.

Figure 2B:
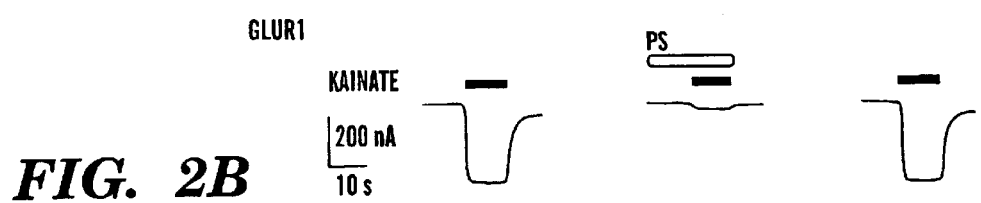
Figure 2C:
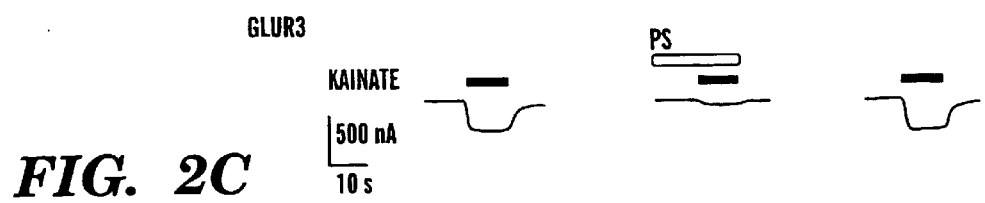
Figure 2D:
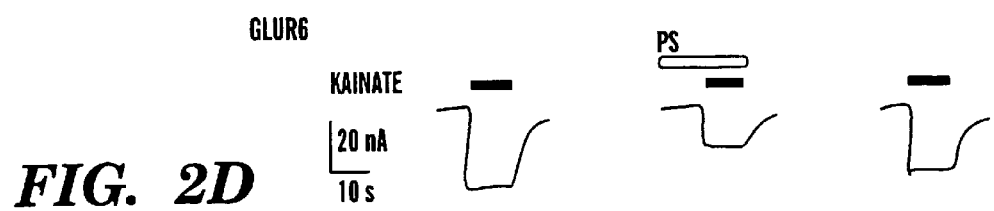
Figure 2E:
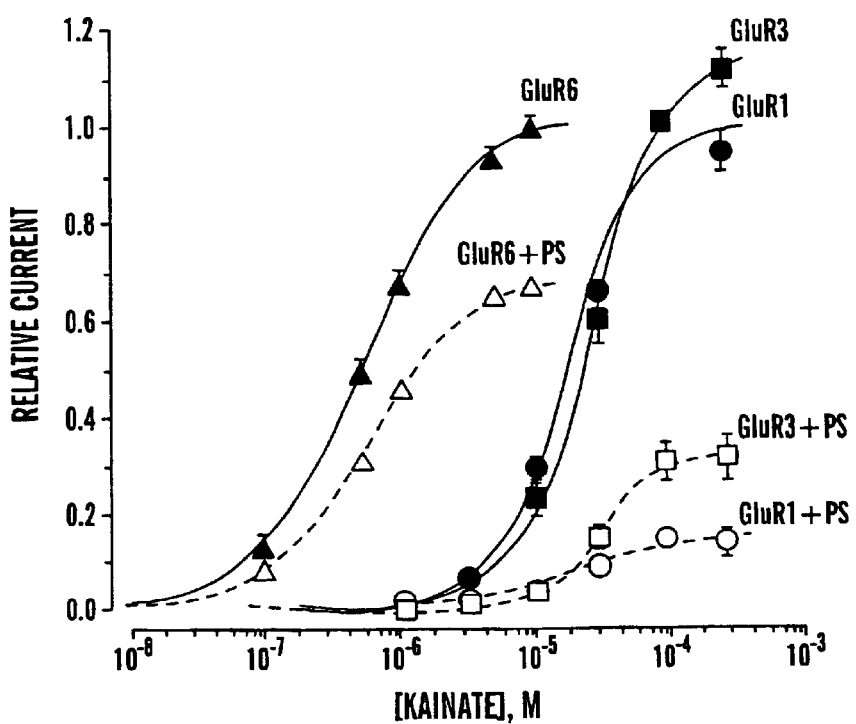
FIG. 2E is a graph of relative current for the indicated Kainate concentration. The administration of PS (open symbols) is seen to decreases maximum kainate responses of GluR1 (●, ○), GluR3 (■, □), and GluR6 (▲, △) receptors. Each data point represents the mean of three experiments. Error bars represent standard error. Smooth curve was determined by non-linear regression using the logistic equation applied to pooled data. Fitted parameters are (GluR1) $I_{max}$=1.0, $EC_{50}$=27 μM, $n_H$=1.54; (GluR1+PS) $I_{max}$=0.17, $EC_{50}$=23 μM, $n_H$=0.9; (GluR3) $I_{max}$=1.15, $EC_{50}$=27 μM, $n_H$=1.44; (GluR3+PS) $I_{max}$=0.33, $EC_{50}$32 μM, $n_H$=1.93; (GluR6) $I_{max}$=1.0, $EC_{50}$=550 nM, $n_H$=1.1; (GluR6+PS) $I_{max}$=0.69, $EC_{50}$=570 nM, $n_H$=1.2.

Injection of GluR1, GluR3, or GluR6 subunit cRNA into *Xenopus oocytes* was sufficient to confer kainate sensitivity (FIG. 2B–D). *Oocytes* injected with GluR6 cRNA responded to lower concentrations of kainate ($EC_{50}$=550 nM, FIG. 2E) than *oocytes* injected with GluR1 or GluR3 cRNA ($EC_{50}$'s 23 μM and 32 μM), as expected from the classification of GluR6 as a kainate receptor subunit and GluR1 and GluR3 as AMPA receptor subunits (Hollmann and Heinemann, *Annu. Rev. Neurosci.* 17: 31–108 (1994)). As with the receptors formed from the expression of rat brain poly(A)$^+$ RNA, recombinant AMPA and kainate receptor responses were inhibited by PS. In each case, PS functioned as a noncompetitive inhibitor, decreasing the maximum kainate-induced current without affecting the $EC_{50}$ (FIG. 2E). At the GluR1 AMPA receptor, PS (100 μM) reduced the kainate $I_{max}$ by 83%, while the kainate $EC_{50}$ was unchanged (18 μM vs. 23 μM with PS). GluR3 AMPA receptor function was also markedly reduced by PS, which reduced the kainate $I_{max}$ by 71% without altering the $EC_{50}$ (27 μM vs. 3.2 μM in the presence of PS). Although the extent of inhibition was less, PS also appeared to act as a noncompetitive inhibitor of GluR6 kainate receptor function, reducing the kainate $I_{max}$ by 33% with no change in $EC_{50}$ (545 nM vs. 567 nM in the absence and presence of PS, respectively).

Figure 2F:
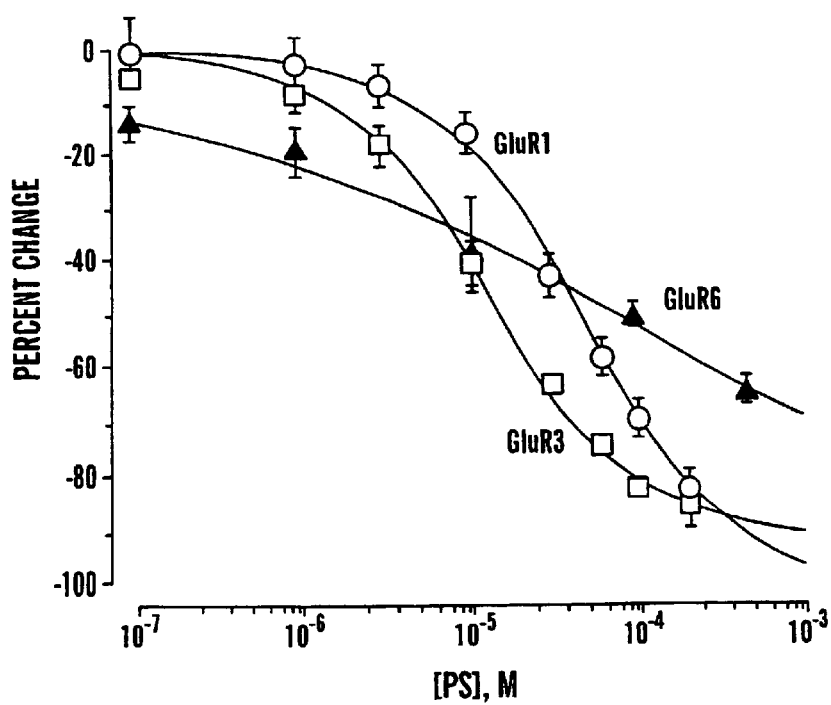
FIG. 2F is a graph of data showing the concentration dependence of PS inhibition of recombinant GluR1 (○), GluR3 (□), and GluR6 (▲) receptors. Results are expressed as percentage change in the peak 100 μM (GluR1 and GluR3) or 10 μM (GluR6) kainate-induced current in the presence of PS. Each data point is the mean of three experiments; error bars indicate S.E.M. For GluR1 and GluR3, smooth curves are derived from fits to the Michaelis-Menten equation, as fits to the logistic equation yielded Hill coefficients close to 1, with no significant improvement in sum of squares (F-test, P>0.05). Fitted parameters are (GluR1) $EC_{50}$=43 μM, $E_{max}$=−99%; (GluR3) $EC_{50}$=12 μM, $E_{max}$=−90%. For GluR6, the smooth curve is derived from a fit to the logistic equation, as Michaelis-Menten fits were significantly poorer (F-test, P<0.05). Maximuim inhibition was constrained to 100%, as an unconstrained fit yielded an extrapolated maximum inhibition >100%. Fitted parameters are $EC_{50}$=80 μM, $n_H$=0.29.

Inhibition by PS was dose-dependent, with $EC_{50}$'s of 43 μM and 12 μM at the GluR1 and GluR3 receptors, respectively (FIG. 2F). PS was also effective at inhibiting kainate responses of GluR6 receptors, but the concentration-response curve was much more shallow ($n_H$=0.29) than for GluR1 and GluR3 receptors. At higher concentrations of PS, the extent of inhibition of GluR6 kainate receptors was considerably less than for the GluR1 or GluR3 AMPA receptors. At 200 μM PS, GluR1 and GluR3 kainate responses were inhibited by 85±4% and 81±3% (n=3), respectively, compared to 64±2% (n=3) at 500 μM PS with the GluR6 receptor.

Table 1 tabulates the effects of a series of steroids on kainate responses mediated by GluR1, GluR3, or GluR6 receptors. As noted above for PS, the GluR6 kainate receptor tended to be less sensitive than GluR1 and GluR3 AMPA receptors to inhibition by steroids. Selectively for AMPA over kainate receptors was enhanced by substitution of a hemisuccinate moiety for the C-3 sulfate group of PS, as PS and pregnenolone hemisuccinate were about equally effective in inhibiting GluR1 and GluR3 mediated kainate currents, but pregnenolone hemisuccinate was considerably less effective than PS in inhibiting GluR6 mediated responses (15% vs. 42% inhibition). Not all sulfated steroids were observed to have inhibitory activity; in particular, 17β-estradiol-3-sulfate (100 μM) had no effect on GluR1 and GluR3 receptors and was only slightly inhibitory at GluR6 receptors (12% inhibition), demonstrating that inhibition of AMPA receptors is not a universal property of sulfated steroids.

TABLE 1

Effects of selected steroids on recombinant AMPA, kainate, and NMDA receptors expressed in Xenopus oocytes

| | Percentage change | | | |
|---|---|---|---|---|
| | AMPA | | Kainate | NMDA |
| Steroid | GluR1 | GluR3 | GluR6 | $NR1_{100}$ + NR2A |
| Pregnenolone sulfate | −85 ± 1(8)* | −73 ± 3(8)* | −42 ± 3(8)* | +281 ± 27(7)* |
| Pregnenolone hemisuccinate | −71 ± 1(4)* | −72 ± 3(3)* | −15 ± 2(3)* | +118 ± 16(16)* |
| Pregnanolone sulfate | −47 ± 12(3) | −63 ± 8(4)* | −34 ± 5(7)* | −64 ± 3(7)* |
| 17β-Estradiol-3-sulfate | −2 ± 2(3) | −8 ± 4(3) | −13 ± 4(4)* | +12 ± 3(4)* |
| 17α-Estradiol-3-sulfate | −22 ± 3(3)* | −17 ± 2(3)* | −7 ± 1(5)* | — |
| Dehydroepiandrosterone sulfate | −23 ± 3(3)* | −7 ± 1(4)* | −17 ± 5(3) | +8 ± 13(3) |
| Dehydroepiandrosterone | −16 ± 3(3)* | −7 ± 5(3) | −5 ± 1(3)* | — |

Holding potential during drug application is −100 mV. All steroids were applied at 100 μM. Oocytes injected with the indicated subunit cRNA were pre-equilibrated with steroid for 10 s prior to co-application of steroid and NMDA or kainate. Values are mean percentage change ± S.E. in the response to 100 μM NMDA ($NR1_{100}$ + NR2A) or 100 μM (GluR1 and GluR3) or 10 μM (GluR6) kainate. The number of experiments is given in parentheses.
*Indicates a statistically (P < 0.05) change in the induced current.

Modulation of Recombinant NMDA Receptors by PS and Related Steroids

Figure 3A:
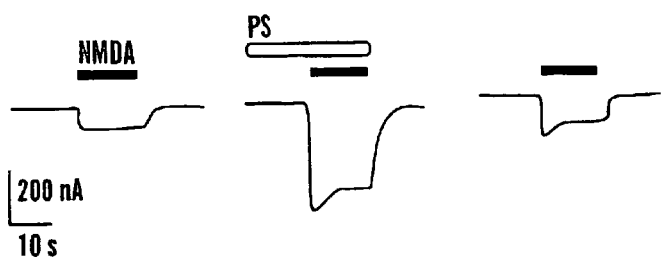
FIG. 3(A) indicates the potentiation of the 100 μM NMDA response by PS in *oocytes* injected with $NR1_{100}$+NR2A cRNA. The solid bar indicates the period of NMDA exposure; the open bar indicates the period of PS exposure.
Figure 3B:
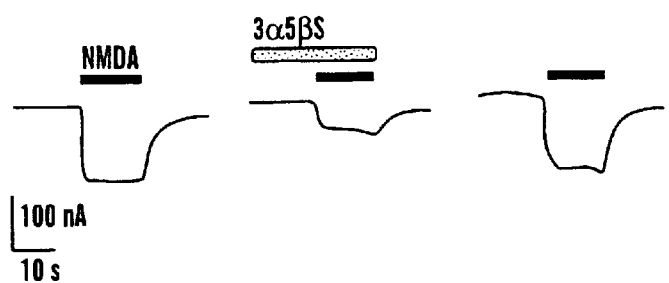
FIG. 3(B) indicates inhibition of the 100 μM NMDA response by 3α5βS in *oocytes* injected with $NR1_{100}$+NR2A cRNA. The solid bar indicates the period of NMDA exposure; the shaded bar indicates the period of 3α5βS exposure.

Xenopus oocytes co-injected with $NR1_{100}$ and NR2A cRNAs exhibited NMDA-evoked currents, which were potentiated by PS (FIG. 3A) and inhibited by its reduced metabolite 3α5βS. Steroid modulation was rapid in onset, and the degree of modulation was similar whether NMDA was applied simultaneously with the steroid modulator or after a 10 s preincubation with steroid. Reversal of steroid modulation was also rapid, with NMDA responses returning almost to control levels after a 30 s wash (FIG. 3A and B).

Figure 3C:
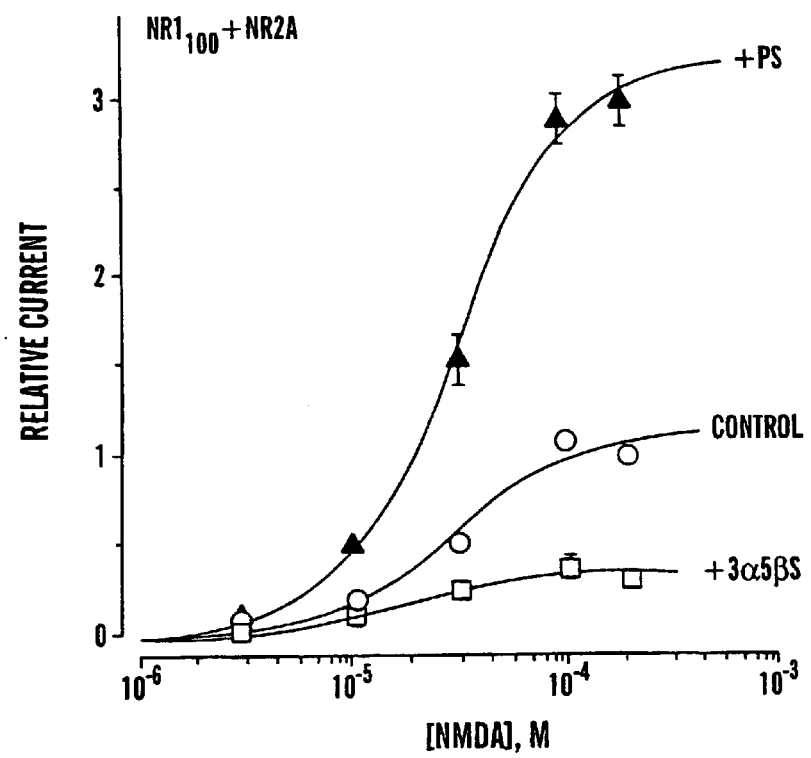
FIG. 3(C) indicates modulation of agonist efficacy by PS and 3α5βS in *oocytes* injected with $NR1_{100}$+NR2A cRNA. PS (100 μM) increases the NMDA $I_{max}$ but does not affect the $EC_{50}$. 3α5βS (100 μM) markedly reduces the NMDA $I_{max}$ with little effect on $EC_{50}$. Peak NMDA responses are normalized to the peak 100 μM NMDA response. Each data point represents the mean of three experiments. Error bars represent standard error. Smooth curves are derived from fits to the logistic equation. Fitted parameters are (control) $EC_{50}$=29 μM, $E_{max}$=1.14, $n_H$=1.43; (+PS) $EC_{50}$=30 μM, $E_{max}$=3.21, $n_H$=1.54; (+3α5βS) $EC_{50}$=15 μM, $E_{max}$=0.35, $n_H$=1.66.
Figure 3D:
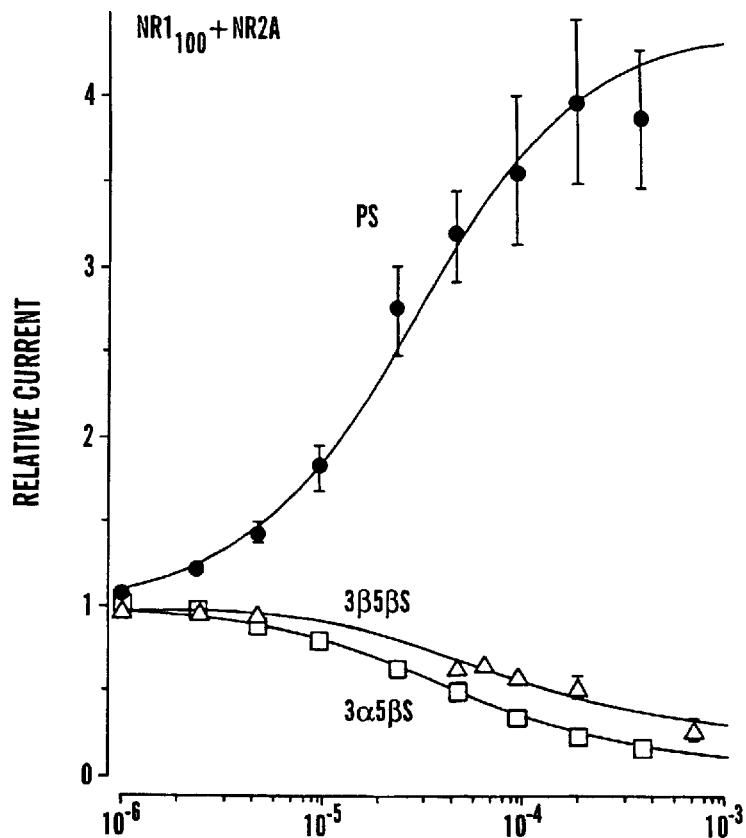
FIG. 3(D) is a graph indicating the concentration dependence of steroid modulation of the NMDA response of *oocytes* injected with $NR1_{100}$+NR2A cRNA. NMDA (100 μM) and the indicated concentration of PS (●), 3β5βS (Δ), or 3α5βS (□) were applied simultaneously for 10 s. The peak NMDA-induced current is expressed relative to the average of control NMDA responses determined before application of steroid and after steroid washout. Points indicate mean of 6 (PS and 3α5βS), and 4 (3β5βS), experiments. Error bars indicate S.E.M. Smooth curves are derived from fits to the Michaelis-Menten equation, as fits to the logistic equation yielded Hill coefficients close to 1, with no significant improvement in sum of squares (F-test, P>0.05). Fitted parameters are (for PS) $EC_{50}$=32 μM, $E_{max}$=4.43 (for 3α5βS) $EC_{50}$=41 μM, $E_{max}$=0.1; (for 3β5βS) $EC_{50}$=79 μM, $E_{max}$=0.26. (E) Concentration dependence for PS enhancement (●) and 3α5βS (Δ) and 3β50βS (□) inhibition of the NMDA response of *oocytes* injected with $NR1_{100}$ cRNA. NMDA (300 μM) and the indicated concentration of steroid were applied simultaneously. The peak NMDA-induced current is expressed relative to the average of control NMDA responses determined before application of steroid and after steroid washout. Points indicate mean of 6 (PS), 3 (3β5βS), and 3 (3α5βS) experiments. Error bars indicate S.E.M. Smooth curves are derived from fits to the Michaelis-Menten equation, as fits to the logistic equation yielded Hill coefficients close to 1, with no significant improvement in sum of squares (F-test, P>0.05). Fitted parameters are (for PS) $EC_{50}$=26 μM, $E_{max}$=2.14; (for 3α5βS) $EC_{50}$=57 μM, $E_{max}$=0.02; (for 3β5βS) $EC_{50}$=144 μM, $E_{max}$=0.17.

As shown in FIG. 3C, the potentiating effect of PS was due primarily to an increase in NMDA efficacy, which was nearly tripled in the presence of 100 μM PS, with no change in the NMDA $EC_{50}$. The $EC_{50}$ for enhancement of the 100 μM NMDA response by PS was 32 μM (FIG. 3D), with a maximum enhancement of 343%. Pregnenolone hemisuccinate also potentiates the NMDA response (Table 1), whereas 3β5βS had an inhibitory effect similar to 3α5βS, although it was slightly less potent (FIG. 3D). In contrast, allopregnanolone sulfate (3α5αS) was without effect on the NMDA induced current (8±8%, n=7), while epiallopregnanolone sulfate (3β5αS) had a modest potentiating effect (33±13%, n=7). Other steroids tested (Table 1) included 17β-estradiol-3-sulfate, which had a small but statistically significant potentiating effect, and dehydroepiandrosterone sulfate, which was inactive.

Figure 3E:
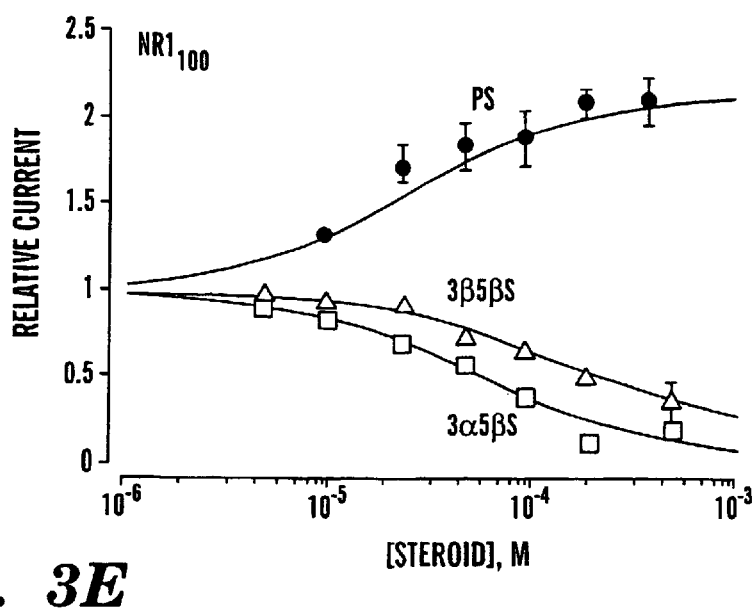
FIG. 3 is a compilation of graphical representations of data which indicate that neuroactive steroids modulate NMDA responses of *oocytes* injected with specific NMDA receptor subunits.

When oocytes were injected only with $NR1_{100}$ cRNA, the potency of PS in potentiating the NMDA induced current was similar ($EC_{50}$=26 μM) to oocytes injected with both $NR1_{100}$ and NR2A cRNA, but the maximum potentiation was decreased to 114% (FIG. 3E). In contrast, oocytes injected with $NR1_{100}$ cRNA were similar to those injected with $NR1_{100}$ plus NR2A cRNA with respect to the potency and efficacy of the inhibitory steroids 3α5βS and 3β5βS.

Methods of the Invention

Plasmids were obtained from the following individuals: Dr. Suzanne Zukin (Albert Einstein College of Medicine, Bronx, N.Y.), $NR1_{100}$; Dr. Shigetada Nakanishi (Kyoto University Faculty of Medicine, Kyoto, Japan), NR2A; Dr. Stephen Heinemann (Salk Institute, San Diego, Calif.), GluR1 (flop), GluR3 (flop), and GluR6. Plasmids were linearized with BamH1 ($NR1_{100}$), XhoI (NR2A, GluR1, GluR3) or XbaI (GluR6) prior to in vitro transcription with T3 (GluR1, GluR3, GluR6) or T7 ($NR1_{100}$, NR2A) RNA polymerase using the Message Machine kit (Ambion, Austin, Tex.). Oocytes were harvested and maintained in ND96 (NaCl, 96 mM; $MgCl_2$, 1 mM; KCl, 2 mM; $CaCl_2$, 1.8 mM; HEPES, 5 mM; pyruvate, 2.5 mM; 50 mg/ml gentamicin) according to published protocols (Stuhmer and Parekh, Electrophysiological recordings from Xenopus oocytes, in: B. Sakmann, E. Neher (Eds.), Single-Channel Recording, 2nd edn., Plenum Press, New York, 1995, pp. 341–356). RNA solutions (50–70 nl) were injected into oocytes for delivery of $NR1_{100}$ (5 ng), $NR1_{100}$:NR2A (1:10 ng), GluR1 (5 ng). GluR3 (5 ng), or GluR6 (20 ng). Oocytes were incubated in ND96 at 18–20° C. for 3–7 days prior to electrophysiological recording.

Steroids were obtained commercially from Steraloids, (Wilton, N.H.) and Sigma (St. Louis, Mo.), except 3α5βS, 3β5αS, and 3β5βS, which were provided by Dr. Robert Purdy (Dept. of Psychiatry, University of California, San Diego, Calif.). Steroid solutions were prepared as 70–100 mM frozen stocks in dimethyl sulfoxide (DMSO). The final DMSO concentration of all recording solutions was between 0.1% to 0.5% and was constant within an experiment. Over this concentration range, DMSO alone does not affect kainate or NMDA responses.

Perfusion control and data acquisition were carried out using an automated oocyte electrophysiology workstation that was developed for the rapid collection of concentration-response data and real-time waveform analysis (Yaghoubi et al., Soc. Neurosci. Abstr. 20: 1109 (1995)). This system is implemented on a Macintosh IIci computer (Apple Computer, Cupertino, Calif.) equipped with MacA-DIOS II data acquisition and control hardware (GW Instruments, Somerville, Mass.). Drug application is controlled by the computer through a series of valves, using custom-written software based on the SuperScope II development environment, improving the efficiency and reproducibility of data collection. Experiments were carried out using an Axoclamp-2A voltage clamp amplifier (Axon Instruments, Foster City, Calif.) in two-electrode voltage clamp mode. Intracellular microelectrodes (1–3 MΩ) were filled with 3 M KCl. Oocytes were perfused continuously with Mg-free Ringer (NaCl, 96 mM; KCl, 2 mM; $CaCl_2$, 1.8 mM; HEPES, 5 mM). Membrane potential was clamped at −60 to −70 mV and stepped to −100 mV at the start of data acquisition unless otherwise stated. PS concentration-response curves for GluR1 and GluR3 experiments were determined at −80 mV due to high levels of receptor expression which resulted in off-scale current responses at −100 mV. Current and voltage recordings were digitized at 100 Hz for analysis. GluR6 injected *oocytes* were treated for 10 min with 10 μg/ml concanavalin A to prevent fast desensitization.

Modulation of NMDA and kainate responses by steroid compounds in expressed as percentage change, [(I'/I)−1]× 100%, where I is the average of four control responses, obtained from an *oocyte* before application and after washout of steroid, and I' is the average of two responses obtained from the same *oocyte* in the presence of steroid. Peak NMDA responses were normalized to the maximal (100 μM) NMDA response for analysis and comparison except where otherwise specified. Peak kainate-induced currents are normalized to the maximal (100 μM for GluR1 and GluR3 receptors; 10 μM for GluR6 receptors) kainate response. Kainate, rather than AMPA, was used to activate GluR1 and GluR3 receptors, because desensitization was much less with kainate than with AMPA. In some experiments, *oocytes* were pre-equilibrated with steroid modulator for 10 s prior to application of NMDA, but this preincubation was found to have little if any effect on the extent of modulation of the peak NMDA-induced current, and the preincubation period was therefore omitted in subsequent experiments. Results are expressed as mean±S.E.M. Statistical comparisons were made using Student's t-test.

EXAMPLE 2

The $Ca^{2+}$-sensitive dye Fluo-3, AM and a trypan blue exclusion assay were employed to measure NMDA-induced $Ca^{2+}$ influx and cell death, respectively, in primary cultures of rat hippocampal neurons. A number of pregnane and pregn-5-ene steroids were examined for their ability to alter the increase in $[Ca^{2+}]_i$ and the neuronal death produced by NMDA exposure.

Negative Modulators

Figure 4A:
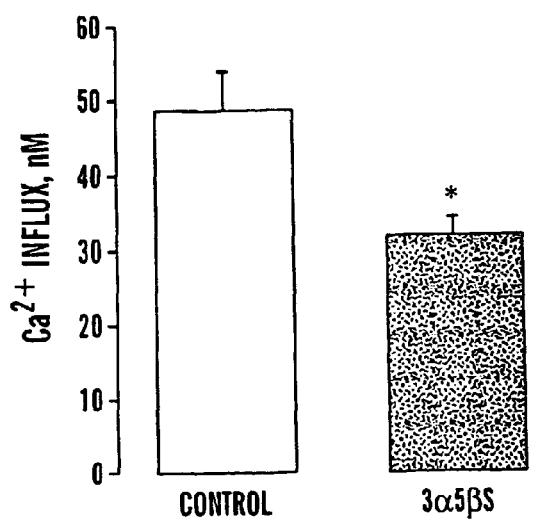
FIG. 4 is a graphical representation of data indicating that 3α5βS inhibits NMDA receptor function. A, 3α5βS (100 μM) inhibits the 5 μM NMDA-evoked increase in $[Ca^{2+}]_i$. Results are expressed as mean % neuronal death±S.E.M. of 8 experiments. B, 3α5βS (100 μM) increases the $EC_{50}$ and reduces the $E_{max}$ for neuronal death caused by acute NMDA exposure. 3α5βS or DMSO vehicle was present during the 15 min NMDA exposure only. Results are expressed as mean % neuronal death±S.E.M. of 16 (○, DMSO control) and 4 (●, 3α5βS) experiments. Smooth curves were determined by nonlinear regression using the logistic equation applied to the pooled data (Vehicle treated: $E_{max}$=80%, $EC_{50}$=28 μM, $n_H$=2.1; 3α5βS treated: $E_{max}$=63%, $EC_{50}$=71 μM, $n_H$=1.8). C, The effect of 3α5βS on the neuronal death produced by acute 30 μM NMDA exposure is dose dependent. Results are expressed as mean % neuronal death±S.E.M. of 4 experiments. The smooth curve was determined by nonlinear regression using the logistic equation applied to the pooled data ($I_{max}$=97% $EC_{50}$=45 μM, $n_H$=2.5). D, Under chronic (16 hour) exposure conditions, 3α5βS (100 μM) reduces the NMDA efficacy but does not alter the affinity. 3α5βS or DMSO vehicle was present during the 16 hour NMDA exposure only. Results are expressed as mean % neuronal death±S.E.M. of 10 (DMSO control; empty circles) and 6 (3α5βS; filled circles) experiments. Smooth curves were determined by nonlinear regression using the logistic equation applied to the pooled data (Vehicle treated: $E_{max}$=86%, $EC_{50}$=12 μM, $n_H$=1.9; 3α5βS treated: $E_{max}$=70%, $EC_{50}$=15 μM, $n_H$=2.0) $EC_{50}$ and $E_{max}$ values were determined for each experiment by nonlinear regression using the logistic equation. The break in the x-axis represents a change from linear to logarithmic scale. * Indicates a statistically significant (P<0.05) difference from NMDA control.
Figure 4B:
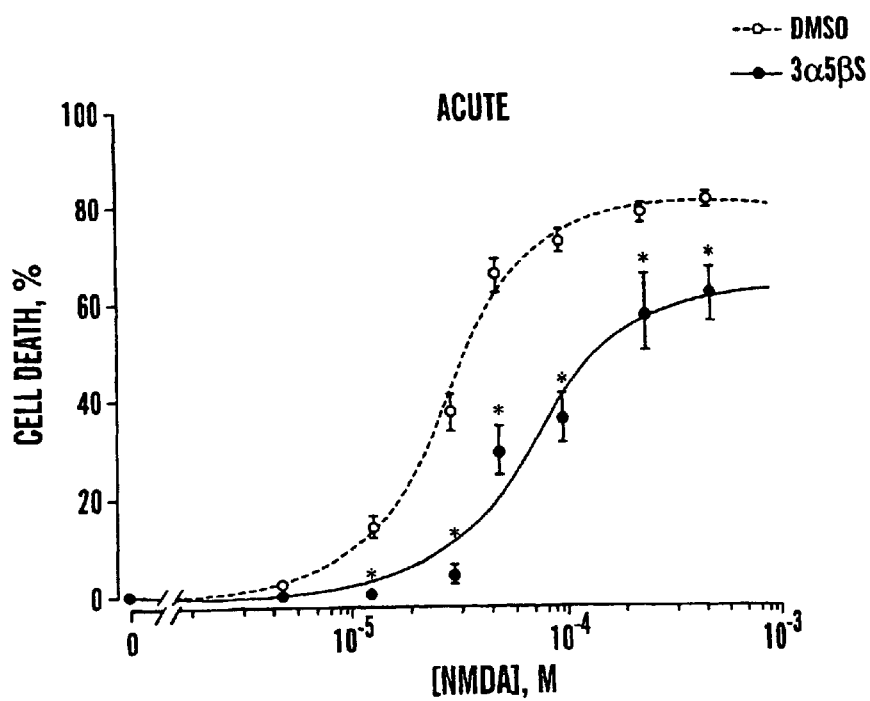
Figure 4C:
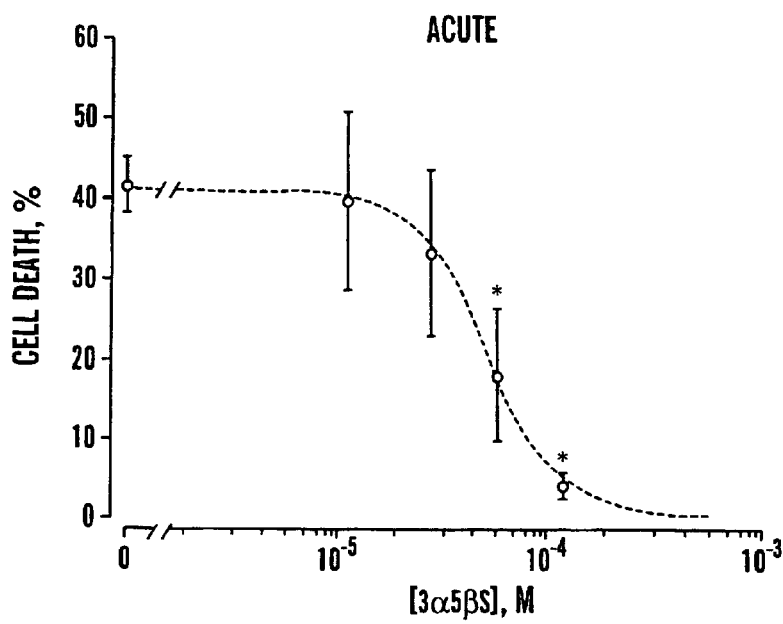
Figure 4D:
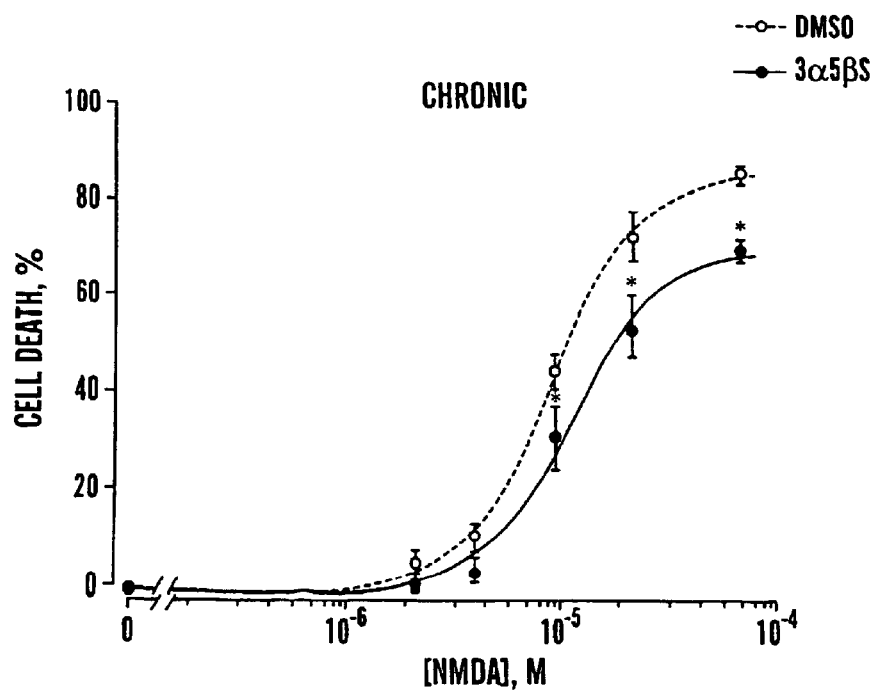

Previously several reduced metabolites of progesterone that modulate currents evoked by NMDA were identified (Farb D H, and Gibbs T T (1996) Steroids as modulators of amino acid receptor function, in CNS neurotransmitters and neuromodulators: neuroactive steroids (Stone T W, ed.) pp 23–36, CRC Press, New York). 3α5βS was the first steroid found to inhibit NMDA-induced currents in cultured neurons (Park-Chung et al., *Mol Pharmacol* 46: 146–150 (1994)). Consistent with this negative modulation of the NMDA response, 3α5βS (100 μM) reduces the 5 μM NMDA-evoked $Ca^{2+}$ influx by 32±5% (n=8) (FIG. 4A). Further, 3α5βS protects neurons from the cell death produced by acute (15 min) exposure to NMDA, raising the $EC_{50}$ for NMDA-induced neuronal death from 28 μM to 71 μM and lowering the maximal NMDA-induced excitotoxicity from 80% to 63% cell death (FIG. 4B). This effect is dose-dependent, with an $EC_{50}$ of 45 μM and a 97% maximal inhibition ($I_{max}$) of the cell death induced by 30 μM NMDA (FIG. 4C). The neuronal death caused by chronic (16 h) NMDA treatment is also attenuated by 3α5βS, which, under these conditions, reduces the NMDA $E_{max}$ from 86% to 70% cell death without affecting the NMDA $EC_{50}$ (FIG. 4D).

In addition to its effects on the NMDA response, 3α5βS inhibits currents elicited by AMPA and kainate (Park-Chung et al., *Mol Pharmacol* 46: 146–150 (1994)), raising the possibility that the effect of the steroid on NMDA-induced neuronal death might not be specific to the NMDA receptor. 101 μM DNQX (a selective non-NMDA glutamate receptor antagonist (Honore et al., *Science* 84:8215–8219 (1988)) and 100 μM SR-95531 (a selective $GABA_A$ receptor antagonist (Farrant M, and Webster R A (1989) GABA antagonists: their use and mechanisms of action, in *Drugs as Tools in Neurotransmitter Research* (Boulton A A, Baker, G B and Juorio, A V, eds.) pp 161–219, Humana Press Inc., Clifton) have no effect on NMDA-induced neuronal death (not shown), arguing that the $GABA_A$, AMPA, and kainate receptor types do not play a significant role in this process.

Figure 5:
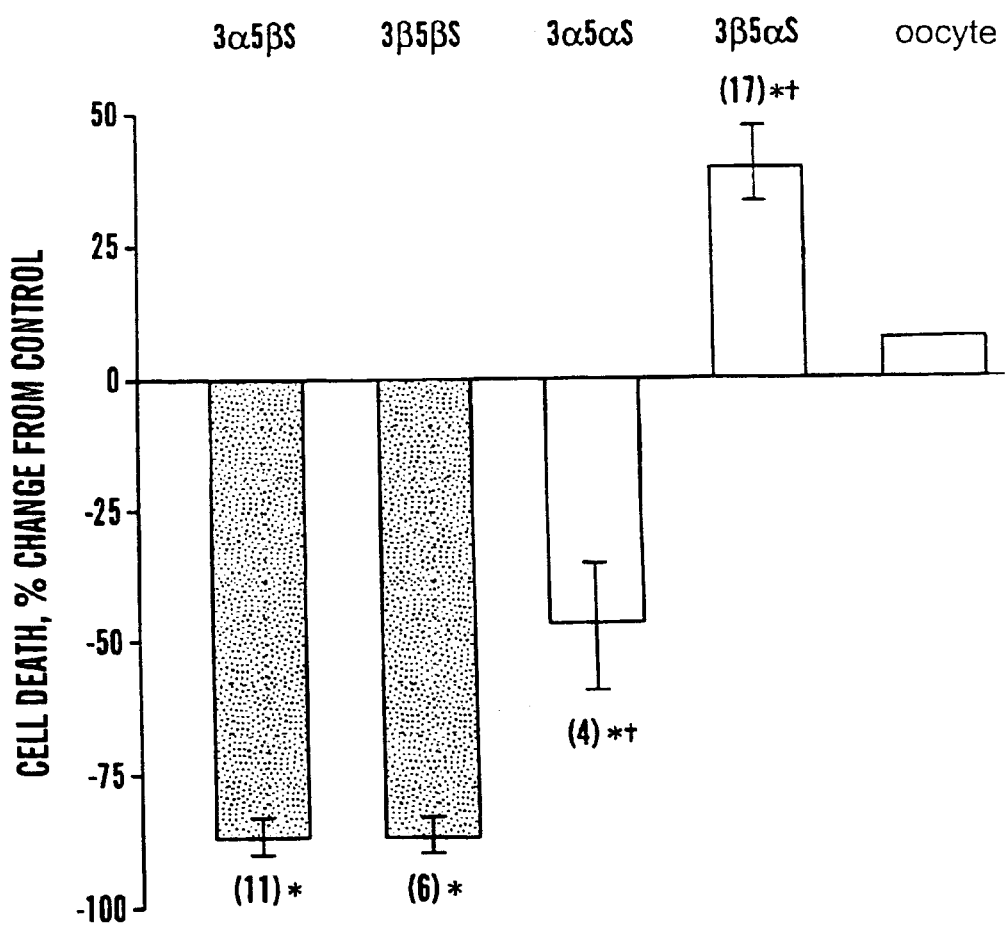
FIG. 5 is a bar graph of data indicating inhibition of NMDA-induced neuronal death by 3α5S isomers is stereospecific. The neuronal death caused by acute exposure to 30 μM NMDA is nearly abolished by 5β isomers. 3α5αS (100 μM) is only half as effective, whereas 100 μM 3β5αS potentiates neuronal death. Results are expressed as mean % neuronal death±S.E.M., with the number of experiments indicated in parentheses. * Indicates a statistically significant (P<0.05) difference from NMDA control; † indicates a statistically significant difference from 3β5βS and 3α5βS.

While 3α5βS nearly eliminates the toxic effects of an acute exposure to 30 μM NMDA, its stereoisomer 3α-hydroxy-5α-pregnan-20-one sulfate (3α5αS) is only half as effective, producing a 47±12% (n=4) inhibition of neuronal death (FIG. 5). Strikingly, whereas 3β5βS reduces NMDA-induced currents and neuronal death (86±3% inhibition; n=6), its C5α isomer, 3β-hydroxy-5α-pregnan-20-one sulfate (3β5αS), both potentiates NMDA-induced currents (Park-Chung et al., *Mol Pharmacol* 52: 1113–1123 (1997)) and exacerbates neuronal death by 40±7% (n=17). This shows that, as with their effects on NMDA-evoked currents, the neuroprotective effects of these sulfated steroids are contingent upon the stereochemistry of the A-B ring junction, whereas. stereochemistry at C3 appears to be important only for C5α isomers.

Figure 6A:
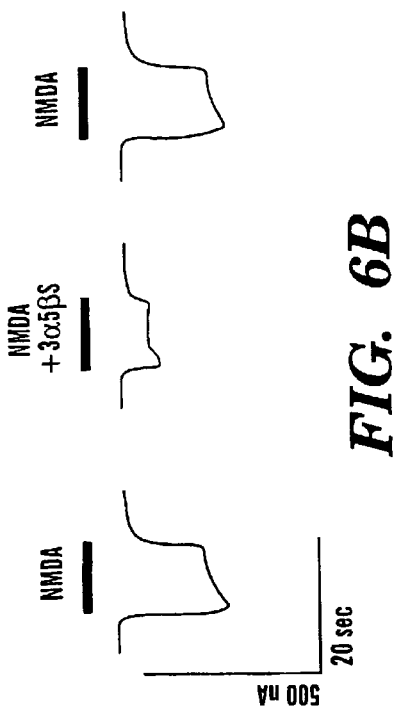
FIG. 6 is a graphical representation of data which indicates that modulation of NMDA-induced current by steroid sulfates and hemisuccinates. A: Inhibition of the 100 μM NMDA-induced current by 3α5βHS in a *Xenopus* oocyte expressing $NR1_{100}$ and NR2A subunits. B: Inhibition of the NMDA-induced current by 3α5βS is shown for comparison. C: Potentiation of the 100 μM NMDA-induced current by PHS in a *Xenopus* oocyte expressing $NR1_{100}$ and NR2A subunits. D: Potentiation of the NMDA-induced current by PS is shown for comparison.
Figure 6B:
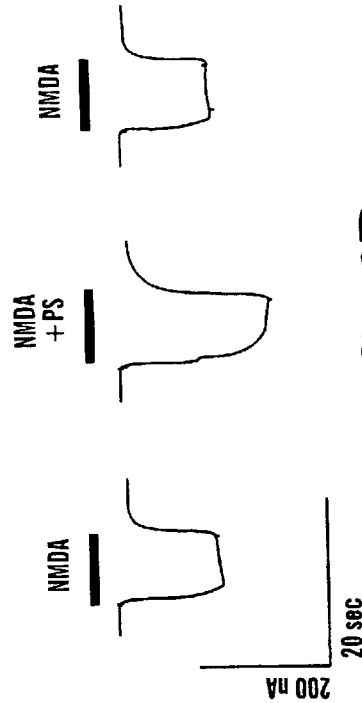
Figure 7A:
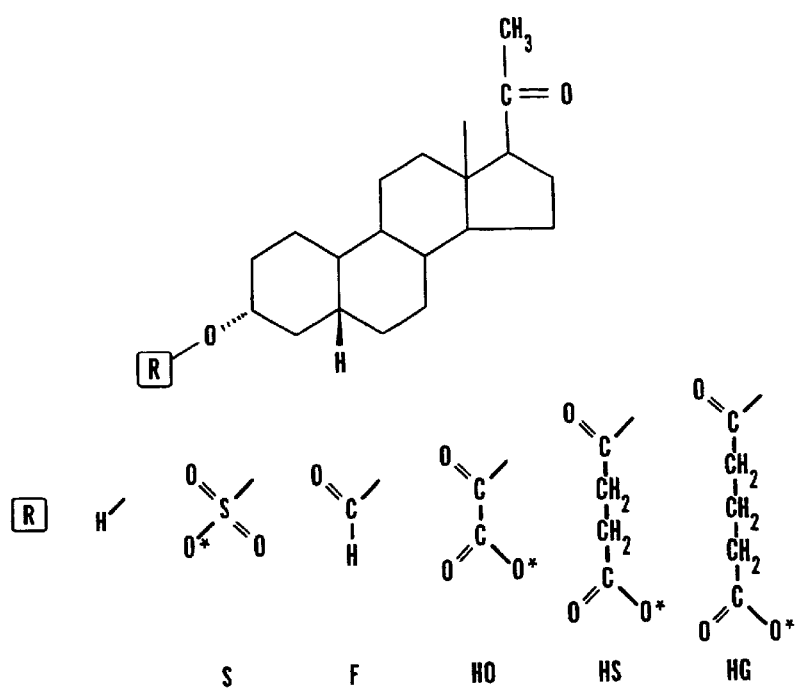
FIG. 7 indicates inhibition of NMDA-mediated neuronal death by pregnane steroids is dependent upon the C3 ester group. A: Structures of 3α5β, 3α5βS, 3α5βF, 3α5βHO, 3α5βHS, 3α5βHG. Note that 3α5β and 3α5βF are uncharged, while the other three are negatively charged. B: Negatively charged pregnane steroids are more effective as inhibitors of the NMDA response. Bars show mean percentage decrease in the 100 μM NMDA-induced current in the presence of 100 μM of the indicated steroid in *oocytes* expressing NR1$_{100}$ and NR2A subunits. Error bars indicate S.E.M. Number of *oocytes* is given in parentheses. * Significant (p<0.05) decrease in NMDA-induced current. † Significantly (p<0.05) lower activity than 3α5βHO, 3α5βHS, and 3α5βHG. C: Negatively charged pregnane steroids inhibit the 5 μM NMDA-mediated Ca$^{2+}$ influx in rat hippocampal cultures. Bars show mean percentage reduction of the NMDA-induced rise in [Ca$^{2+}$]$_i$ in the presence of the indicated steroid (100 μM, except 3α5β, 50 μM). Error bars indicate S.E.M.; the number of experiments is given in parentheses. * Significant (p<0.05) decrease in NMDA-induced elevation of [Ca$^{2+}$]$_i$. D: 3α5βHO, 3α5βHS, and 3α5βHG (100 μM) inhibit 30 μM NMDA-induced death of rat hippocampal neurons (* p<0.05). 3α5β (50 μM) and 3α5βF (100 μM) did not protect significantly against NMDA-induced toxicity. Results are expressed as mean % neuronal death±S.E.M. with the number of experiments indicated in parentheses. † Significantly (p<0.05) less protection than 3α5βHO, 3α5βHS, or 3α5βHG.
Figure 7B:
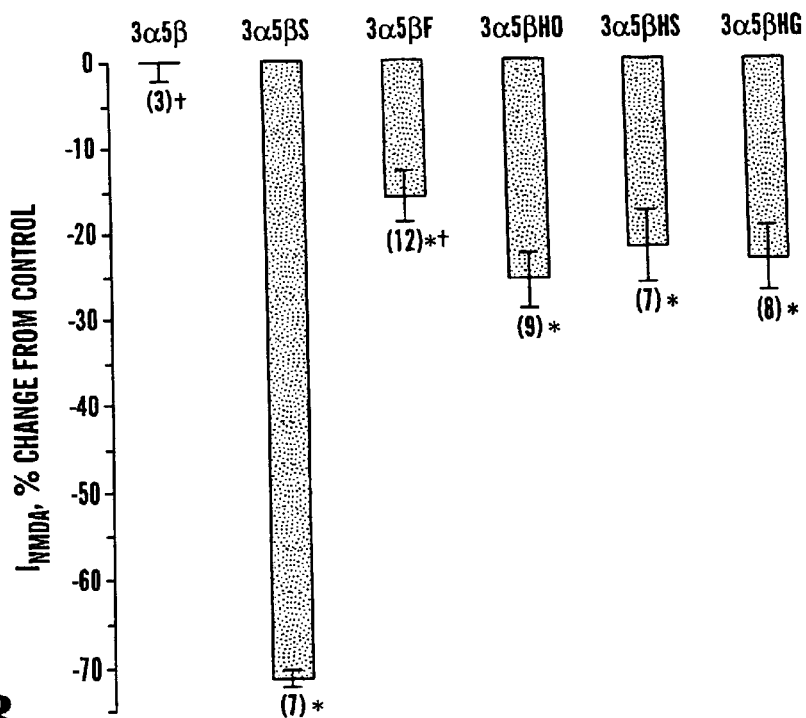

To elucidate further the structure-activity relationships for modulation of the NMDA receptor by steroids, a series of carboxylic acid derivatives of 3α5β were synthesized (FIG. 7A). The three negatively-charged derivatives, pregnanolone hemioxylate (3α5βHO), pregnanolone hemisuccinate (3α5βHS), and pregnanolone hemiglutarate (3α5βHG) are about equally effective in inhibiting $I_{NMDA}$, the NMDA-induced current of *Xenopus oocytes* expressing $NR1_{100}$+ NR2A subunits, but the degree of inhibition is substantially less than is observed with 3α5βS (FIGS. 6A, 6B and 7B). The uncharged pregnanolone formate (3α5βF) significantly inhibits $I_{NMDA}$, but is significantly less effective than the dicarboxylic acid derivatives, while 3α5β itself is inactive.

Figure 7C:
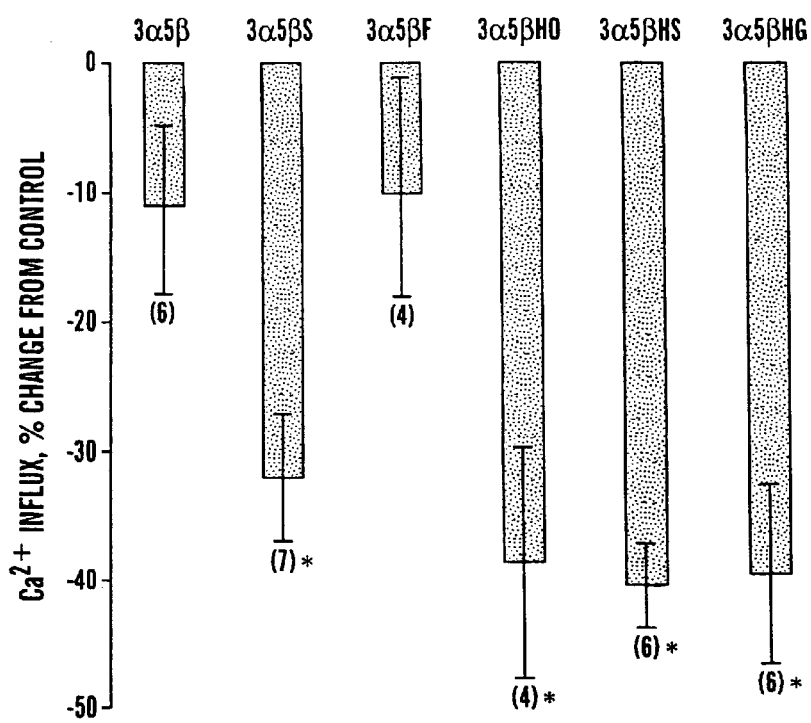
Figure 7D:
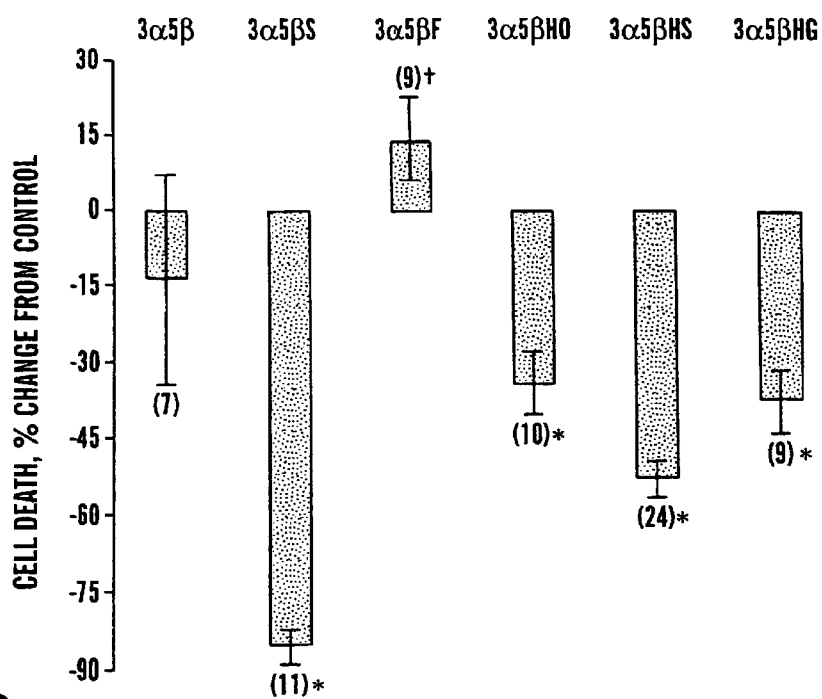

Consistent with these results, the negatively-charged 3α5βHO, 3α5βHS, and 3α5βHG inhibit the NMDA-induced rise in $[Ca^{2+}]_i$ by approximately 40% in primary hippocampal cultures, while the uncharged 3α5β and 3α5βF have no significant effect on NMDA-induced $Ca^{2+}$ accumulation (FIG. 7C). Similarly, 3α5βHO, 3α5βHS, and 3α5βHG are neuroprotective, reducing neuronal death caused by acute exposure to 30 μM NMDA by 35±6% (n=10), 54±3% (n=24), and 38±6% (n=9), respectively (FIG. 7D), while 3α5β and 3α5βF do not exhibit significant neuroprotective activity.

Positive Modulators

Figure 6C:
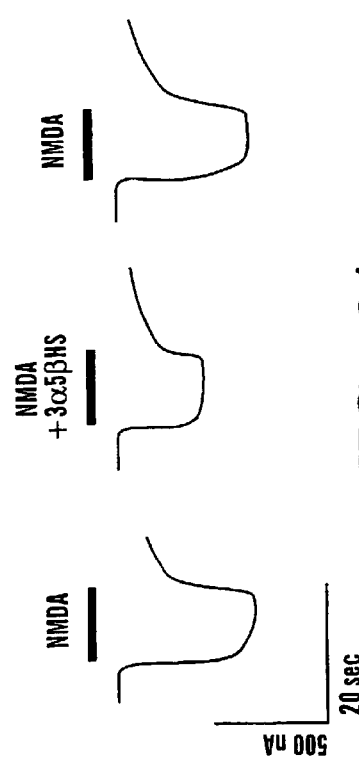
Figure 6D:
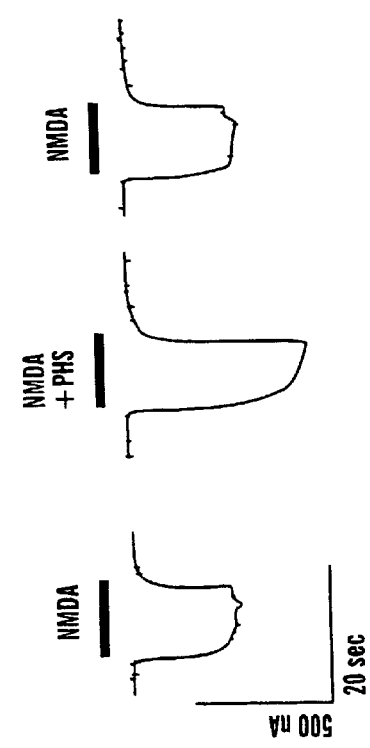
Figure 8A:
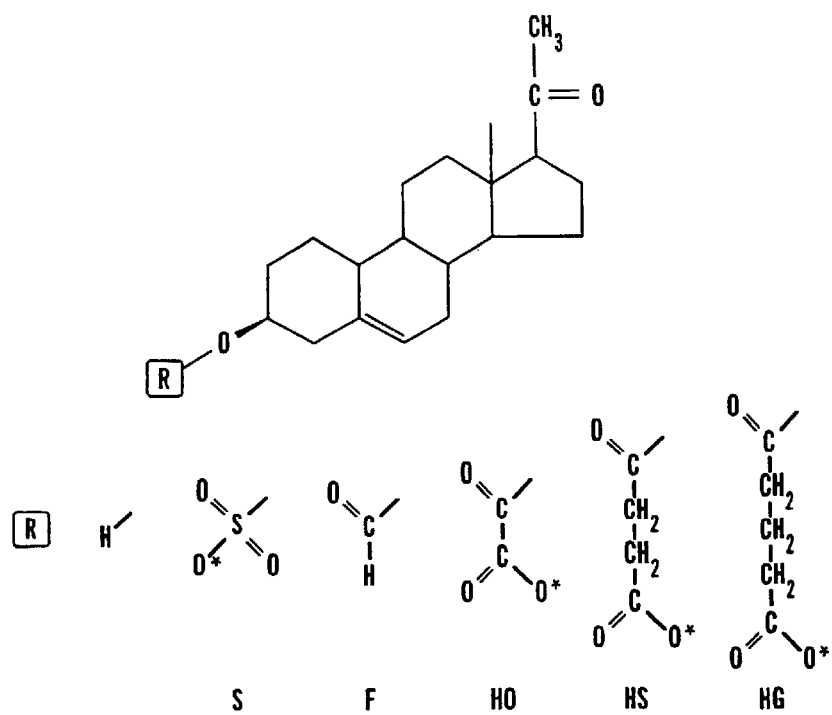
FIG. 8 indicates pregn-5-ene steroid-mediated exacerbation of NMDA receptor function is dependent upon the C3 ester group. A: Structures of pregnenolone (P), PS, PF, PHO, PHS, and PHG. Note that pregnenolone and PF are uncharged, while the other three are negatively charged. B: PHS and PHG show greatest potentiation of the NMDA response. Bars show mean percentage increase in the 100 μM NMDA-induced current in the presence of 100 μM of the indicated steroid in *oocytes* expressing NR1$_{100}$ and NR2A subunits. Error bars indicate S.E.M. Number of *oocytes* is given in parentheses. * Significant (p<0.05) increase in NMDA-induced current. † Significantly (p<0.05) lower activity than PHO, PHS, and PHG. C: Negatively charged pregn-5-ene steroids potentiate the 5 μM NMDA-mediated Ca$^{2+}$ influx in rat hippocampal cultures. Bars show mean percentage potentiation of the NMDA-induced rise in [Ca$^{2+}$]$_i$ in the presence of the indicated steroid (100 μM, except pregnenolone, 20 μM). Error bars indicate S.E.M.; the number of experiments is given in parentheses. * Significant (p<0.05) increase in NMDA-induced elevation of [Ca$^{2+}$]$_i$. † Significantly (p<0.05) less potentiation than PHG. D: PHO, PHS, and PHG (100 μM) exacerbate NMDA-induced death of rat hippocampal neurons (* p<0.05). Results are expressed as mean % neuronal death±S.E.M. with the number of experiments indicated in parentheses. † Significantly (p<0.05) less protection than PHO, PHS, or PHG.
Figure 8B:
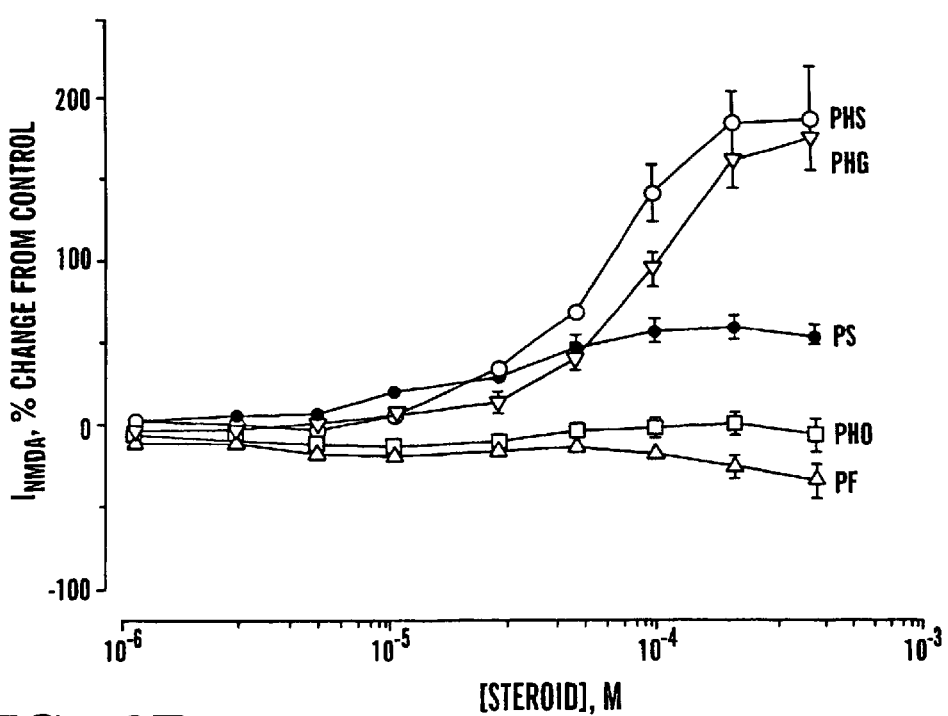

PS is a potent positive modulator of NMDA receptor function (Wu et al., *Mol Pharmacol* 40: 333–336 (1991); Bowlby M R, *Mol Pharmacol* 43: 813–819 (1993)). To evaluate the role of the sulfate ester group at C3, the effects of pregnenolone, pregnenolone formate (PF), pregnenolone hemioxylate (PHO), pregnenolone hemisuccinate (PHS), and pregnenolone hemiglutarate (PHG) were examined (FIG. 8). NMDA receptor subunit cRNA indicate that the negatively-charged PHS and PHG are effective positive modulators of the NMDA receptor, more than doubling the response to 100 μM NMDA (FIG. 8B). Interestingly, potentiation of $I_{NMDA}$ increased with chain length of the dicarboxylic acid derivatives, with PHS and PHG potentiating the NMDA response to a greater extent than PS (FIGS. 6C, 6D, and 8B), whereas PHO and PF exhibited little activity. Pregnenolone itself is also without effect (5±2%, n=3).

Figure 8C:
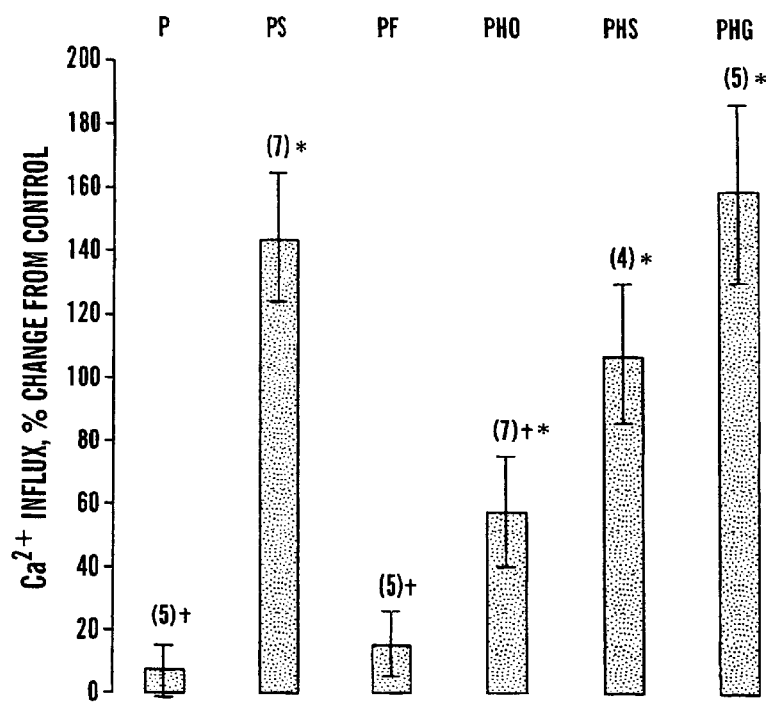
Figure 8D:
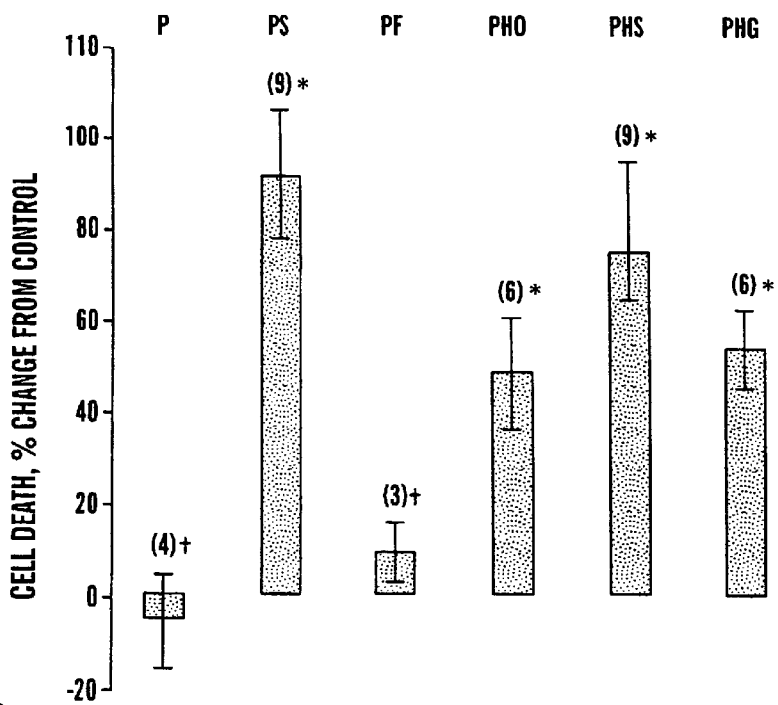

NMDA-induced $Ca^{2+}$ accumulation by hippocampal neurons in culture is enhanced by PHS (113±22%, n=4) and PHG (146±29%, n=5), consistent with their potentiation of $I_{NMDA}$, while pregnenolone and PF are without effect (FIG. 8C). However, NMDA-induced $Ca^{2+}$ accumulation is also significantly increased by PHO (62±17%, n=7), even though PHO does not enhance the NMDA-induced current. The effects of these steroids on NMDA-induced excitotoxicity are in agreement with their effects on NMDA-induced $Ca^{2+}$ accumulation. The neutral pregnenolone and PF are ineffective, while the negatively charged PHO, PHS and PHG exacerbate NMDA-induced cell death by 48±12% (n=6), 80±16% (n=9), and 54±9% (n=6), respectively (FIG. 8D).

Figure 9:
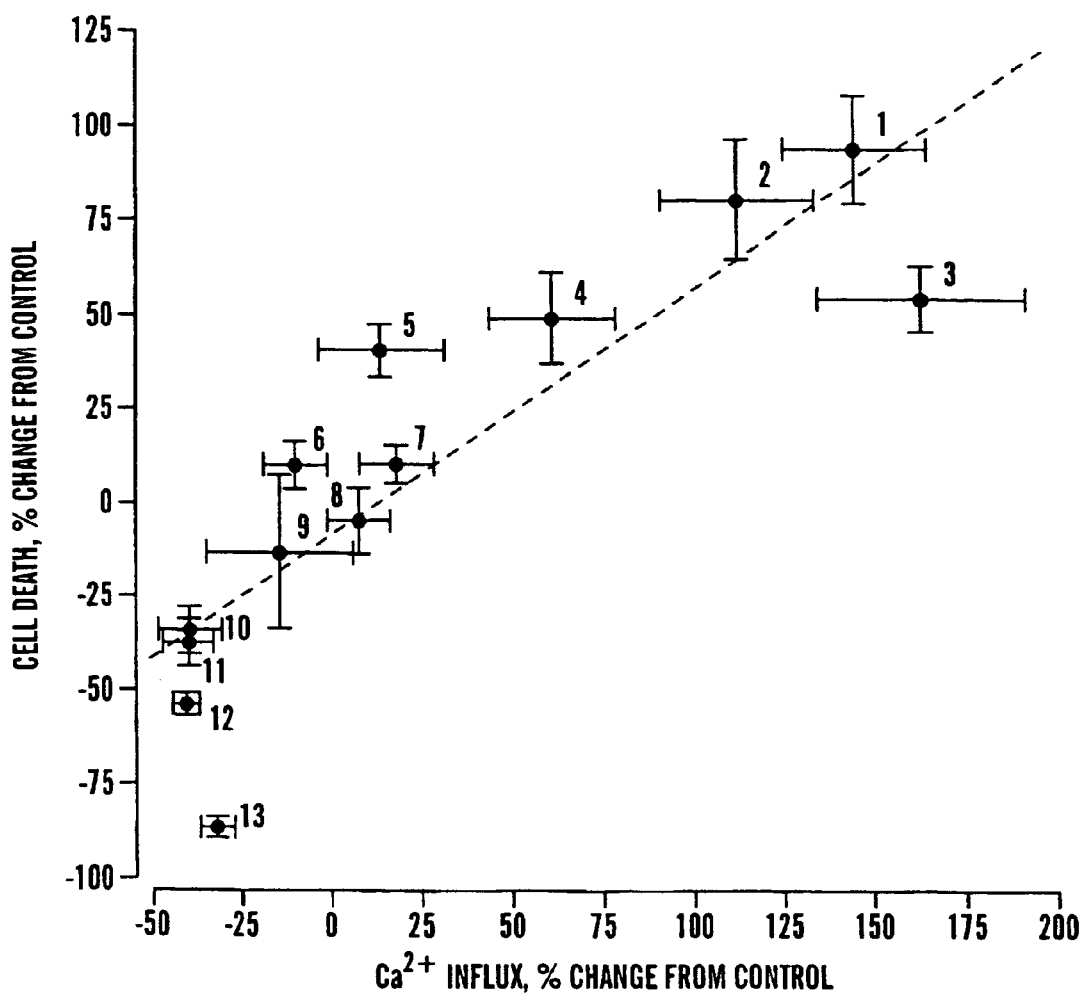
FIG. 9 is a graphical representation of data indicating steroid modulation of acute NMDA-induced neuronal death is through an interaction with the NMDA receptor. To determine if steroid modulation of acute NMDA-induced cell death is correlated to modulation of NMDA-induced increases in [Ca$^{2+}$]$_i$, the steroid-mediated change (%) in excitotoxicity is plotted against the change (%) in NMDA-induced Ca$^{2+}$ influx. Steroid modulation of NMDA-induced cell death is strongly correlated to modulation of NMDA-induced increases in [Ca$^{2+}$]$_i$ (r=0.87) 1: PS; 2: PHS; 3: PHG; 4: PHO; 5: 3β5αS; 6: PF; 7: 3α5βF; 8: pregnenolone; 9: 3α5β; 10: 3α5βHO; 11: 3α5βHG; 12: 3α5βHS; 13: 3α5βS. Results are expressed as mean±S.E.M. of at least three experiments.

The excitotoxicity produced by excessive NMDA receptor stimulation has been implicated in the neurodegeneration associated with a number of CNS diseases and insults (Rothman et al., *Ann Neurology* 19: 105–111. (1986); Gómez-Pinilla, et al., *Exp Neurol* 104: 118–124 (1989); Greenamyre, J. T., *Neurobiol Aging* 12: 334–336 (1991); Greenamyre et al., *Arch Neurol* 48: 977–981 (1991); Weaver, et al., *Proc Natl Acad Sci USA* 94: 10450–10454 (1997)). Evidence indicates that neuronal death results from NMDA receptor-mediated activation of a $Ca^{2+}$-dependent enzymatic cascade involving lipid peroxidation and protein and DNA degradation (Choi, D. W., *J Neurobio* 23: 1261–1276 (1992); Chan, P. H., *Stroke* 27: 1124–1129 (1996)). The present results, demonstrating that modulation by steroids of NMDA-induced $Ca^{2+}$ uptake is correlated with modulation of NMDA-induced neuronal death (FIG. 9), support this view, and indicate that this rapid functional assay can be usefully employed to identify steroids with neuroprotective activity.

In the present study, 3α5βS is also demonstrated to markedly inhibit NMDA-induced changes in $[Ca^{2+}]_i$ and neuronal death under both acute and chronic exposure conditions, consistent with previous finding that 3α5βS inhibits NMDA-induced currents in neurons maintained in primary culture (Park-Chung, et al., *Mol Pharmacol* 46: 146–150 (1994)). It is interesting that, in acute treatments, 3α5βS reduces both the NMDA $EC_{50}$ and $E_{max}$ for causing cell death, while only reducing the $E_{max}$ in chronic treatments. The reason for this difference is unclear, but may indicate metabolic conversion of 3α5βS, such as through the action of a steroid sulfatase, during the course of the chronic treatment, or an adaptive change at the NMDA receptor itself.

Stereochemistry

To investigate the structural requirements for steroid inhibition of NMDA-induced neuronal death, 3α5β and stereoisomers of 3α5βS were assayed for activity, as were several related synthetic pregnane steroids. 3α5βS is as effective as 3α5βS at protecting against the neuronal death produced by acute exposure to NMDA. This suggests that the stereochemistry at C3 is not critical for inhibition of NMDA-induced neuronal death by the C5β pregnane isomers. Notably, the isomers with C5α stereochemistry exhibit reduced neuroprotective activity as compared to the C5β isomers. 3α5αS is about half as effective as 3α5βS and 3β5βS in protecting against NMDA-induced cell death, whereas 3β5αs actually exacerbates the toxicity of NMDA and potentiates the NMDA-induced elevation of $[Ca^{2+}]_i$. These results are in agreement with previous electrophysiological studies of voltage-clamped chick spinal cord neurons in primary culture, in which 3α5βs and 3β5βS are strong inhibitors of the NMDA-induced current, 3α5αs is a weaker inhibitor, and 3β5αs weakly potentiates the NMDA response (Park-Chung, et al., *Mol Pharmacol* 52: 1113–1123 (1997)).

Figure 10:
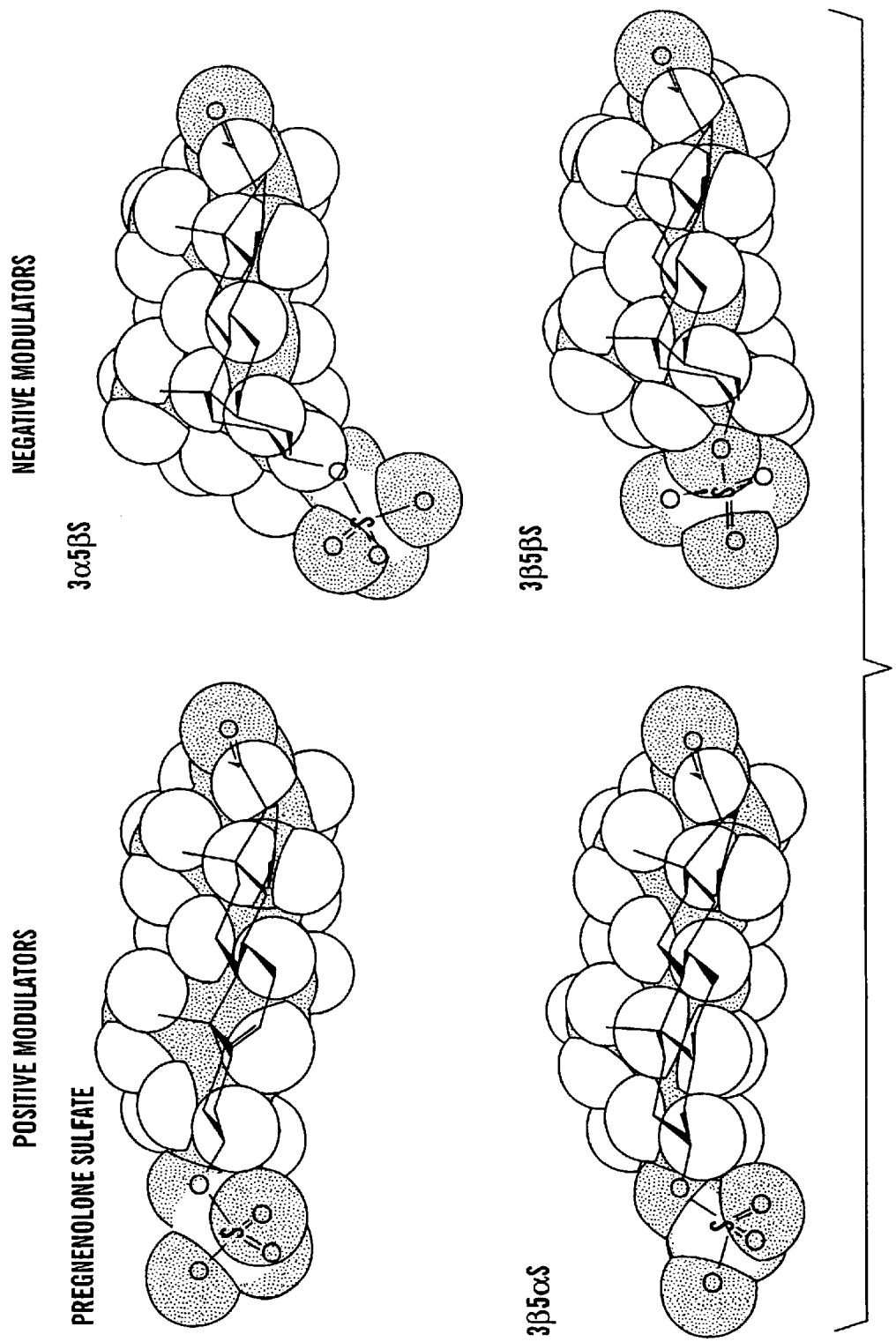
FIG. 10 is a schematic of positive modulators and negative modulators. of NMDA receptor activity. Steroid activity at the NMDA receptor is stereospecific. 5β steroid isomers (with A-B ring junction in the cis conformation) with a negatively charged group at C3, such as 3α5βS and 3β5βS, inhibit NMDA receptor responses. In this orientation, C3 stereochemistry is not a determinant of activity. In contrast, the more planar 5α isomers (with the A-B ring junction in the trans conformation) are active positive modulators only when the negatively charged group at C3 is in the β orientation; 3β5αS and PS potentiate the NMDA response, while 3α5αS is inactive or possesses much reduced inhibitory activity.

The results indicate that stereochemistry at the A-B ring junction is an important determinant of the activity of pregnanes with a negatively-charged group at C3. The effect of C5α stereochemistry on the structure of the steroid molecule is to flatten out the ring system into a more planar configuration, much like the effect of the C5–C6 double bond in the pregn-5-ene series (FIG. 10). Because competition experiments suggest that positive and negative modulation by steroids are mediated by distinct sites (Park-Chung, et al., *Mol Pharmacol* 52: 1113–1123 (1997)), it seems likely that the more planar ring structure of the pregn-5-enes and C5α pregnanes improves the fit of the steroid molecule to the potentiating site and/or impairs its fit to the inhibitory site.

Methods of the Invention

Materials

Steroids were used at 100 μM, except where otherwise stated. PS and 17β-estradiol were obtained commercially from Steraloids (Wilton, N.H.).

Formate esters were prepared by treating a solution of the steroid (400 mg) in dry dichloromethane (30 ml) with triethylamine (2.4 ml), 4-dimethylpyridine (160 mg) and formic acid (0.32 ml). The mixture was cooled to -20° C. and acetic anhydride (1.9 ml) added dropwise over a 30 min period with stirring. The reaction mixture was then warmed to 0° C. for 30 min and then the reaction stopped by the addition of methanol (1.0 ml). After evaporation of the solvents in vacuo, the residue was partitioned between ethyl acetate (10 ml) and aqueous 1N HCl. The organic phase was washed twice with 1N HCl (10 ml) and water (10 ml), and evaporated to dryness. The product was crystallized twice from a mixture of acetone and hexane. The hemioxalate esters were prepared as described above, using 568 mg oxalic acid instead of formic acid. The hemiglutarate esters were prepared as follows: To a solution of steroid (400 mg) in dry pyridine (6 ml) was added glutaric anhydride (400 mg) and 4-pyrolidinopyridine (40 mg). The mixture was allowed to stand at room temperature in the dark for 4 days, when thin-layer chromatography showed complete disappearance of steroid starting material. The reaction mixture was then poured into ice water (20 ml) and the product extracted with ethyl acetate (20 ml), and the extract washed with aqueous 1N HCl (5 ml) and water (5 ml). After drying the ethyl acetate solution over anhydrous sodium sulfate, the product was treated with activated charcoal (200 mg) and crystallized from a mixture of ethyl acetate and hexane. The hemisuccinate esters were prepared as described above, except that succinic anhydride (225 mg) was used in place of glutaric anhydride, and the reaction required 7 days for completion at room temperature.

Steroids were initially dissolved in 100% DMSO, then diluted into assay buffer at a final DMSO concentration of 0.5% and sonicated for 20 min. All other solutions also contained 0.5% DMSO. Except where otherwise noted, the final steroid concentration was 100 μM. 3α5β and pregnenolone were used at 50 μM and 20 μM, respectively, as higher concentrations tended to precipitate in the assay buffer.

Cell Culture

Principally neuronal cultures were prepared from hippocampal tissue of fetal Sprague-Dawley rats on day 18 of embryonic development, as previously described (Brewer et al., *Brain Research* 494: 65–74 (1989)). Briefly, hippocampal cells were dissociated by trituration in $Ca^{2+}/Mg^{2+}$-free Hank's basic salt solution (Gibco) supplemented with 4.2 mM bicarbonate, 1 mM sodium pyruvate, 20 mM HEPES, 3 mg/ml bovine serum albumin (BSA). Dissociated cells were then pelleted by centrifugation (500×g, 4 min). The resulting pellet was suspended in Dulbecco's modified eagle medium (DMEM) (Gibco) supplemented with 2.4 mg/ml BSA, 26.5 mM sodium bicarbonate, 1 mM sodium pyruvate, 20 mM HEPES, 10% fetal bovine serum (FBS) (Gibco), 100 units/ml penicillin, 100 μg/ml streptomycin (Gibco), and a modification of Brewer's B16 defined components (with 250 nM vitamin B12 and without catalase, glutathione, and superoxide dismutase) (Pike et al., *J Neurosci* 13: 1676–1687 (1993)). Cells were then plated onto poly-L-lysine-coated 24-well culture dishes (Nunclon) at a density of 15,000 cell/cm$^2$ and maintained in a humidified atmosphere containing 5% $CO_2$/95% air at 37° C. After 48 h, nonneuronal cell division was inhibited by a 48 h exposure to 1 μM cytosine arabinoside. Cultures were subsequently maintained in serum-free DMEM plus defined components and were used for experiments 16 to 24 days after plating.

Intracellular Calcium Concentration Measurements

NMDA-induced increases in $[Ca^{2+}]_i$ were measured with the $Ca^{2+}$-sensitive fluorescent dye Fluo-3, AM (Molecular Probes) and a Cytofluor 2350 (Perceptive Biosystems) fluorescence plate reader, using excitation and emission filters of 485 nm and 530 nm, respectively. Hippocampal neurons were loaded with dye by incubating cultures with 10 μM Fluo-3, AM and 0.05% (w/v) Pluronic F-127 (Molecular Probes), a nonionic detergent, for 2 hours at 37° C. Fluo-3, AM and Pluronic F-127 were dissolved in dimethyl sulfoxide (DMSO, final concentration 0.5%). Cultures were then washed 3 times with assay buffer (120 mM NaCl, 5.4 mM KCl, 1.8 mM $CaCl_2$, 15 mM glucose, 25 mM Tris HCl, 0.5 μM tetrodotoxin; pH 7.4) to remove excess dye. For the purposes of calibration, other plate wells were rinsed instead with assay buffer in which 1.8 mM $MnCl_2$ replaced 1.8 mM $CaCl_2$ ($F_{min}$ buffer) Intracellular free calcium concentrations were calculated using the equation: $[Ca^{2+}]_i = K_D[F-F_{min}]/[F_{max}-F]$, where F is the fluorescence measured, $F_{min}$ is the fluorescence in the absence of calcium (determined in $F_{min}$ buffer after the addition of 10 μM of the $Ca^{2+}$ ionophore A-23187), $F_{max}$ is the fluorescence of the $Ca^{2+}$-saturated dye (determined in assay buffer after the addition of 10 μM A-23187), and $K_D$=320 nM (the equilibrium dissociation constant for the binding of $Ca^{2+}$ to Fluo-3, AM). Fluorescence measurements were made before and 40 s after the addition of NMDA. Steroid or vehicle (0.5% DMSO) was added 10 min prior to the addition of NMDA. NMDA was dissolved in DMEM; steroids and A-23187 were dissolved in DMSO. DMSO was also added to controls to maintain a constant final DMSO concentration of 0.5. Data are expressed as the percentage change in the NMDA-induced increase in $[Ca^{2+}]_i$ in the presence of the indicated steroid. None of the steroids tested significantly altered $[Ca^{2+}]_i$ in the absence of NMDA.

NMDA-Induced Cell Death

Primary cultures of rat hippocampal neurons were exposed to NMDA (dissolved in DMEM) for 15 min (acute exposure) or 16 hours (chronic exposure). In acute exposure experiments, cultures were treated with steroid, MK-801 (Research Biochemicals International; dissolved in DMEM), or vehicle during and/or after NMDA exposure. Steroids were dissolved in DMSO (0.5% final concentration), and all treatment media contained 0.5% DMSO. In chronic exposure experiments, cultures were additionally treated with steroid, vehicle, SR-95531 (Research Biochemicals International; dissolved in DMEM), 6,7-dinitroquinoxaline-2,3-dione (DNQX; Research Biochemicals International; dissolved in DMEM), or MK-801 (dissolved in DMEM) during NMDA exposure. Following exposure, cultures were washed 3 times with medium from sister cultures (conditioned medium). After the final wash, steroid or vehicle was reintroduced. Drugs were added to cultures in 25 μl of conditioned medium to yield a final volume of 0.25 ml per well. Except where otherwise noted, final steroid concentration was 100 μM. 3α5β and pregnenolone were used at 50 μM and 20 μM, respectively, as higher concentrations tended to precipitate in the culture medium.

The ability of neurons to exclude trypan blue was used to quantitate cell viability (Dawson et al., *Proc Natl Acad Sci USA* 88: 6368–6371 (1991)). 24 hours after acute and 16 hours after chronic exposure to NMDA, culture medium was replaced by 0.4% trypan blue in 0.1 M phosphate-buffered saline (PBS; pH 7.4) and placed in a humidified incubator for 10 min. Cultures were then fixed with 4% paraformaldehyde in PBS for 30 min, at whichtime the fixative was replaced with PBS. The number of stained and unstained neurons were counted in 4 high-power fields per culture well, using an inverted phase contrast microscope under both bright field and phase contrast settings. Experiments were performed in triplicate, and all assessments were made with the experimenter blind to the treatment of each culture well. Percent cell death is expressed as follows: (number of trypan blue stained neurons)/(total number of neurons)× 100%. The basal level of neuronal death (termed background), measured in controls lacking NMDA and PS, was 0–10%, and was subtracted from the raw data in each experiment.

Oocyte Electrophysiology $NR1_{100}$ (NR1G) and NR2A clones were kindly provided by Dr. R. S. Zukin (Albert Einstein College of Medicine, New York, N.Y.) and Dr. S. Nakanishi (Faculty of Medicine, Kyoto University, Kyoto, Japan), respectively. mRNA was prepared through in vitro transcription of $NR1_{100}$ and NR2A cDNAs using the mMessage mMachine kit (Ambion, Tex.). On the day following isolation, batches of 20–40 selected *Xenopus oocytes* were injected with 50 nl of prepared RNA solution (0.5 ng $NR1_{100}$ and 5 ng of NR2A mRNA/*oocyte*). *Oocytes* were maintained in glass petri dishes containing Barth's solution (84 mM NaCl, 1 mM KCl, 2.4 mM $NaHCO_3$, 0.82 mM $MgSO_4$, 0.41 mM $CaCl_2$, 0.33 mM Ca(NO3)2, 2.5 mM pyruvate, 0.1 mg/ml gentamycin, 7.5 mM Tris/HCl, pH 7.4) in an incubator at 18° C. *Oocytes* were used for electrophysiological experiments 4–10 days after injection.

Recordings from *oocytes* were obtained using the two electrode voltage-clamp mode with an Axoclamp-2A amplifier (Axon Instruments). The resistance of microelectrodes, pulled from glass capillaries and filled with 3 M KCl solution, was 2.5–3.5 M. Membrane potential was clamped at –70 mV. Drugs were applied by a gravity-driven external perfusion system. Drug application and data acquisition were carried out with custom-written software implemented in the SuperScopeII programming language (GW Instruments, Somerville, Mass.). Membrane current was filtered at 500 Hz and sampled at 100 Hz.

Statistical Analysis

The degree of modulation of NMDA-induced $Ca^{2+}$ influx, cell death, and currents is expressed as the percent change, defined as (I'/I–1)×100%, where I and I' are the NMDA-induced responses in the absence and presence of modulator, respectively. All data are expressed as mean±standard error of the mean. Statistical significance was evaluated using 95% confidence limits unless otherwise noted.

EXAMPLE 3

Figure 11:
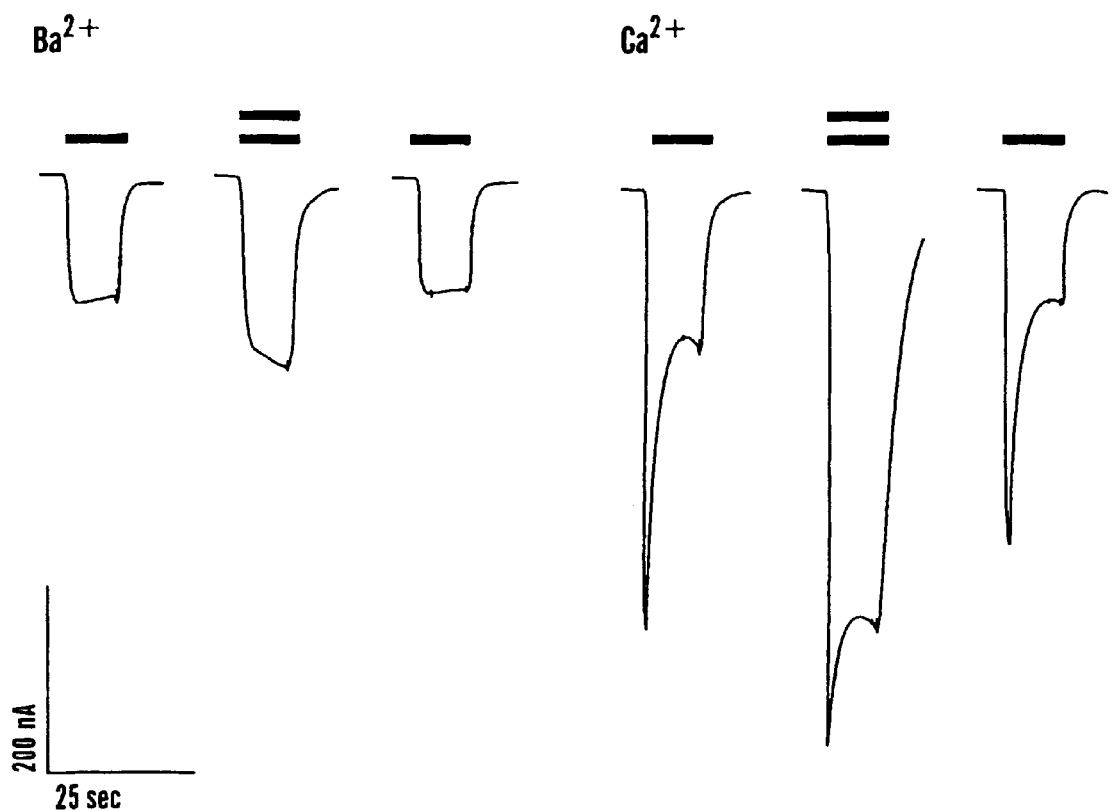
FIG. 11 is a representation of current recordings obtained from an *oocytes* bathed in solutions containing either Ba$^{2+}$ or Ca$^{2+}$ ions. The current responses were induced by co-application of 10 mM glycine and 80 mM NMDA (single bars). Double bars indicate the co-application of 100 mM PS in addition to NMDA and glycine.

FIG. 11 shows a comparison of traces of NMDA induced responses obtained from *oocytes* expressing $NR1_{100}$/NR2A receptors bathed in normal ($Ca^{2+}$ containing) Ringer solution and Ba-Ringer solution in which $Ca^{2+}$ was replaced with $Ba^{2+}$. Current traces obtained in Ba-Ringer solution do not exhibit the rapidly inactivating component that is seen in normal Ringer, and which most likely reflects current through $Ca^{2+}$ activated $Cl^-$ channels (Leonard et al., *Neuron* 4: 53–60 (1990)). All further experiments were performed in Ba-Ringer. The current responses obtained from *oocytes* injected with NMDA receptors composed of different NR1 isoforms differed from each other in agonist $EC_{50}$s. L-glutamate, glycine and NMDA $EC_{50}$s for NR1 isoforms lacking N-terminal insert were less than ones for isoforms with N-terminal insert (except for $NR1_{001}$, see Table 2). The absolute current responses induced by saturating concentration of agonists (500 mM NMDA and 10 mM glycine) were in the range from 800 to 1800 nA. Since a steroid's effect on NMDA receptors was found to depend on level of expression of the receptor in the membrane of *oocytes* (see below), *oocytes* that showed current responses in the range of 0.1 $\mu$Amp to 1 $\mu$Amp induced by 50 mM (or 80 mM NMDA for isoforms with N-terminal insert) and 10 mM glycine were used to assess the effects of pregnenolone sulfate and pregnanolone sulfate on NMDA receptors comprised of different isoforms of NR1 subunit.

Co-application of 100 mM PS resulted in potentiation of current through NMDA receptors comprising any NR1 isoform. NMDA, L-glutamate and glycine dose-response experiments showed that potentiation by PS was observed even at saturating concentrations of agonists. In addition, the agonists $EC_{50}$ obtained in the absence of steroid were similar to ones obtained in the presence of 100 mM PS, suggesting that PS did not compete for the agonists binding sites (see Table 2).

TABLE 2

Properties of NMDA receptors comprising different NR1 isoforms in the absence and in the presence of 100 mM PS.

| Subunits | $EC_{50}$, mM | | $n_{Hill}$ | $E_{max}$ |
|---|---|---|---|---|
| | NMDA (PS) | | | |
| $NR1_{011}$/NR2A | 52 ± 6.5 | (43 ± 4.8) | 1.39 ± 0.07 (1.11 ± 0.12) | 1.14 ± 0.02 |
| (1.68 ± 0.06) | n = 4 | (n = 4) | | |
| $NR1_{111}$/NR2A | 88 ± 16 | (95 ± 12) | 1.49 ± 0.02 (1.33 ± 0.22) | 1.34 ± 0.09 |
| (2.27 ± 0.07) | n = 4 | (n = 4) | | |
| $NR1_{001}$/NR2A | 81 ± 7 | (71 ± 18) | 1.46 ± 0.07 (1.21 ± 0.15) | 1.27 ± 0.04 |
| (2.15 ± 0.17) | n = 8 | (n = 4) | | |
| $NR1_{010}$/NR2A | 44 ± 8 | (22 ± 2) | 1.19 ± 0.06 (1.13 ± 0.09) | 1.18 ± 0.03 |
| (1.53 ± 0.08) | n = 7 | (n = 4) | | |
| $NR1_{000}$/NR2A | 60 ± 7 | (33 ± 3) | 1.31 ± 0.08 (1.18 ± 0.05) | 1.20 ± 0.05 |
| (1.55 ± 0.04) | n = 7 | (n = 11) | | |
| $NR1_{101}$/NR2A | 75 ± 6 | (35 ± 5) | 1.31 ± 0.05 (1.15 ± 0.12) | 1.33 ± 0.07 |
| (1.78 ± 0.06) | n = 5 | (n = 4) | | |
| $NR1_{100}$/NR2A | 76 ± 6.2 | (40 ± 3.3) | 1.13 ± 0.04 (1.20 ± 0.06) | 1.36 ± 0.04 |
| (1.60 ± 0.07 | n = 11 | (n = 6) | | |
| | L-glutamate (PS) | | | |
| $NR1_{011}$/NR2A | 0.56 ± 0.03 | (0.39 ± 0.03) | 1.17 ± 0.03 (1.13 ± 0.08) | 1.59 ± 0.03 (2.08 ± 0.21) |
| | n = 4 | (n = 4) | | |
| $NR1_{111}$/NR2A | 0.71 ± 0.06 | (0.51 ± 0.03) | 1.39 ± 0.02 (1.58 ± 0.09) | 1.87 ± 0.12 (2.62 ± 0.27) |
| | n = 4 | (n = 4) | | |
| $NR1_{001}$/NR2A | 1.03 ± 0.09 | (0.65 ± 0.21) | 1.20 ± 0.07 (1.57 ± 0.18) | 2.10 ± 0.12 (2.85 ± .26) |
| | n = 7 | (n = 4) | | |
| $NR1_{010}$/NR2A | 0.38 ± 0.04 | (0.25 ± 0.01) | 1.32 ± 0.14 (1.59 ± 0.15) | 1.48 ± 0.03 (1.81 ± 0.08) |
| | n = 9 | (n = 4) | | |
| $NR1_{000}$/NR2A | 0.65 ± 0.03 | (0.59 ± 0.04) | 1.05 ± 0.02 (1.17 ± 0.08) | 1.75 ± 0.02 (2.92 ± 0.03) |
| | n = 4 | (n = 4) | | |
| $NR1_{101}$/NR2A | 0.68 ± 0.06 | (0.60 ± 0.04) | 1.07 ± 0.06 (1.37 ± 0.06) | 1.77 ± 0.09 (2.72 ± 0.07) |
| | n = 3 | (n = 4) | | |
| $NR1_{100}$/NR2A | 0.45 ± 0.02 | (0.31 ± 0.02) | 1.15 ± 0.04 (0.98 ± 0.06) | 1.50 ± 0.04 (2.30 ± 0.21) |
| | n = 4 | (n = 4) | | |
| | glycine (PS) | | | |
| $NR1_{011}$/NR2A | 0.92 ± 0.11 | (0.85 ± 0.1) | 1.30 ± 0.05 (1.34 ± 0.18) | 1.67 ± 0.08 (2.24 ± 0.29) |
| | n = 4 | (n = 3) | | |
| $NR1_{111}$/NR2A | 1.22 ± 0.09 | (1.07 ± 0.09) | 1.49 ± 0.06 (1.26 ± 0.10) | 1.93 ± 0.07 (2.68 ± 0.16) |
| | n = 4 | (n = 8) | | |
| $NR1_{001}$/NR2A | 1.79 ± 0.3 | (1.56 ± 0.65) | 1.25 ± 0.07 (1.30 ± 0.13) | 1.89 ± 0.20 (2.77 ± 0.40) |
| | n = 6 | (n = 4) | | |
| $NR1_{010}$/NR2A | 0.90 ± 0.08 | (1.07 ± 0.11) | 1.32 ± 0.07 (1.38 ± 0.10) | 1.51 ± 0.07 (1.92 ± 0.19) |
| | n = 4 | (n = 4) | | |
| $NR1_{000}$/NR2A | 0.97 ± 0.10 | (1.46 ± 0.17) | 0.90 ± 0.01 (1.12 ± 0.05) | 1.48 ± 0.04 (2.88 ± 0.27) |
| | n = 3 | (n = 4) | | |
| $NR1_{101}$/NR2A | 1.74 ± 0.26 | (1.07 ± 0.17) | 1.37 ± 0.13 (1.32 ± 0.09) | 1.63 ± 0.04 (2.46 ± 0.23) |
| | n = 5 | (n = 4) | | |
| $NR1_{100}$/NR2A | 0.82 ± 0.11 | (0.97 ± 0.07) | 1.23 ± 0.07 (1.03 ± 0.05) | 1.52 ± 0.07 (2.34 ± 0.09) |
| | n = 4 | (n = 4) | | |

Figure 12A:
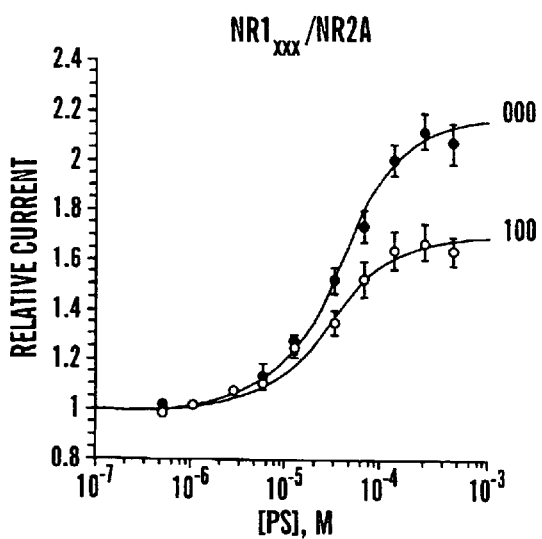
FIG. 12 contains graphical representations of PS dose-responses for NR1/NR2A receptors. Presented are normalized current responses obtained from *oocytes* injected with (A): NR1$_{000}$/NR2A, NR1$_{100}$/NR2A; (B) : NR1$_{001}$/NR2A, NR1$_{101}$/NR2A; (C) : NR1$_{011}$/NR2A, NR1$_{111}$/NR2A mRNAs. The current was induced by coapplication of 10 mM glycine and 50 mM NMDA (for N-terminal insert lacking NR1 isoforms, open symbols) or 80 mM NMDA (for N-terminal insert containing NR1 isoforms, closed symbols) and different concentration of PS. Error bars are S.E.M. Solid lines are drawn using equation 1+E max/(1+(EC$_{50}$/c)n with parameters from Table 3.
Figure 12B:
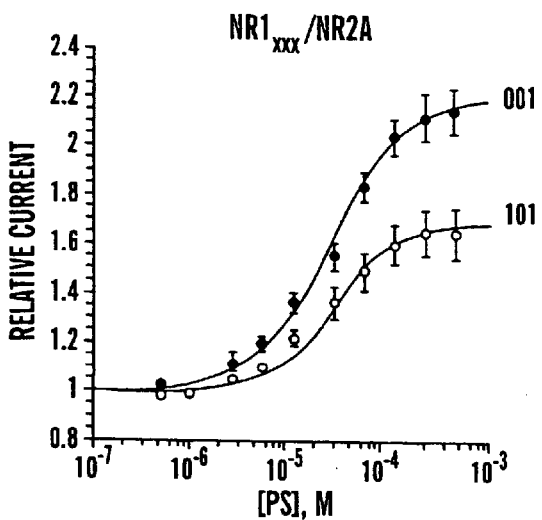
Figure 12C:
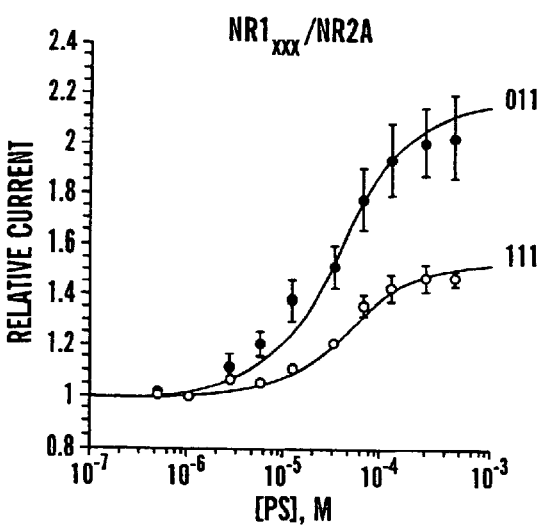

In order to construct PS dose-response curves different concentrations of PS (in the range from 0.5 to 400 mM) were coapplied with 10 mM glycine and 50 mM (or 80 mM NMDA, which is close to $EC_{50}$ values for NR1 isoforms without or with N-terminal insert respectively). The dose-response experiments revealed that PS had similar potency for all combinations of $NR1_{xxx}$ and NR2A subunits. However, PS was more efficient when applied to NMDA receptors containing NR1 isoforms that were lacking N-terminal insert (see FIG. 12). Maximum potentiation of NMDA-induced current for $NR1_{111}/$, $NR1_{101}/$, $NR1_{100}/$ NR2A receptors were 1.51±0.04 (n=9), 1.66±0.10 (n=8), 1.67±0.07 (n=8) fold respectively in comparison to 2.14±0.17 (n=7), 2.19±0.09 (n=9), 2.14±0.08 (n=15) fold potentiation for $NR1_{011}/$, $NR1_{001}/$, $NR1_{000}/$NR2A receptors respectively (see Table 3). T-test analysis of maximum PS potentiation obtained from receptors comprising NR1 isoforms with and without N-terminal insert resulted in p values of 0.024, 0.005, 0.002 for pairs 111 vs. 011, 101 vs. 001 and 100 vs. 000 respectively.

TABLE 3

Effect of PS on NMDA receptors comprising different NR1 isoforms.

|  | $EC_{50}$, mM |  | $n_{Hill}$ | $E_{max}$ |
| --- | --- | --- | --- | --- |
| $NR1_{111}$/NR2A | 40 ± 8 | (n = 9) | 1.28 ± 0.19 | 0.51 ± 0.04 |
| $NR1_{011}$/NR2A | 32 ± 8 | (n = 7) | 1.18 ± 0.18 | 1.14 ± 0.17 |
| $NR1_{101}$/NR2A | 25 ± 5 | (n = 8) | 1.52 ± 0.24 | 0.66 ± 0.10 |
| $NR1_{001}$/NR2A | 26 ± 2 | (n = 9) | 1.14 ± 0.10 | 1.19 ± 0.09 |
| $NR1_{100}$/NR2A | 24 ± 5 | (n = 8) | 1.33 ± 0.08 | 0.67 ± 0.07 |
| $NR1_{000}$/NR2A | 29 ± 3 | (n = 15) | 1.31 ± 0.06 | 1.14 ± 0.08 |
| $NR1_{010}$/NR2A | 48 ± 12 | (n = 5) | 1.30 ± 0.18 | 1.03 ± 0.09 |
| $NR1_{111}$/NR2B | 24 ± 1 | (n = 3) | 1.52 ± 0.10 | 1.20 ± 0.10 |
| $NR1_{011}$/NR2B | 35 ± 10 | (n = 4) | 1.29 ± 0.19 | 0.78 ± 0.14 |
| $NR1_{101}$/NR2B | 32 ± 8 | (n = 2) | 1.63 ± 0.29 | 1.03 ± 0.02 |
| $NR1_{001}$/NR2B | 24 ± 6 | (n = 4) | 1.34 ± 0.17 | 0.63 ± 0.07 |
| $NR1_{100}$/NR2B | 34 ± 4 | (n = 4) | 1.42 ± 0.11 | 1.02 ± 0.10 |
| $NR1_{000}$/NR2B | 22 ± 7 | (n = 4) | 1.52 ± 0.15 | 0.58 ± 0.04 |

Figure 13A:
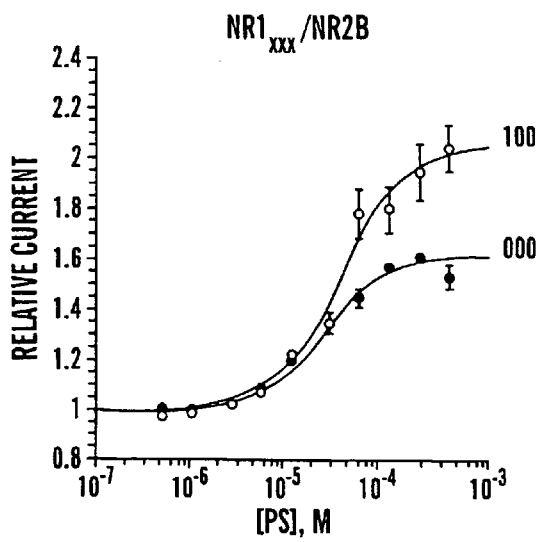
FIG. 13 contains graphical representations of data which compares 3α5βS and PS dose-responses for NR1/NR2A receptors. Presented are normalized current responses obtained from *oocytes* injected with NR1$_{XXX}$/NR2A mRNAs. The current was induced by coapplication of 10 mM glycine and 50 mM NMDA (for N-terminal insert lacking NR1 isoforms, open symbols) or 80 mM (in B; 100 mM in A) NMDA (for N-terminal insert containing NR1 isoforms, closed symbols) and different concentration of 3a5bS (A) or PS (B). Error bars are S.E.M. Solid lines are drawn using equation 1+E max/(1+(EC$_{50}$/c)$_n$ with parameters from Table 2 and 3.
Figure 13B:
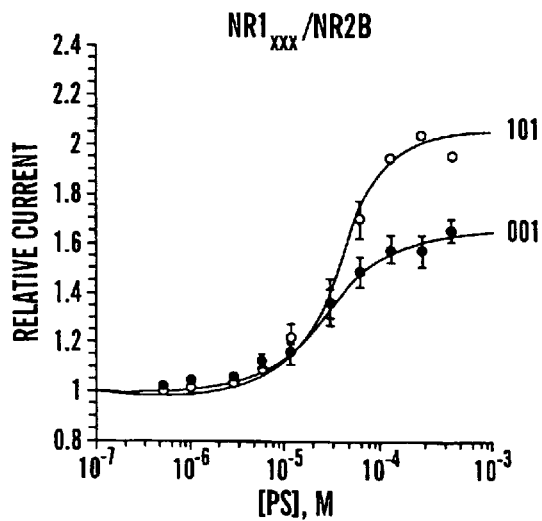
Figure 13C:
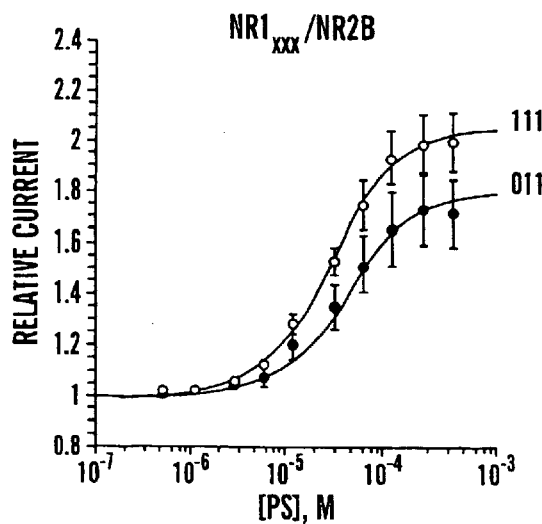

In contrast to potentiating effect of PS, $3\alpha5\beta S$ induced current inhibition through receptors comprising any NR1 isoform (see FIG. 13). The inhibitory effect was reversible and concentration dependent. The potency of $3\alpha5\beta S$ obtained for NMDA receptors comprising different NR1 isoforms were similar, revealing PS $EC_{50}$s that ranged from 25 to 45 mM. The maximum extent of inhibition obtained for different NR1 isoforms ranged from 75±7% (for $NR1_{111}/$ NR2A) to 99±3% (for $NR1_{100}/$NR2A, see Table 4). The differences in maximum inhibition were insignificant and no apparent correlation with the presence of N-terminal insert was observed.

TABLE 4

Effect of $3\alpha5\beta S$ on NMDA receptors comprising different NR1 isoforms.

| Splice variant | $EC_{50}$, mM |  | $n_{Hill}$ | $E_{max}$ |
| --- | --- | --- | --- | --- |
| 111 | 29 ± 5 | (n = 4) | 1.09 ± 0.9 | −0.75 ± 0.07 |
| 011 | 38 ± 0.5 | (n = 4) | 0.96 ± 0.06 | −0.86 ± 0.04 |
| 101 | 45 ± 2 | (n = 3) | 1.05 ± 0.25 | −0.90 ± 0.07 |
| 001 | 25 ± 2 | (n = 4) | 0.95 ± 0.11 | −0.89 ± 0.05 |
| 100 | 36 ± 2 | (n = 4) | 0.83 ± 0.02 | −0.99 ± 0.03 |
| 000 | 41 ± 0.6 | (n = 4) | 0.98 ± .03 | −0.89 ± 0.01 |
| 010 | 34 ± 4 | (n = 4) | 1.04 ± 0.06 | −0.85 ± 0.02 |

EXAMPLE 4

Figure 15A:
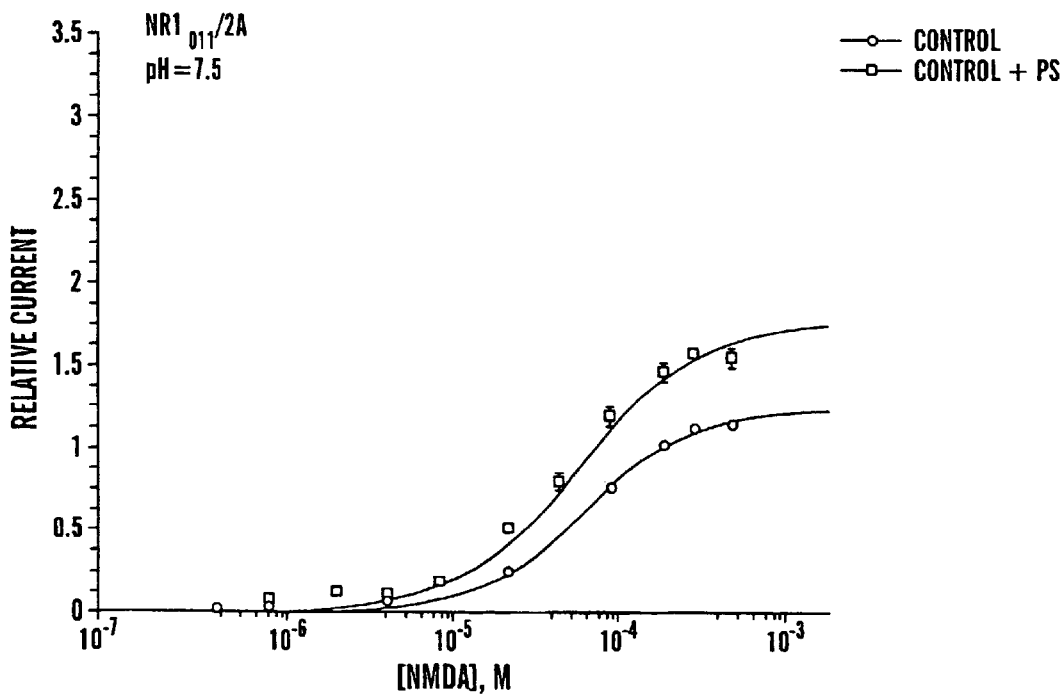
FIG. 15 contains two graphs of data indicating PS differentially modulates NR1$_{011}$/2A and NR1$_{111}$/2A splice variants at pH 7.5. Data points are averaged normalized peak NMDA-induced current responses obtained from *oocytes* injected with (A) NR1$_{011}$/2A or (B) NR1$_{111}$/2A mRNAs. Concentration-response data for NMDA (circles) and for NMDA+100 μM PS (squares) were obtained in the presence of 10 μM glycine. Fitted parameters are (A) (control ○, n=14), EC$_{50}$=71 μM, Emax=1.20, n$_H$=1.47; (+PS open squares, n=14), EC$_{50}$=67 μM, Emax=1.79, n$_H$=1.24; (B) (control closed circles, n=14), EC$_{50}$=103 μM, Emax=1.33, n$_H$=1.67; (+PS closed squares, n=22), EC$_{50}$=89 μM, Emax= 2.70, n$_H$=2.02. The data were normalized relative to the current induced by co-application of 200 μM NMDA and 10 μM glycine to the same *oocyte*. Error bars represent S.E.M.
Figure 15B:
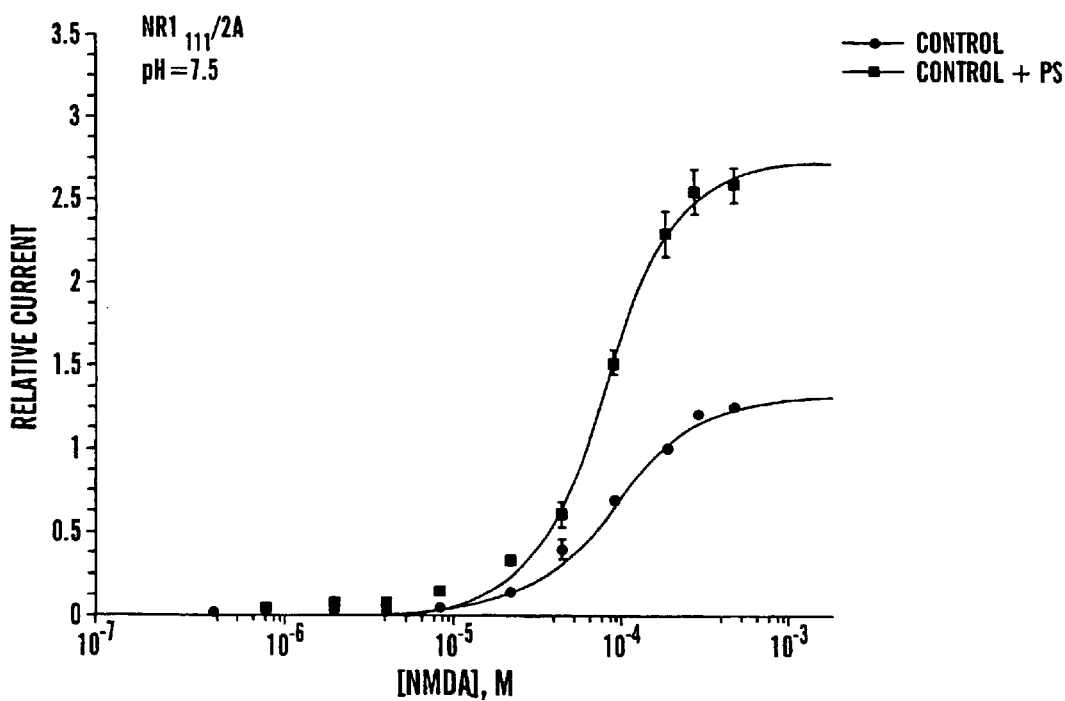

Differential Modulation of $NR1_{xxx}$/NR2A Splice Variants by Neuroactive Steroids Table 5 below shows alternatively spliced exons present in each NR1 splice variant. In order to assess the modulatory role or pregnenolone sulfate (PS) on NMDA receptor composed of different $NR1_{xxx}$ subunits, NMDA dose response of $NR1_{001}$/NR2A and $NR1_{111}$/NR2A splice variants were determined, in the presence or absence of 100 μM PS (FIG. 15). The extrapolated maxima (Emax) obtained from the concentration-response data (fitted by the non-linear regression logistic equation: relative current=$Emax/1+(EC_{50}/c)^{nH}$), indicate that the relative current change is splice variant dependent. The Emax obtained for $NR1_{011}$/NR2A in the presence of absence of PS was 1.79 and 1.2 respectively, while for $NR1_{111}$/NR2A was 2.7 and 1.33. The change in the efficacy was not only significant relative to control but was also between the splice variants (*p<0.0000005), while the $EC_{50}$s and thus the potency remained unchanged (for $NR1_{011}$/NR2A $EC_{50}$=71 μM, $EC_{50}$(+PS)=67 μM and for $NR1_{111}$/NR2A $EC_{50}$=103 μM, $EC_{50}$(+PS)=89 μM)

Figure 16A:
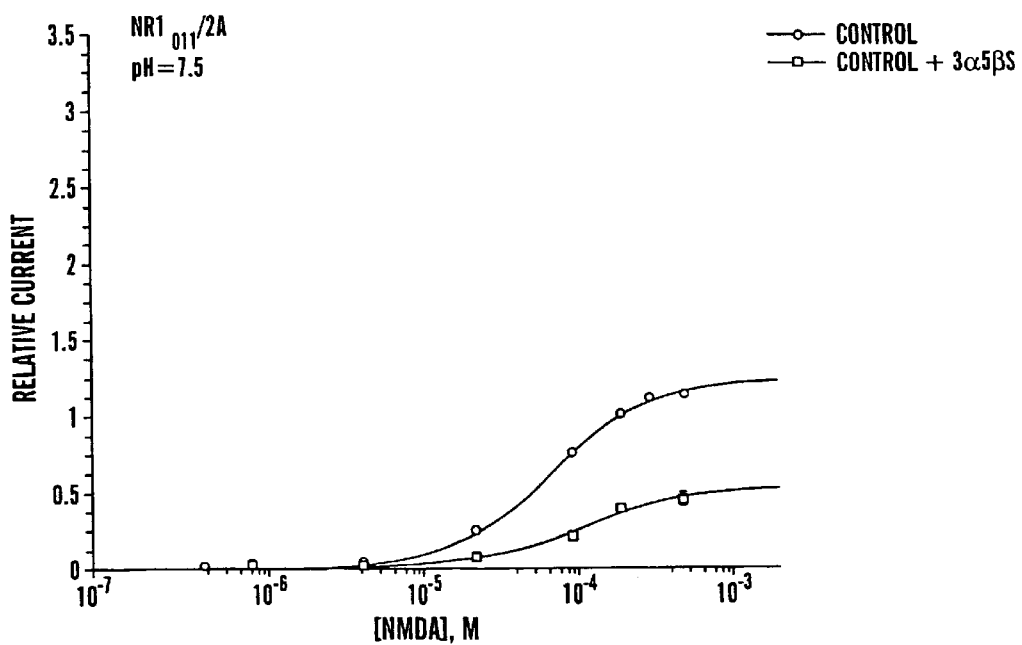
FIG. 16 contains two graphs of data indicating 3α5βS proportionately modulates $NR1_{011}/2A$ and $NR1_{111}/2A$ splice variants at pH 7.5. Data points are averaged normalized peak NMDA-induced current responses obtained from *oocytes* injected with (A) $NR1_{011}/2A$ or (B) $NR1_{111}/2A$ mRNAs. Concentration-response data for NMDA (circles) and for NMDA+100 μM PS (squares) were obtained in the presence of 10 μM glycine. Fitted parameters are (A) (control ○, n =14), $EC_{50}$=7I μM, Emax =1.20, $n_H$=1.47; (+3α5βS open squares, n=6), $EC_{50}$=120 μM, Emax=0.52, $n_H$=1.35; (B) (control, closed circle, n=14), $EC_{50}$=103 μM, Emax=1.33, $n_H$=1.67; (+3α5βS, closed squares, n=8), $EC_{50}$=158 μM, Emax=0.54, $n_H$=1.50. The data were normalized relative to the current induced by co-application of 200 μM NMDA and 10 μM glycine to the same *oocyte*. Error bars represent S.E.M.
Figure 16B:
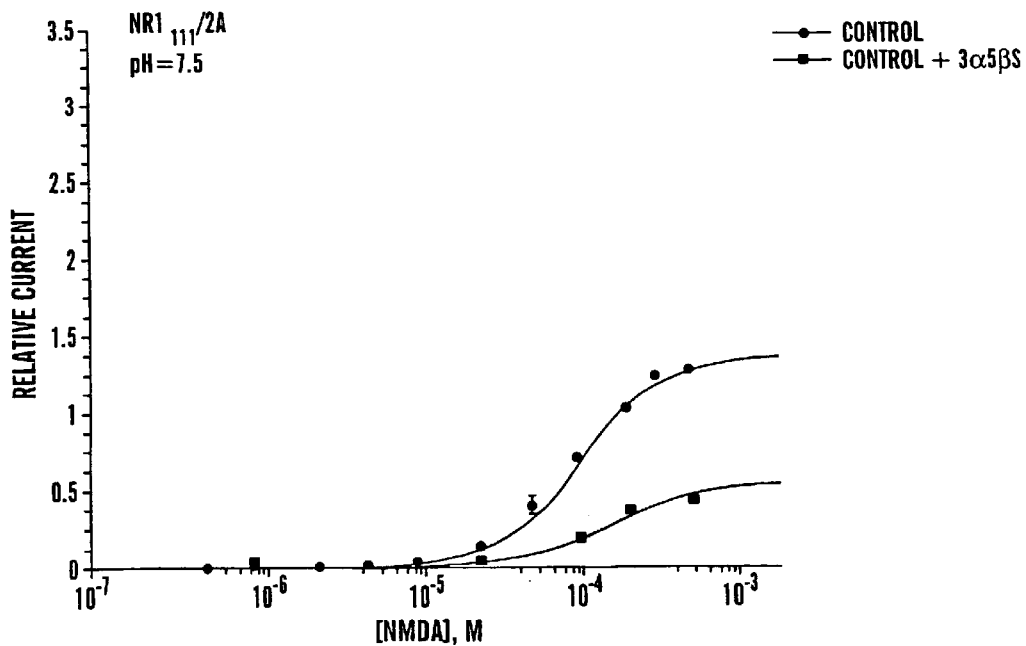

To further elucidate the role of neuroactive steroids on $NR1_{xxx}$/NR2A splice variants, dose response was determined in the presence or absence of 100 μM pregnanolone sulfate ($3\alpha5\beta S$) (FIG. 16). The acquired data indicate that the extrapolated maxima of the relative current change are independent of the splice variant. The Emax obtained for $NR1_{011}$/NR2A in the presence or absence of $3\alpha5\beta S$ was 0.52 and 1.2 respectively, while for $NR1_{111}$/NR2A was 0.54 and 1.33. While the observed change in the efficacy was not significant (p>0.05), the potency relative to control, was decreased by 69% for NR1011/NR2A and 53% for $NR1_{111}/$NR2A, as indicated by the $EC_{50}$s (for $NR1_{111}$/NR2A $EC_{50}$= 71 μM, $EC_{50}$(+$3\alpha5\beta S$)=120 μM and for $NR1_{111}$/NR2A $EC_{50}$=103 μM, $EC_{50}$(+$3\alpha5\beta S$)=158 μM).

Figure 17A:
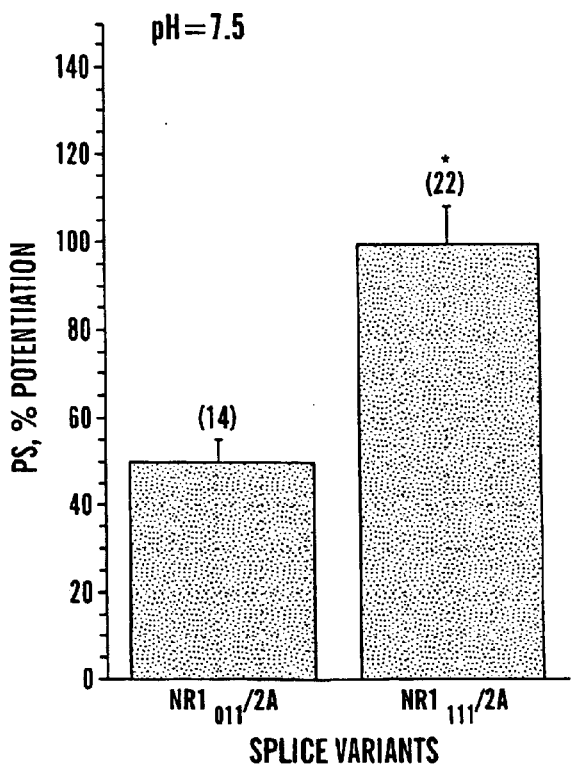
FIG. 17 contains bar graphs of data indicating neuroactive steroid modulation of $NR1_{011}/2A$ and $NR1_{111}/2A$ splice variants at pH 7.5. Bars indicate (A) the percentage potentiation of the maximum NMDA response by 100 μM PS for $NR1_{111}/2A$ (50%) and on $NR1_{111}/2A$ (103%; *p<5×10$^{-7}$) receptors and (B) the percentage inhibition of the maximum NMDA response by 100 μM 3α5βS for $NR1_{011}/2A$ (56%) and $NR1_{111}/2A$ (59%; p>0.05) receptors. Dose-response data (from the same *oocytes* as in FIGS. 15 and 16) were individually fitted to the logistic equation to determine the maximum NMDA response. Bars depict the average potentiation/inhibition of the maximum NMDA response for the number of *oocytes* given in parentheses. Error bars represent S.E.M.
Figure 17B:
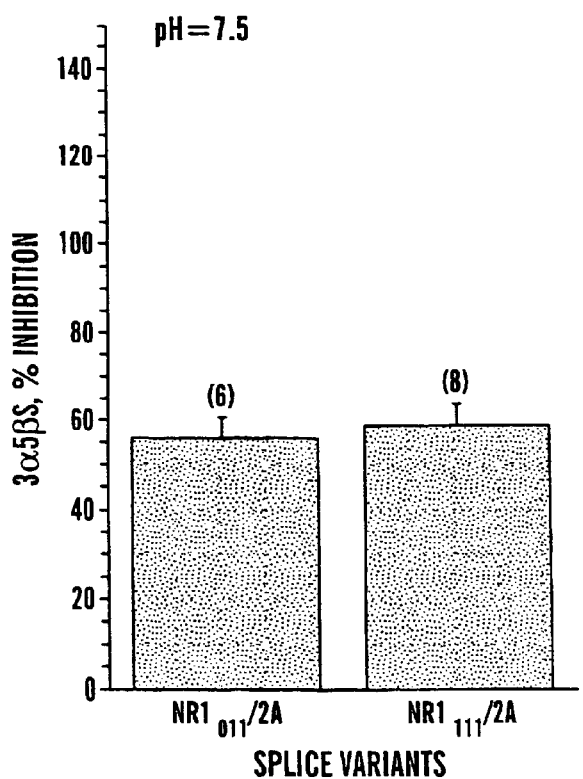

In summary (FIG. 17), the percentage potentiation of 100 μM PS on $NR1_{011}$/NR2A was 50% and on $NR1_{111}$/NR2A was 103% suggesting a difference of 106% between them (*p<0.0000005), while 100 μM of $3\alpha5\beta S$ gave 56% and 59% inhibition for $NR1_{011}$/NR2A and $NR1_{111}$/NR2A respective suggesting a difference of 5% (p>0.05).

Figure 18:
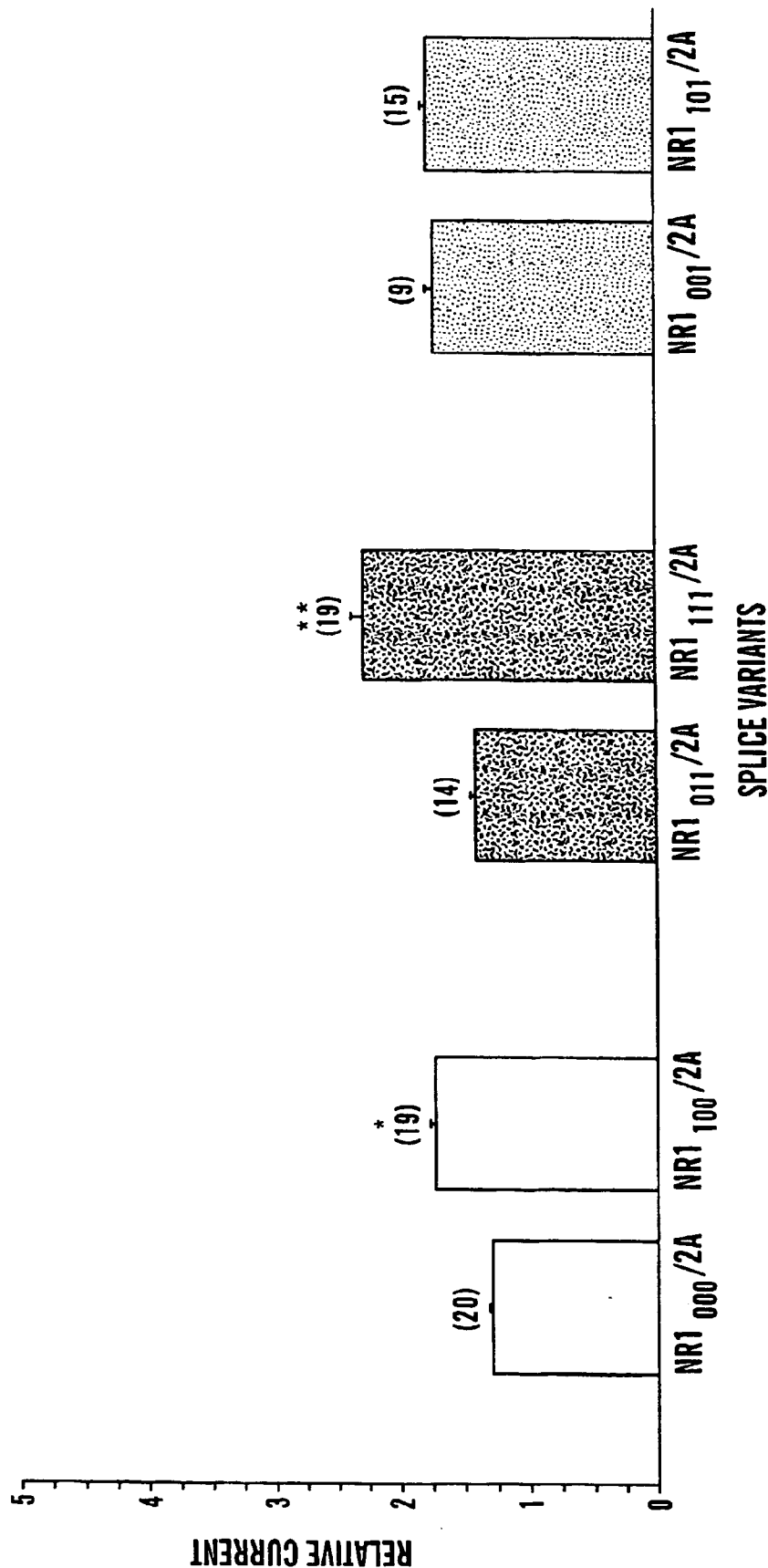
FIG. 18 is a bar graph of data indicating PS induced modulation is $NR1_{XXX}$ splice variant dependent. A summary chart is shown which illustrates the PS induced increase in the 200 μM NMDA+10 μM glycine current, expressed relative to the NMDA induced current in the absence of PS (maximum relative current; MRC); (for $NR1_{000}/2A$ MRC=1.29, for $NR1_{100}/2A$ MRC=1.73, for $NR1_{011}/2A$ MRC=1.41, for $NR1_{111}/2A$ MRC=2.28, for $NR1_{001}/2A$ MRC=1.72, and for $NR1_{101}/2A$ MRC=1.78). Error bars represent S.E.M. The number of *oocytes* tested is listed in parentheses. (Significance is indicated by *p: p<5×10$^{-6}$, **: p<5×10$^{-7}$)

To further test the hypothesis that the presence or absence of the α exon (a 21 amino acid insert) controls the modulatory effect of PS on different $NR1_{xxx}$/NR2A splice variatns, the data obtained from the max relative currents (mrc) after co-application of 200 μM NMDA+10 μM glycine±100 μM PS were compared (FIG. 18). The data indicate a 1.3-fold difference between $NR1_{000}$/NR2A (mrc= 1.29) and $NR1_{100}$/NR2A (mrc=1.73), (*p<0.0000005), a 1.6-fold difference between $NR1_{011}$/NR2A (mrc=1.41) and $NR1_{111}$/NR2A (mrc=2.28), (p<0.0000005) and significantly no difference between $NR1_{001}$/NR2A (mrc=1.73) and $NR1_{101}$/NR2A (mrc=1.78), (p>0.05). These results indicate that specificity of PS induced modulation is $NR1_{xxx}$ subunit dependent.

TABLE 5

|  | EXON PRESENT | | |
| --- | --- | --- | --- |
| SPLICE VARIANT | α | β | γ |
| $NR1_{000}$ | − | − | − |
| $NR1_{001}$ | − | − | + |
| $NR1_{010}$ | − | + | − |
| $NR1_{011}$ | − | + | + |
| $NR1_{100}$ | + | − | − |
| $NR1_{101}$ | + | − | + |
| $NR1_{110}$ | + | + | − |
| $NR1_{111}$ | + | + | + |

Figure 19A:
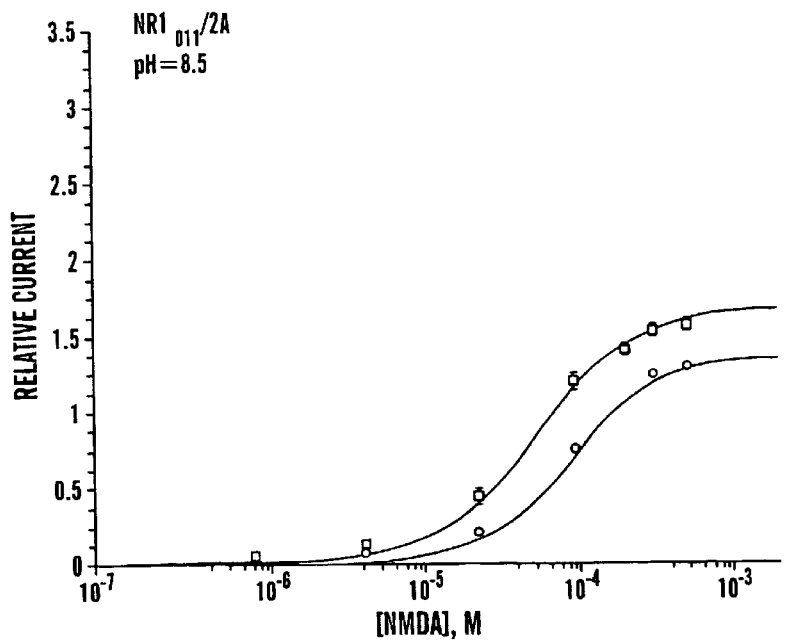
FIG. 19 contains two graphs of data indicating pregnenolone sulfate (PS) differentially modulate $NR1_{011}/2A$ and $NR1_{111}/2A$ splice variants at pH 8.5. Data points are averaged normalized peak NMDA-induced current responses obtained from *oocytes* injected with (A) $NR1_{011}/2A$ or (B) $NR1_{111}/2A$ mRNAs. Concentration-response data for NMDA (circles) and for NMDA+100 μM PS (squares) were obtained in the presence of 10 μM glycine. Fitted parameters are (A) (control ○, n=11), $EC_{50}$=94 μM, Emax= 1.30, $n_H$=1.62; (+PS, open squares, n=10), $EC_{50}$=58 μM, Emax=1.62, $n_H$=1.44; (B) (control, closed circles, n=10), $EC_{50}$=110 μM, Emax=1.35, $n_H$=1.93; (+PS, closed squares, n=23), $EC_{50}$=94 μM, Emax=1.98, $n_H$=1.82. The data were normalized relative to the current induced by co-application of 200 μM NMDA and 10 μM glycine to the same *oocyte*. Error bars represent S.E.M.
Figure 19B:
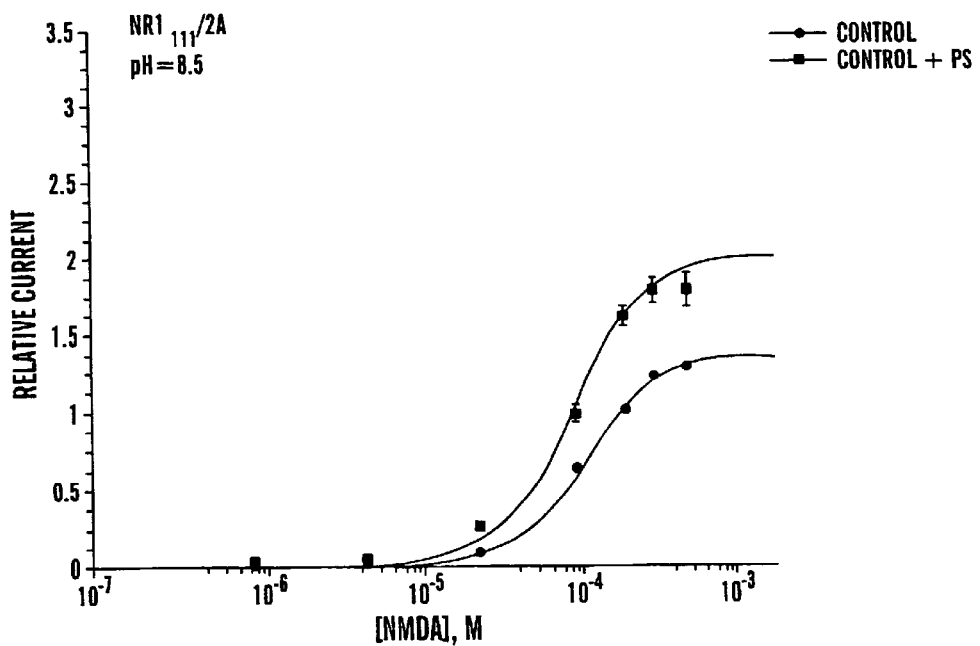
Figure 20A:
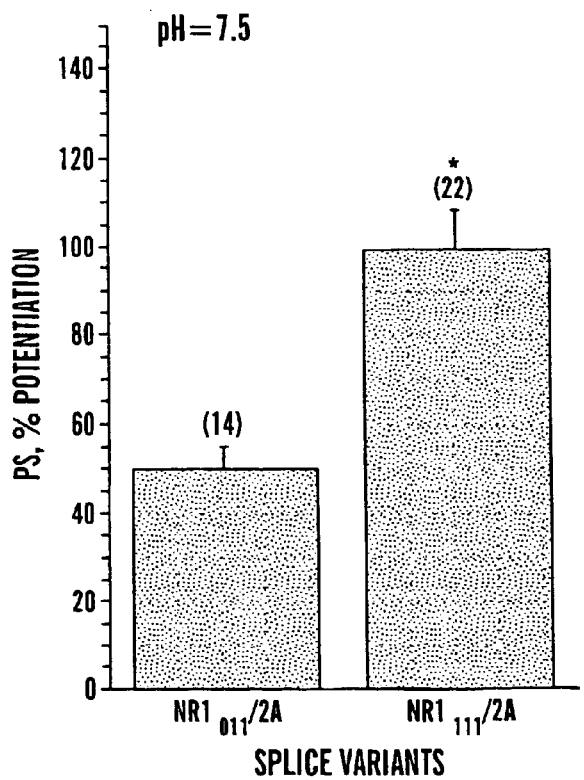
FIG. 20 contains bar graphs of data which indicate PS differentially induced modulation of $NR1_{011}/2A$ and $NR1_{111}/2A$ splice variants at pH 7.5 and 8.5. Bars indicate (A) the percentage potentiation of the maximum NMDA response by 100 μM PS for $NR1_{011}/2A$ (50%) and on $NR1_{111}/2A$ (103%; *p<5×10$^{-7}$) receptors at pH=7.5 and (B) the percentage potentiation of the maximum NMDA response by 100 μM PS for $NR1_{011}/2A$ (24%) and $NR1_{111}/2A$ (47%; *p<0.05) receptors at pH=8.5. Dose-response data (from the same *oocytes* as in FIGS. 15 and 19) were individually fitted to the logistic equation to determine the maximum NMDA response. Bars depict the average potentiation of NMDA response for the number of *oocytes* given in parentheses. Error bars represent S.E.M
Figure 20B:
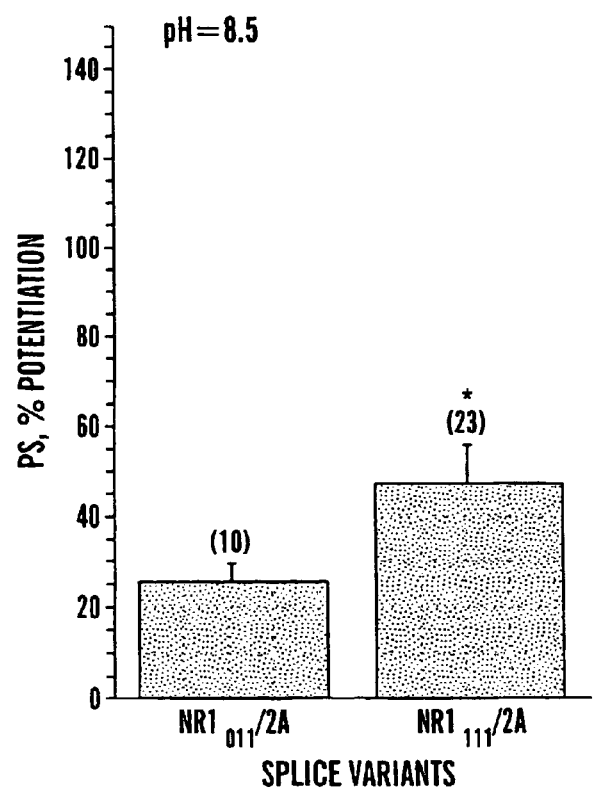

Pregnenolone Sulfate's Differential Modulation of $NR1_{xxx}$/NR2A Splice Variants is pH Dependent In order to assess the effect of hydrogen concentration on the modulatory role of pregnenolone sufate (PS) on NMDA receptors composed of different $NR1_{xxx}$ subunits, NMDA dose response curves of $NR1_{011}$/NR2A and $NR1_{111}$/NR2A splice variants were constructed at pH 8.5, in the presence or absence of 100 µM PS (FIG. 19). The extrapolated maxima (Emax) obtained from the concentration-response, indicate that the relative current change of each splice variant is pH dependent. Although the potency ($EC_{50}$s) for both $NR1_{011}$/NR2A and $NR1_{111}$/NR2A remained the same upon shifting the pH from 7.5 to 8.5, the efficacies of the two splice variants decreased from pH=7.5 to pH=8.5. The Emax obtained for $NR1_{011}$/NR2A in the presence or absence of PS was 1.62 and 1.30 (at pH=8.5) and 1.79 and 1.2 (at pH=7.5) respectively, while for $NR1_{111}$/NR2A was 1.98 and 1.35 (at pH=8.5) and 1.79 and 1.20 (at pH=7.5) respectively. The percentage potentiation of 100 µM PS on $NR1_{011}$/NR2A was 50% and on $NR1_{111}$/NR2A at pH=7.5 was 103% suggesting a difference of 106% between them (*$p<0.0000005$), while 100 µM of PS at pH=8.5 gave 24% and 47% potentiation for $NR1_{011}$/NR2A and $NR1_{111}$/NR2A respectively suggesting a difference of 91% (*$p<0.05$) (FIG. 20).

Figure 14A:
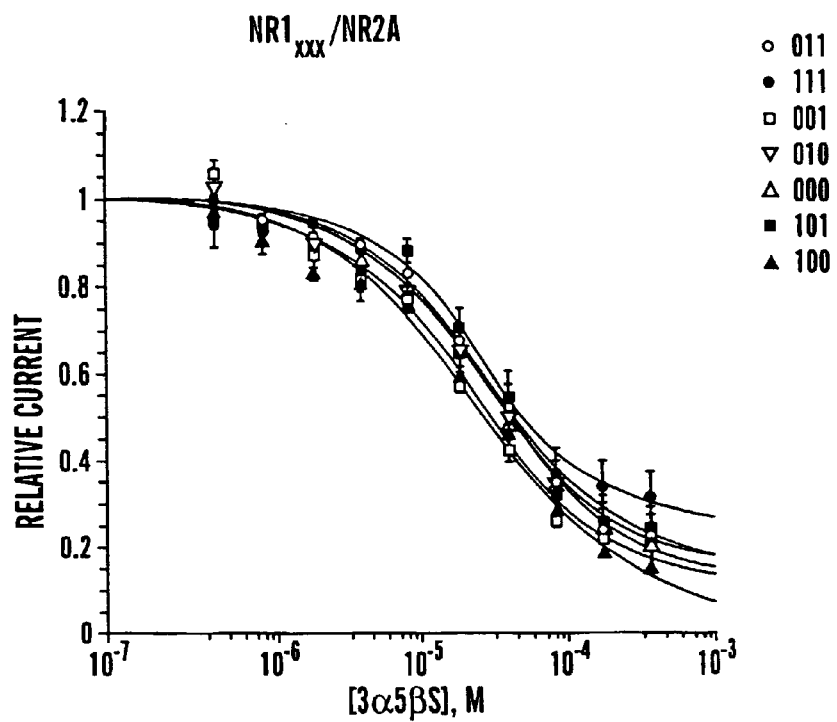
FIG. 14 contains graphical representations of data which compares 3α5βS and PS dose-responses for NR1/NR2A receptors. Presented are normalized current responses obtained from *oocytes* injected with NR1$_{XXX}$/NR2A mRNAs. The current was induced by coapplication of 10 μM glycine and 50 μM NMDA (for N-terminal insert containingt NR1 isoforms, closed symbols) and different concentrations of 3α5βS (A) or PS (B). Error bars are S.E.M. Solid lines are drawn using equation 1+E$_{max}$/(1+(EC$_{50}$/c)$^n$ with parameters from Table 3 and 4.
Figure 14B:
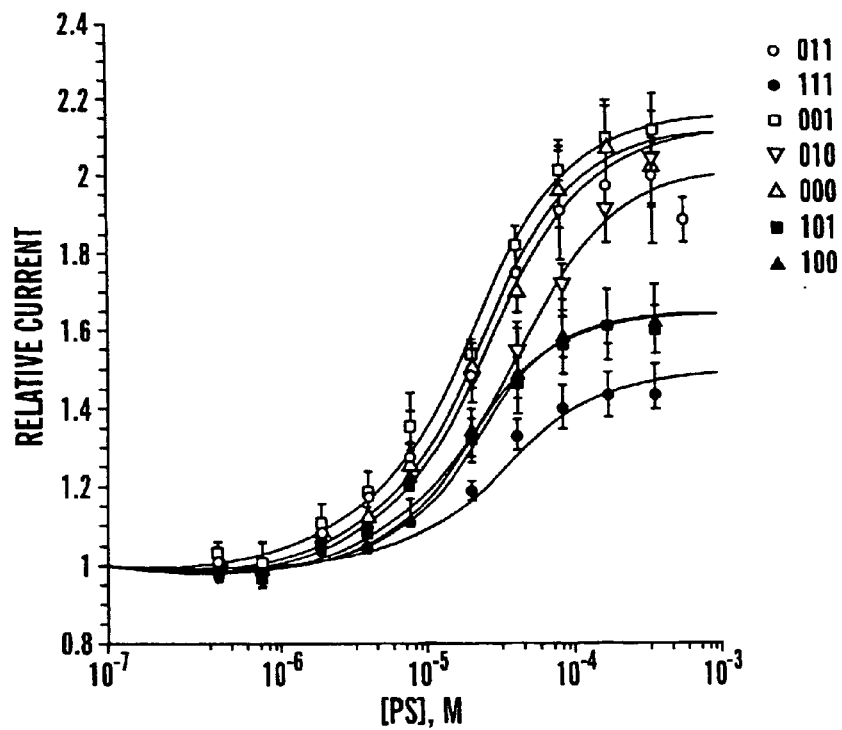
Figure 21:
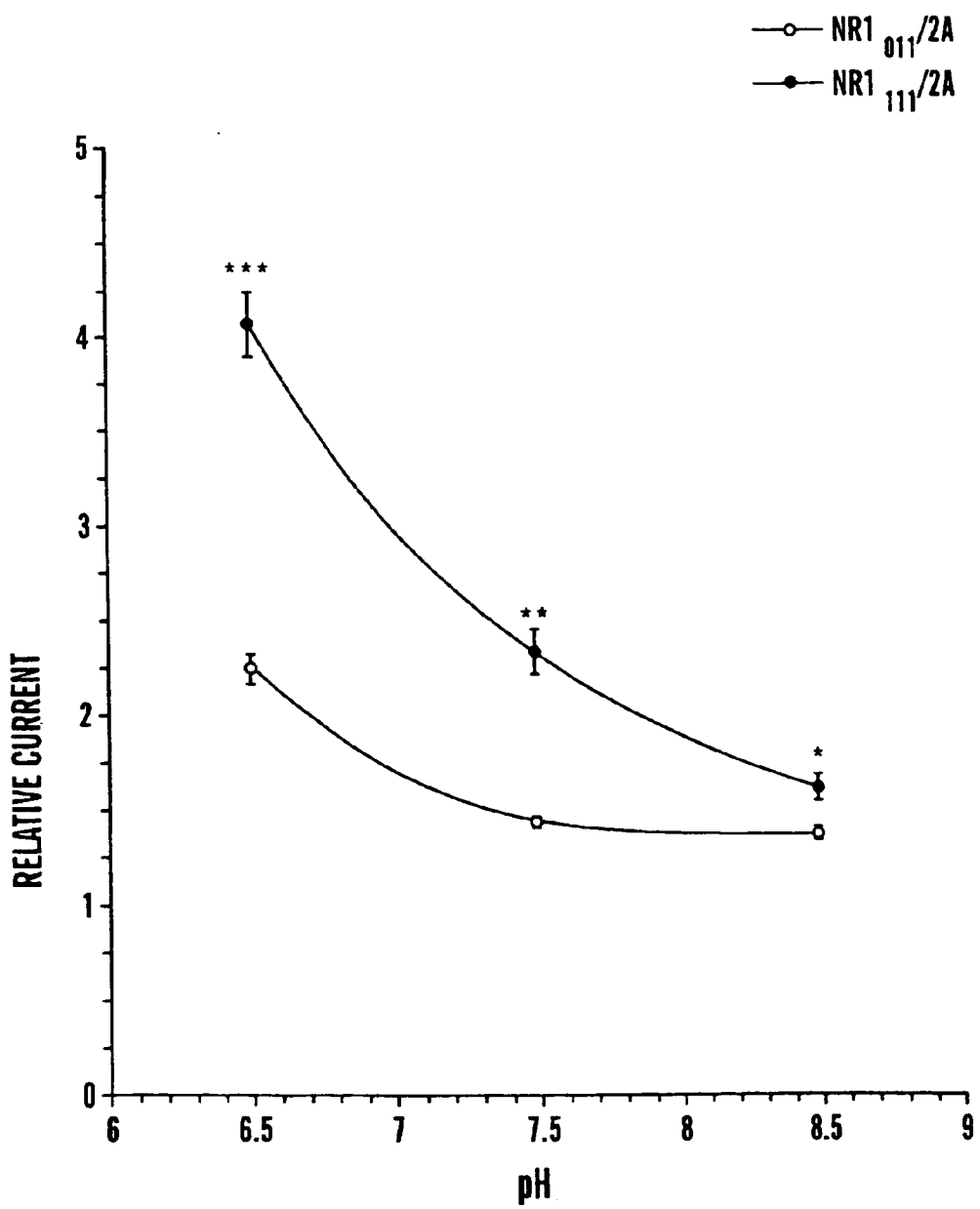
FIG. 21 is a graphical representation of data indicating effect of pH on PS induced modulation of $NR1_{011}/2A$ and $NR1_{111}/2A$ splice variants. A summary graph is shown which illustrates the 100 μM PS induced increase in the response to 200 μM NMDA+10 μM glycine for *oocytes* expressing $NR1_{011}/2A$ or $NR1_{111}/2A$ receptors. The data were normalized relative to the current response induced by co-application of 200 μM NMDA+10 μM glycine to the same *oocyte*. Error bars represent S.E.M of the number of *oocytes* indicated in parantheses. (Significant difference between $NR1_{011}/2A$ and $NR1_{111}/2A$ is indicated by * : p<0.05,  p<5×10$^{-6}$, * : p<5×10$^{-7}$).
Figure 22A:
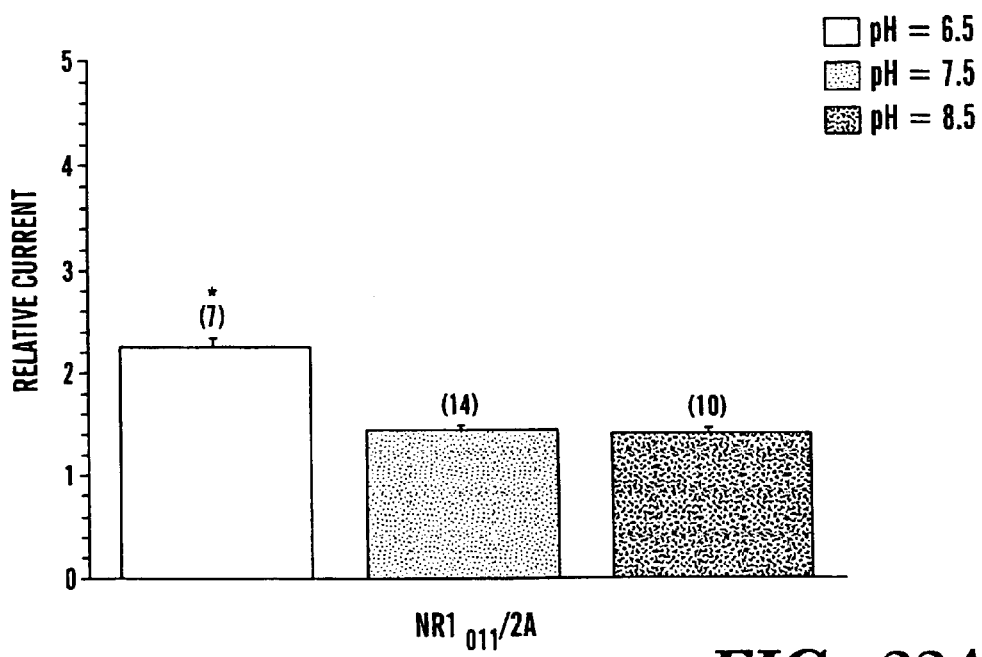
FIG. 22 contains bar graphs of data indicating PS induced modulation on NR1 subunits is pH dependent. Bars indicate the 100 μM PS induced increase in the response to 200 μM NMDA+10 82 M glycine at different pHs, on *oocytes* expressing (A.) $NR1_{011}/2A$ receptors (at pH=6.5 MRC=2.24, at pH=7.5 MRC=1.41 and at pH=8.5 MRC=1.35), and (B.) $NR1_{111}/2A$ receptors (at pH=6.5 MRC=4.06, at pH=7.5 MRC=2.28 and at pH=8.5 MRC=1.58). The data were normalized relative to the current response induced by co-application of 200 82 M NMDA+10 μM glycine to the same *oocyte*. Error bars represent S.E.M of the number of *oocytes* indicated in parantheses. (Significance is indicated for $NR1_{011}/2A$ by *: p<5×10$^{-5}$ and for $NR1_{011}/2A$ by *: p<5×10$^{-6}$ and **: p<5×10$^{-7}$)
Figure 22B:
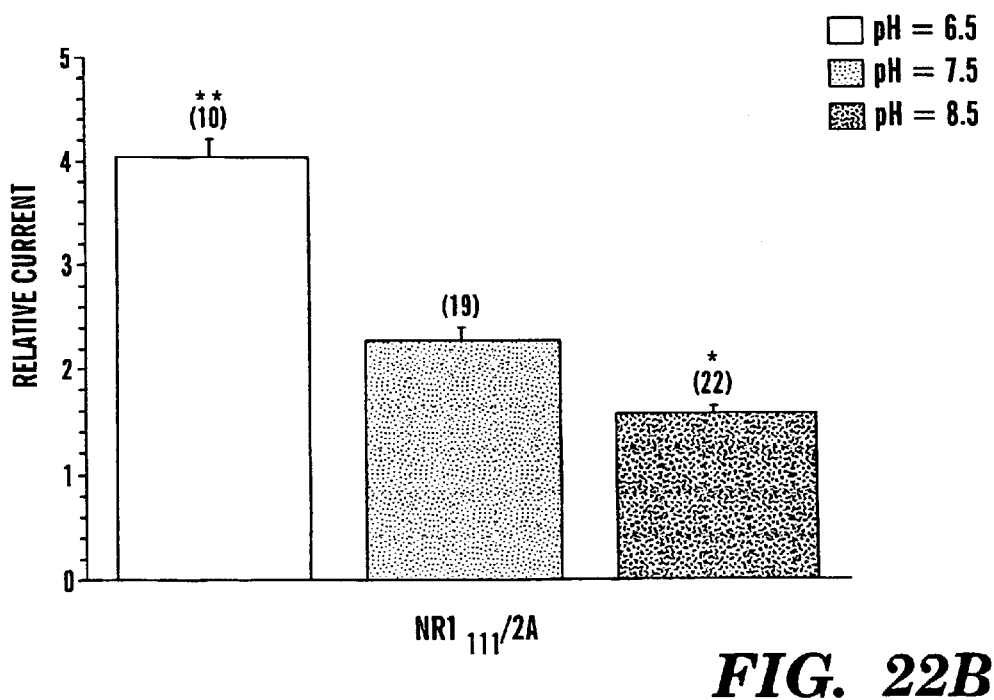

To further investigate the effect of hydrogen ions and thus the involvement of the proton sensor on PS potentiation, the max relative currents (mrc) after co-application of 200 µM NMDA+10 µM glycine±100 µM PS on $NR1_{011}$/NR2A were compared to that of $NR1_{111}$/NR2A, at pH=6.5, 7.5, 8.5, (FIG. 21). These data indicate a 1.8-fold difference between NR1 $_{011}$/NR2A (mrc=2.24) and $NR1_{111}$/NR2A (mrc=4.06) at pH=6.5 (*$p<0.0000005$), a 1.6-fold difference between $NR1_{011}$/NR2A (mrc=1.41) and $NR1_{111}$/NR2A (mrc=2.28), ($p<0.0000005$) and a 1.2-fold difference between $NR1_{011}$/NR2A (mrc=1.35) and $NR1_{111}$/NR2A (mrc=1.59) at pH=6.5 (*$p<0.05$). Moreover, the max relative current data for $NR1_{011}$/NR2A (FIG. 22, panel A) show a 1.7-fold difference between pH=6.5 and pH=7.5 (*$p<0.00005$), and significantly no difference between pH=7.5 and pH=8.5 (*$p<0.00005$). The difference for $NR1_{111}$/NR2A (FIG. 14, panel B) between pH=6.5 and pH=7.5 was 1.8 fold (*$p<0.0000005$) while between pH=7.5 and pH=8.5 was 1.4-fold (*$p<0.000005$). These results indicate that protons participate in PS differential modulation of $NR1_{xxx}$/NR2A splice variants.

Methods of the Invention

Materials

South African clawed frogs, Xenopus laevis, were purchased from either Xenopus One (Ann Arbor, Mich.) or Nasco (Fort Atkinson, Wis.). Frog brittle is also purchased from the same vendors.

Plasmids containing the $NR1_{100}$, $NR1_{000}$, $NR1_{111}$, $NR1_{011}$, $NR1_{101}$, $NR1_{001}$ inserts (encoding different NMDA receptor splice variants) and NR2A (encoding NMDA receptor subunit) were kindly provided by Dr. Shigetada Nakanishi of Kyoto University Faculty of Medicine, Kyoto, Japan.

Competent DH5α cells (used for transformation) were purchased from Gibco (Gaithersburg, Md.). Maxiprep columns were purchased from Qiagen (Chatsworth, Calif.). Restriction enzymes were purchased from New England Biolabs (Beverly, Mass.) and Pharmacia (Piscataway, N.J.). mMessage mMachine in vitro transcription kit (T7 RNA polymerase) was purchased from Ambion (Austin, Tex.).

NMDA and glycine were purchased from Sigma Chemical Co. (St. Louis, Mo.). Chemicals used for the preparation of ND96 and Ringer solutions were purchased from Sigma and Gibco. PS and 3α5βS were purchased commercially from Steraloids (Wilton, N.H.) and Sigma.

Data acquisition and instrument control hardware was purchased from GW Instruments (Somerville, Mass.). SuperScope II v1.43 software was also purchased from GW instruments. Miniature teflon-coated valves were purchased from LeeValves (Essx, Conn). Apple Macintosh IIic was purchased from Apple Computer Inc. (Cupertino, Calif.).

A microprocessor-controlled fixed or variable volume microinjector was purchased from Drummond Inc. (Broomall, Pa.). Micromanipulators (no. M3301) were purchased from World Precision Instruments (Sarasota, Fla.), translation stages (single axis, no. 423), 50 mm open loop motorized DC actuators (no. 860-A), hand-held single axis controller (no. 861), low profile magnetic base (no. 150), 45° angle bracket (no. 360-45) from Newport Inc. (Irwine, Calif.) and the headstages for the electrodes from Drummond Inc. The OC-725 *Oocyte* Clamp amplifier was purchased from Warner Instrument Corp. (Hamden, Conn.) and the Axoclamp-2A amplifier from Axon Instruments Inc., Foster City, Calif.). A programmable horizontal Flaming-Brown micropipette puller was purchased from Sutter Instruments Co., Calif. Perfusion manifolds (no. ML-6) and polyethylene (PE) tubing (no. PE-50 and PE-160) were purchased from Warner Instrument Corp. Glass pipettes for RNA microinjection (RNase-free 3.5-in. glass capillaries no. 3-000-203-Cdx) were purchased from Drummond. Glass electrodes (borosilicate glass 100 µl disposable micropipettes, no. TWI50F-4) were purchased from World Precision Instruments.

Preparation of mRNA

For the microinjection into *Xenopus oocytes*, mRNA was prepared from lyophilized plasmid pellets containing cDNA insets encoding the specific NMDA receptor splice variant. Transformation of competent DH5a (sub-cloning quality) cells resulted in bacterial cultures expressing the desired plasmids. Overnight cultures (500 ml) of transformed bacterial cells were prepared in order to grow sufficient quantities for maxiprep isolation of the plasmid CDNA. Maxipreps were done using a Sorvall RC-5B ultracentrifuge, Qiagen columns and cDNA was quantitated with spectrophotometry ($OD_{260}$ and $OD_{260}/OD_{280}$ ratio). The resulting plasmid cDNA was linearized by digestion with an appropriate restriction enzyme that cleaves distal to the cDNA insert (XhoI for NR2A or NotI for $NR1_{100}$, $NR1_{000}$, $NR1_{111}$, $NR1_{011}$, $NR1_{101}$, $NR1_{001}$). Following digestion, plasmid cDNA was treated with proteinase K (degradation of RNAse) and extracted with a combination of phenol/chloroform/isoamyl alcohol, after which ethanol precipitation was used to pellet DNA prior to the start of the transcription reaction. cDNA quality was assessed by agarose-gel electrophoresis (1.5% agarose gel). The samples were stored at −20° C. until use.

In vitro transcription was performed using the Ambion mMessage mMachine kit with T7 ($NR1_{100}$, $NR1_{000}$, $NR1_{111}$, $NR1_{011}$, $NR1_{101}$, $NR1_{001}$) RNA polymerase. The reaction was assembled on ice and allowed to incubate at 37° C. for 1–2 hr. The resulting mRNA was precipitated (reaction termination) using lithium chloride/5 mM EDTA solution and dissolved in RNase-free $H_2O$. The concentration ($OD_{260}$) and $OD_{260}/OD_{280}$ ratio (should be more than 1.5) was determined by spectrophotometer. The yield of mRNA was generally 15–30 µg. mRNA was stored at −80° C. until use.

Electrophysiological recordings of ion currents from *oocytes* expressing the desired NMDA receptor subtypes ($NR1_{100}$, $NR1_{000}$, $NR1_{111}$, $NR1_{011}$, $NR1_{101}$, $NR1_{001}$/NR2A) were carried out using either the OC-725 *Oocyte* Clamp amplifier from Warner Instruments or the Axoclamp-2A amplifier from Axon Instruments Inc. in a two-electrode voltage clamp mode. Intracellular recording microelectrodes were fabricated from 100 µl borosilicate glass disposable micropipettes using a 2-step protocol on a standard horizontal Flaming-Brown micropipette puller.

Perfusion control and data acquisition were carried out using an automated *oocyte* electrophysiology workstation and custom-written software implemented in the SuperScope II environment, which was developed for the rapid collection of concentration-response data and real time waveform analysis (Yaghoubi et al., Evaluation on neurosteroid modulation of kainate receptors using an automated system for *oocyte* electrophysiology. In Society for Neuroscience, pp. 1109 (1995)). All experiments were performed at room temperature (22–24° C).

EXAMPLE 5

Sulfated steroids can act as positive or negative modulators of NMDA receptor function. For instance, pregnenolone sulfate (PS), an abundant neurosteroid, potentiates NMDA-induced currents, whereas 3α5β-pregnanolone sulfate (3α5βS) inhibits NMDA-induced currents. Moreover, PS does not competitively inhibit the binding of 3α5βS to the NMDA receptor, indicating the presence of independent binding sites or pathways for negative and positive modulation.

The following experiments have identified amino acids on subunit 1 of the NMDA receptor (NR1) that control PS potentiation of NMDA-induced currents in recombinant NR1a/NR2A receptors, where NR1a corresponds to $NR1_{011}$. These amino acids were identified using multiple sequence alignments and then tested for functional activity in xenopus *oocytes* using mutated NR1a expression constructs. In the first case, the sequence of the NR1a subunit was aligned with that corresponding to the ligand binding domain of five nuclear receptors: human retinoid X receptor α (RXR), the human retinoic acid receptor γ (RAR), the human progesterone receptor (PR), the human glucocorticoid receptor (GCR) and the estrogen receptor (ER). A region was defined in the NR1a subunit, residue I163 to residue N273, which shares 44% sequence similarity to the aforementioned nuclear receptors, spanning helix 3 to helix 6 (FIG. 23).

Figure 24:
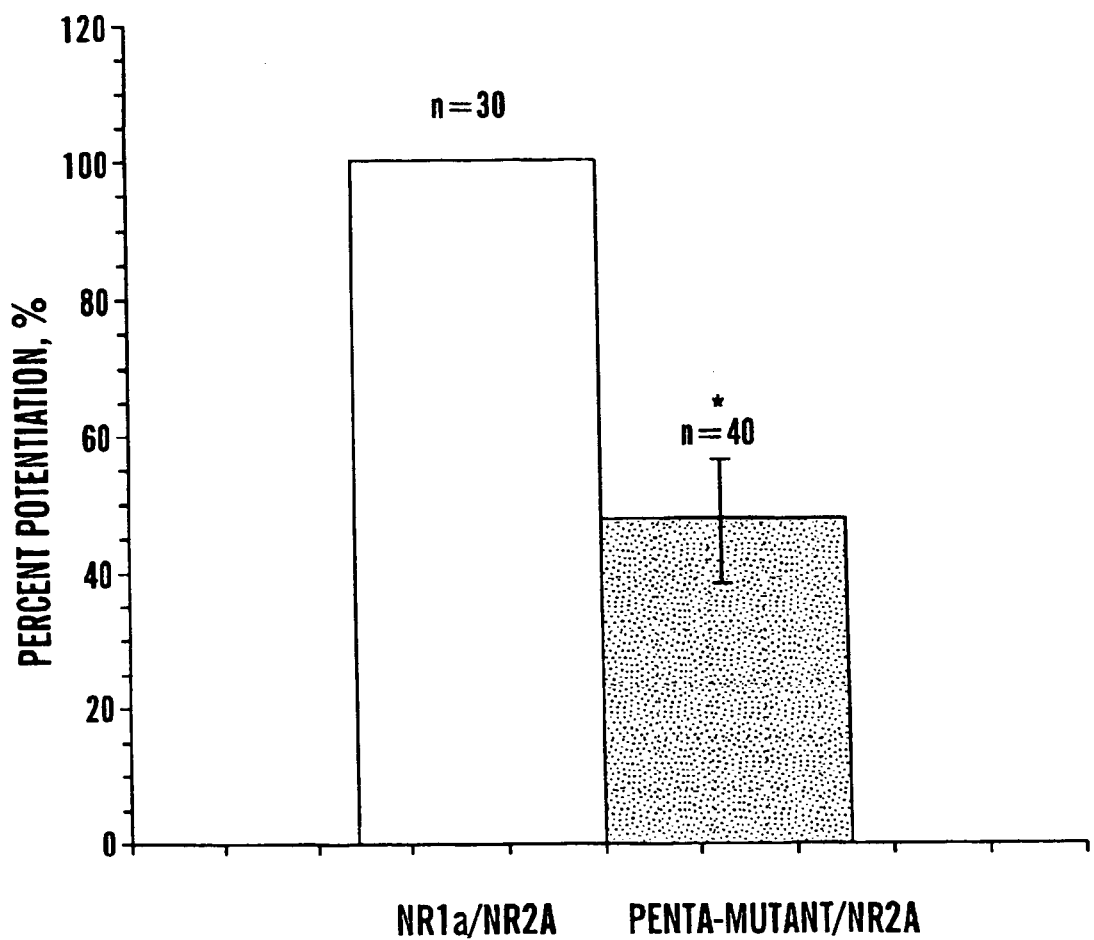
FIG. 24 is a bar graph of data indicating effect of NR1 penta-mutant on NMDA receptor function. Mutation of 5 residues in the NR1 subunit (indicated in FIG. 23) results in a 47.5±8.80% (mean±SEM) reduction in pregnenolone sulfate (PS) potentiation of the NMDA response. The bars represent percent increase in maximum inward currents elicited by 300 uM NMDA and 50 uM Glycine in the presence of 100 uM PS. Data is displayed as means plus/minus the standard error fo the mean with the number of individual *oocytes* used in the experiments indicated as N. Currents were recorded at −70 mV, in Ba$^{2+}$ Ringer's solution (in mM); 96 NaCl, 2 KCl, 1.8 BaCl$_2$, 5 HEPES, pH=7.5.
Figure 25:
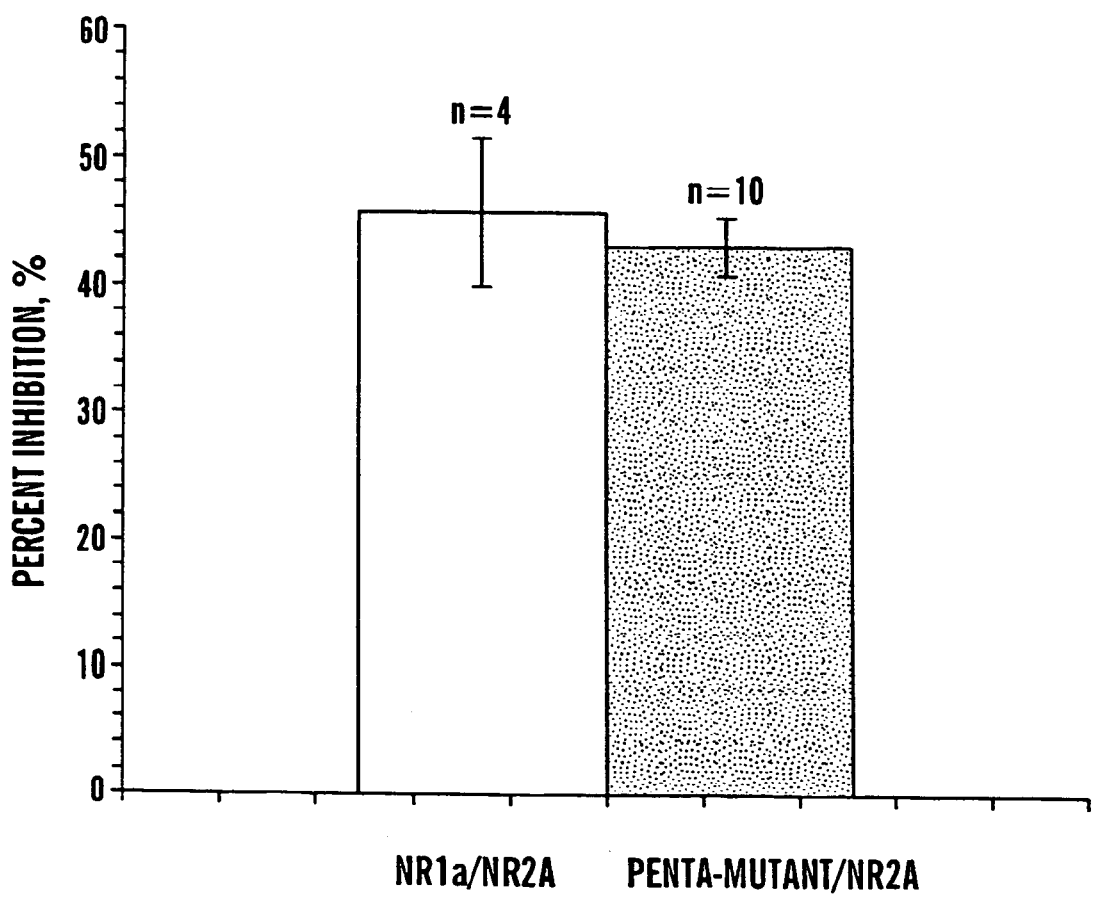
FIG. 25 is a bar graph of data indicating 3α5β-Pregnanolone Sulfate has similar effect on NMDA receptors consisting of wild-type NR1a/NR2A and Penta-Mutant/NR2A subunits. The bars represent percent decrease in maximum inward currents elicited by 300 uM NMDA and 50 um Glycine in the presence of 100 uM 3α5β-Pregnanolone Sulfate. 3α5β-Pregnanolone Sulfate inhibits wild-type NR1a/NR2A responses by 45.49±5.76% (mean±SEM) and Penta-Mutant/NR2A by 42.79±2.29%. Data is displayed as mean±the standard error of the mean with the number of individual *oocytes* used in the experiment indicated as N. The currents were recorded at −70 mV, in Ba$^{2+}$-Ringer's solution (in mM): 96 NaCl, 2 KCl, 1.8 BaCl$_2$, 5 HEPES, pH=7.5.

Using the information from the sequence alignment, the mutant Penta-mutant (PM) was constructed by replacing five positively charged residues (R187, K193, K202, R233, and R252) with alanines (FIG. 23). PM was co-expressed with NR2A in the xenopus *oocyte* expression system. The receptors containing PM were functional with an EC50 of 55.0±3.4 uM for the NMDA response, similar to the wild-type receptor. However, the PM containing receptors showed a 40% reduction in sensitivity to PS in the presence of 100 uM PS, 300 uM NMDA and 50 uM Glycine (FIG. 24). In contrast, PM did not effect the response of the NMDA receptor to the negative modulator 3α5βS (FIG. 25). These results demonstrate for the first time that there is a distinct molecular component for pregnenolone sulfate modulation of NMDA receptor function and are consistent with the hypothesis that PS and 3α5↑S modulate NMDA-induced currents through distinct sites.

Methods of the Invention

Mutagenesis

Site directed mutagenesis was generated by a method involving PCR. In brief, oligonucleotides were synthesized containing the mutation, and these oligonucleotides were used in combination with other oligonucleotides in PCR amplifications of fragments of the cDNA. The product of the PCR reactions were cut with two different restriction enzymes to generate a cassette containing the mutation. This cassette was then ligated into the cDNA that was cut with the same two restriction enzymes. For all of the mutations, single isolates were selected, and the entire region of the amplified cassette was sequenced to check for the mutation and to insure against second-site mutations.

Preparation of RNA

Plasmids containing the $NR1_{011}$ and NR2A cDNA inserts were kindly provided by Dr. Nakanishi (Kyoto University Faculty of Medicine, Kyoto, Japan), while plasmids containing the NR2B, NR2C and NR2D cDNA inserts were kindly provided by Dr. Seeburg (Heidelberg University, Heidelberg, Germany). Plasmids were linearized with appropriate restriction enzyme prior to in vitro transcription using the Message Machine kit (Ambion, Inc., Austin, Tex.).

Expression in *Xenopus* oocytes

Female, *oocyte* positive *Xenopus laevis* frogs were purchased from Xenopus I (Dexter, Mich). Following 45 min of 0.15% Tricaine anesthesia, ovarian sections containing the follicular *oocytes* were removed from the frog through a lateral abdominal incision and were immediately placed in a calcium-free solution (NaCl 96 mM, $MgCl_2$ 1 mM, KCl 2 mM, Hepes 50 mM, pyruvate 2.5 mM, 0.1 mg/ml gentamicin, pH 7.4). Following.1.5–2 hours incubation in 0.2% collagenase (type II, Sigma Chemical Co., St. Louis, Mo.) at room temperature, individual defolliculated Dumont stage V and VI *oocytes* were transferred to an incubator and maintained overnight in Barth's solution (NaCl 84 mM, $NaHCO_3$ 2.4 mM, $MgSO_4$ 0.82 mM, KCl 1 mM, $Ca(NO_3)_2$ 0.33 mM, CaCl 0.41 mM, Tris/HCl 7.5 mM, pyruvate 2.5 mM, 0.1 mg/ml gentamicin, pH 7.4) at 18–20° C. Oocytes were injected with 50 nL of RNA solutions using an electronic microinjector (Drummond Inc., Broomall, Pa.). The transcripts were injected at a ratio of 0.125/1.25 ng mRNA per *oocyte* for NR1a/NR2A or penta-mutant/NR2A receptors and 0.5/5 ng mRNA per *oocyte* for NR1a/NR2B, NR1a/NR2C, and NR1a/NR2D receptors. The injected *oocytes* were used for experiments following 1–5 days of incubation in Barth's solution at 18–20° C.

Electrophysiology

Measurements of ion currents from *oocytes* expressing NMDA receptors were performed using an Axoclamp-2A voltage clamp amplifier (Axon Instruments, Inc., Foster City, Calif.) in two-electrode voltage clamp mode. The microelectrodes were fabricated with a programmed puller (Sutter Instrument Co., Calif.) from borosilicate glass capillaries and were filled with 3 M KCl solution. The resistance of filled microelectrodes was in the range of 1–3 MΩ. The *oocyte* recording chamber was continuously perfused with $Mg^{2+}$-free Ba-Ringer solution (NaCl 96 mM, KCl 2 mM, $BaCl_2$ 1.8 mM, Hepes 5 mM). In order to minimize activation of $Ca^{2+}$-dependent $Cl^-$ conductance the perfusion solutions used did not contain $Ca^{2+}$ ions. If not mentioned otherwise, during data acquisition *oocytes* were clamped at a holding potential of −70 mV. The membrane current was filtered at 500 Hz and sampled at 100 Hz. Drugs were applied using a gravity driven external perfusion system. The working ,volume of the recording chamber was 30 μl and the rate of the perfusion was 50 μl/sec. The drug application lasted 10 sec and was followed by a 60 sec wash. The data acquisition and external perfusion control were done using the SuperScopeII software package (GW Instruments, Mass.). All experiments were performed at room temperature (22–24° C.). Peak or steady-state current measurements were normalized and expressed as a fraction of the peak or steady-state control current measurements, which were performed before and after application of every single consentration of agonist or steroid. In order to derive the values of NMDA receptor agonists and PS $EC_{50}$s, experimental dose-response data were fit using equations $E_{max}/(1+(EC_{50}/c)^n)$ or $1+E\max/(1+(EC50/c)^n)$ respectively, where $E_{max}$ is a maximum response, n-Hill coefficient, c-concentration of an agonist. The data are presented as mean±S.E.M. with number of experiments in parentheses.

Chemicals p Steroids were obtained from Steraloids, Inc. (Wilton, N.H.) and were dissolved in DMSO prior to use. Other compounds were obtained from Sigma (St. Louis, Mo.).

EXAMPLE 6
NMDA Receptor Expression in *Xenopus oocytes*

To investigate the influence of NMDA receptor subunit composition on the modulatory effects of neuroactive steroids, mRNA coding for the $NR1_{100}$ subunit was coinjected into *Xenopus laevis oocytes* along with mRNA coding for either the NR2A, NR2B, NR2C, or NR2D subunit. All 4 subunit combinations resulted in expression of functional NMDA receptors 1–5 days after injection, as indicated by an inward current in response to application of 80 μM NMDA plus 10 μM glycine. Concentration-response studies showed that the NMDA $EC_{50}$ differed substantially across the different subunit combinations. Therefore, to compare modulatory effects of steroids, a concentration of NMDA close to its $EC_{50}$ for each subunit combination was used (80 μM for NR1/NR2A, 25 μM for NR1/NR2A and NR1/NR2B, and 10 μM for NR1/NR2D).

Subunit-selective Modulation by PS

As shown in FIG. 26, the choice of NR2 subunit dictated the direction of modulation by PS. Co-application of 100 μM PS with NMDA plus glycine to *oocytes* expressing NR1/NR2A receptors resulted in an enhancement of 62±8% (n=8) over the current induced by NMDA plus glycine alone. Similarly, with *oocytes* expressing NR1/NR2B receptors, the NMDA-induced current was enhanced 78±9% (n=4) in the presence of 100 μM PS. In contrast, *oocytes* expressing NR1/NR2C receptors exhibited 35±3% (n=4) inhibition of the NMDA-induced current, and *oocytes* expressing NR1/NR2D receptors exhibited 26±1% (n=9) inhibition of the NMDA response.

Figure 26A:
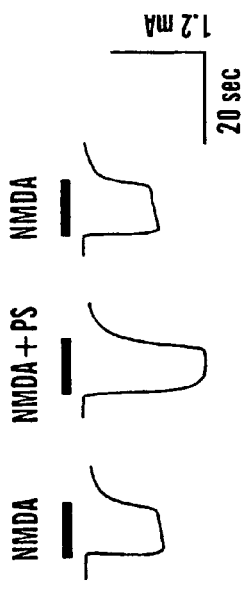
FIG. 26 contains graphical representations of data indicating inverse modulation of NMDA receptor subtypes by PS. A–D are examples of traces obtained from *oocytes* previously injected with NR1/NR2A, NR1/NR2B, NR1/NR2C, or NR1/NR2D mRNAs. The bar indicates the period of drug application. Interval between consecutive current traces was 45 s. The receptors were activated by co-application of 10 μM glycine plus 80 μM NMDA (NR1/NR2A, A), 25 μM NMDA (NR1/NR2B, B and NR1/NR2C, C), or 10 μM NMDA (NR1/NR2D, D). Co-application of 100 μM PS to NR1/NR2A or NR1/NR2B receptors resulted in an increase in the agonist response, whereas co-application of 100 μM PS to NR1/NR2C or. NR1/NR2D resulted in a decrease in the agonist response. E is dose-response curves for PS effect on NR1/NR2 receptors. Data points are averaged values of normalized peak current responses from *oocytes* injected with NR1/NR2A (n=8), NR1/NR2B (n=8), NR1/NR2C (n=4) or NR1/NR2D (n=4) RNAs. Responses were normalized to the control response obtained by application of 10 μM glycine plus 80 μM NMDA (NR2A), 25 μM NMDA (NR2B, NR2C) or 10 μM NMDA (NR2D). Error bars indicate SEM. F indicates the effect of holding potential on modulation of the NMDA/glycine response by PS. Points are averaged relative currents obtained in the presence of 100 μM PS, standardized relative to the response induced from the same *oocyte* by 10 μM glycine plus 80 μM (NR1/NR2A, n=4), 25 μM (NR1/NR2B, n=7; NR1/NR2C, n=3), or 10 μM NMDA (NR1/NR2D, n=3). Error bars indicate SEM.
Figure 26B:
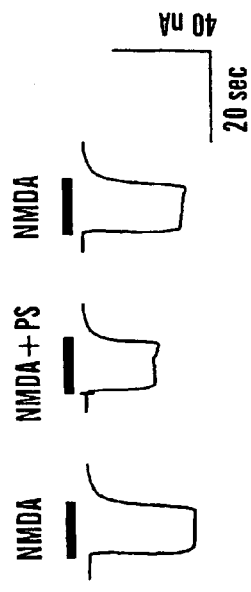
Figure 26C:
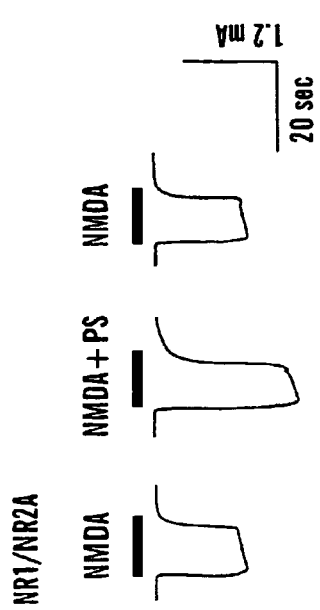
Figure 26D:
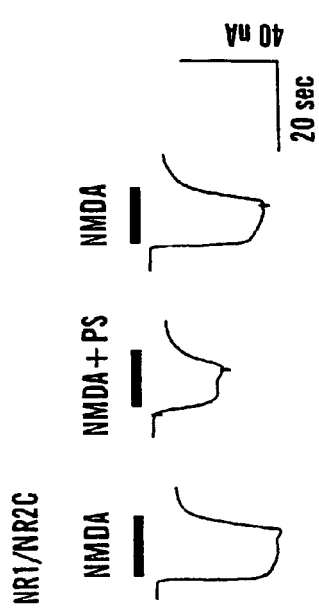
Figure 26F:
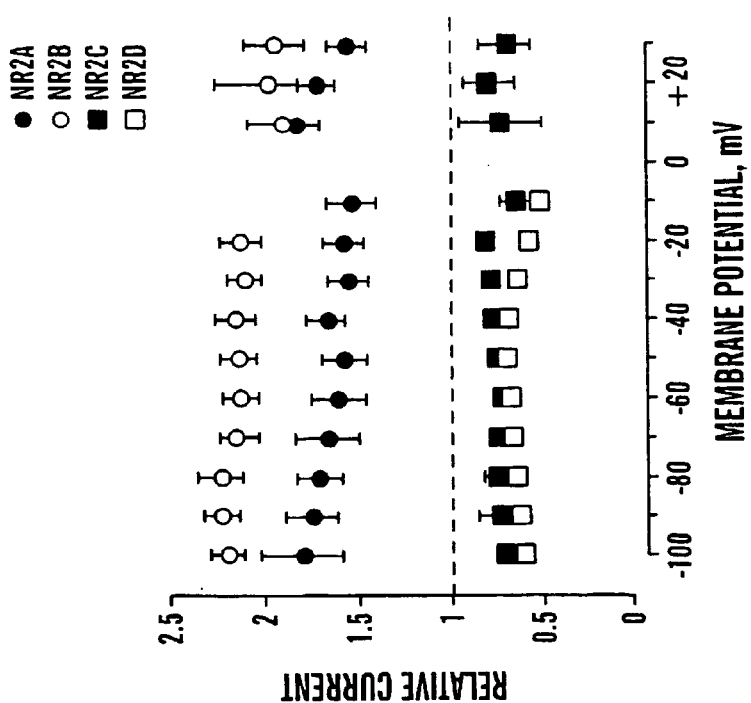
Figure 26E:
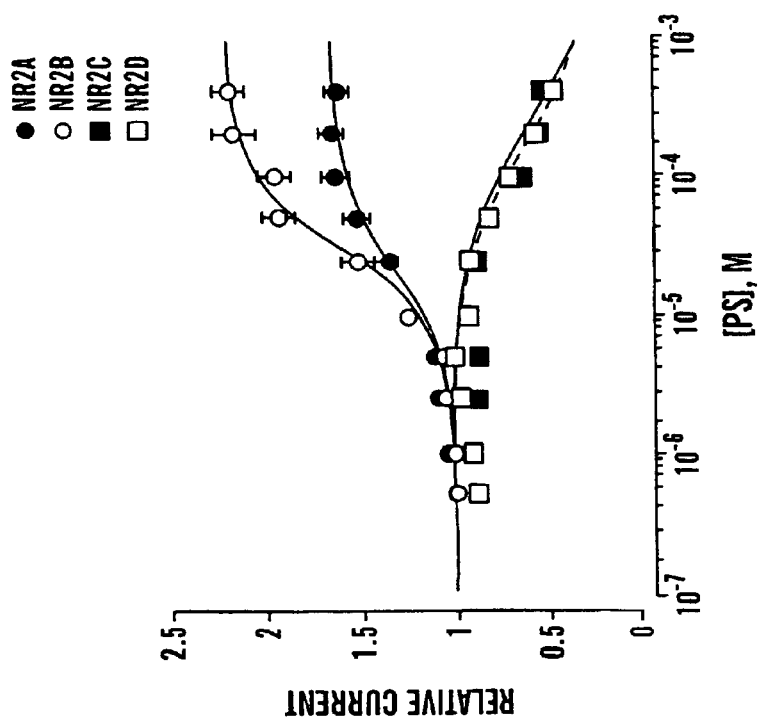

To examine the influence of subunit composition on the concentration dependence of PS action, PS was applied to *oocytes* expressing NR1/NR2A, NR1/NR2B, NR1/NR2C, or NR1/NR2D, together with 10 μM glycine and a concentration of NMDA approximately equivalent to its $EC_{50}$ for that subunit combination. As shown in FIG. 26E and Table 3, PS was about equally potent in potentiating NR1/NR2A ($EC_{50}$=21 μM) and NR1/NR2B receptors ($EC_{50}$ 33 μM), and 3.4- to 5.6-fold less potent as an inhibitor of NR1/NR2C ($EC_{50}$ 112 μM) and NR1/NR2D receptors ($EC_{50}$ 118 μM). Enhancement of NR1/NR2A and NR1/NR2B receptors and inhibition of NR1/NR2C and NR1/NR2D receptors exhibited little if any voltage dependence. (FIG. 26F).

TABLE 3

Concentration dependence of PS modulation of the NMDA response. Results from each oocyte (number given in far right column) were independently fitted to the logistic equation. $E_{max}$ is expressed as percentage change (+ for potentiation, − for inhibition) in the presence of PS, relative to the response induced in the same oocyte by an approximate $EC_{50}$ concentration of NMDA in the presence of 10 μM glycine. $EC_{50}$ values are averaged as logarithms (De Lean, et al., 1978) ± the SEM of the log $EC_{50}$. Concentration of NMDA was 80, 25, 25, and 10 μM for NR1/NR2A, NR1/NR2B, NR1/NR2C, and NR1/NR2D, respectively (see Methods).

| Subunits | PS $E_{max}$ (% Change) | PS $EC_{50}$ | log PS $EC_{50}$ | $n_H$ | (#) |
|---|---|---|---|---|---|
| NR1/NR2A | +167 ± 7% | 21 μM | −4.68 ± 0.09 | 1.33 ± 0.08 | (8) |
| NR1/NR2B | +202 ± 10% | 33 μM | −4.49 ± 0.05 | 1.42 ± 0.11 | (4) |
| NR1/NR2C | −63 ± 9% | 112 μM | −3.95 ± 0.29 | 1.32 ± 0.29 | (4) |
| NR1/NR2D | −70 ± 6% | 118 μM | −3.92 ± 0.11 | 1.16 ± 0.08 | (4) |

Figure 27D:
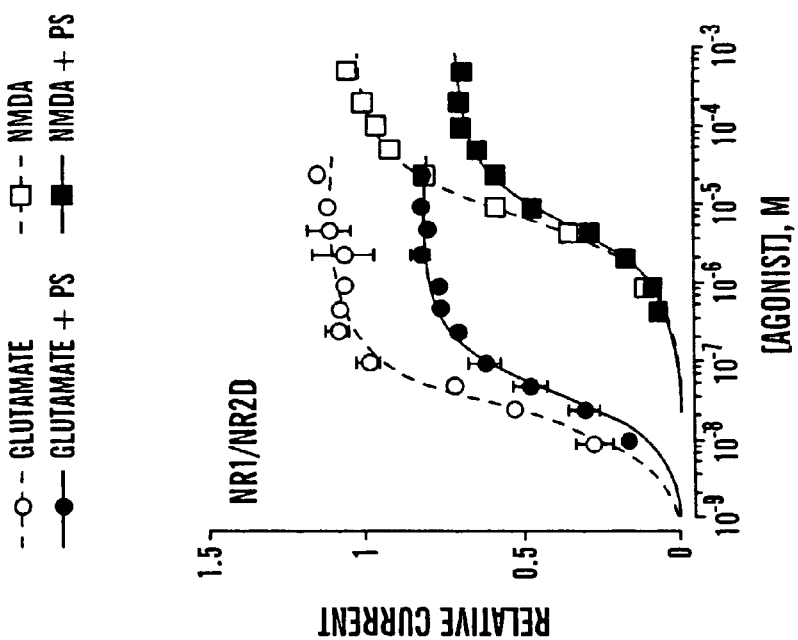
FIG. 27 contains four dose response curve graphs. The choice of NR2 subunit determines the direction of PS modulation of the glutamate and NMDA concentration-response curves. Data points are averaged normalized peak NMDA-induced current responses obtained from *oocytes* injected with (A) NR1/NR2A, (B) NR1/NR2B, (C) NR1/NR2C, or (D) NR1/NR2D mRNAs. Concentration-response data for NMDA (squares) and for L-glutamate (circles) were obtained in the presence of 10 μM glycine. The data were normalized relative to the current response from the same *oocyte* induced by co-application of 200 μM NMDA and 10 μM glycine. Open symbols and dashed lines correspond to data obtained in the absence of PS, whereas filled symbols and solid lines correspond to data obtained in the presence of 100 μM PS. Error bars represent SEM.
Figure 27C:
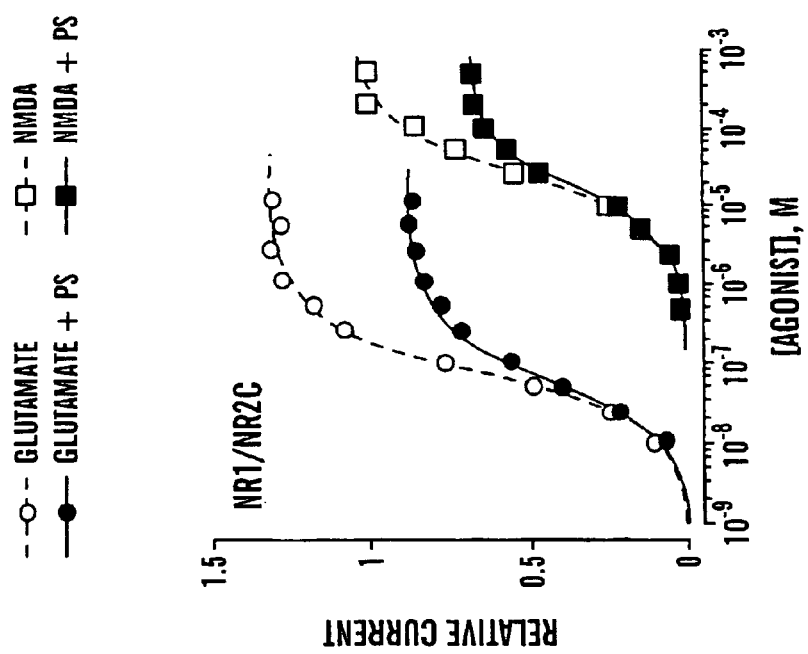
Figure 28B:
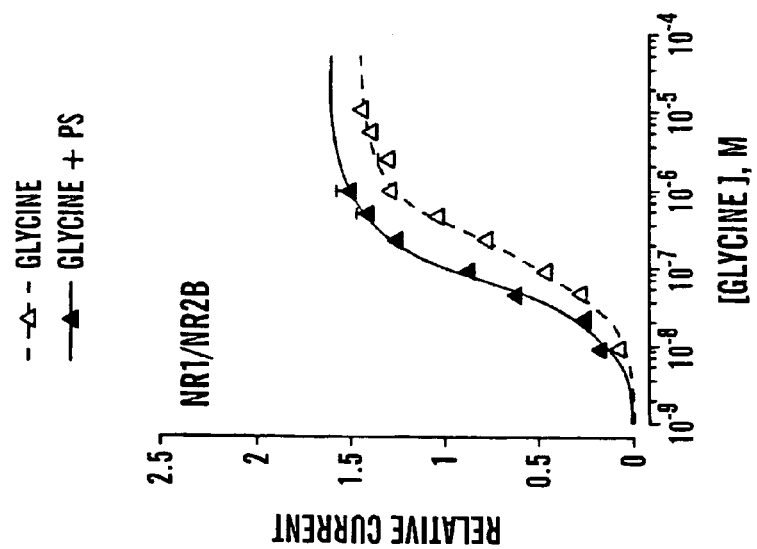
FIG. 28 contains graphical representations of data indicating that the choice of NR2 subunit determines the direction of PS modulation of the glycine concentration-response curve. Data points are averaged normalized peak current responses obtained from *oocytes* injected with (A) NR1/NR2A, (B) NR1/NR2B, (C) NR1/NR2C, or (D) NR1/NR2D mRNAs. Concentration-response data for glycine were obtained in the presence of 10 μM L-glutamate and in the absence (open triangles) and presence (closed triangles) of 100 μM PS. The data for each *oocyte* were normalized relative to the current response induced by co-application of 200 μM NMDA plus 10 μM glycine. Error bars represent SEM.
Figure 28A:
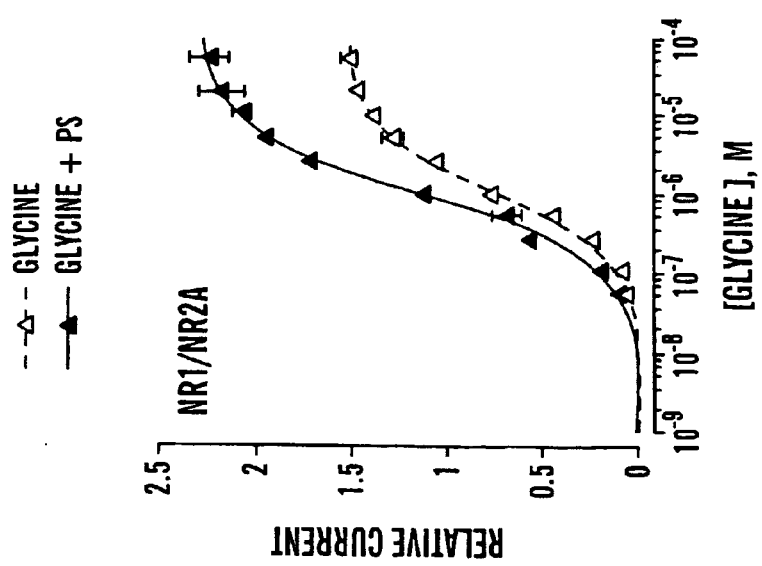

To determine how PS enhances or inhibits the response of the NMDA receptor, the glutamate, NMDA, and glycine concentration-response curves were determined in the presence and absence of PS. As shown in FIGS. 27 and 28, the nature of the modulatory effect of PS depended not only upon subunit combination, but also upon the specific agonist used. With NR1/NR2A receptors, PS enhanced the efficacy of NMDA, glutamate (FIG. 27A) and glycine (FIG. 28A), while decreasing the glutamate and glycine $EC_{50}$s (Table 4A). At NR1/NR2B receptors, however, PS enhanced both potency and efficacy of NMDA, but only enhanced the potency of glutamate (FIG. 27B), while glycine potency was increased with only a slight increase in efficacy (FIG. 28B and Table 4B).

TABLE 4

| Subunits | Agonist | $E_{max}$ | $EC_{50}$ | log $EC_{50}$ | $n_H$ | (#) |
|---|---|---|---|---|---|---|
| A. NR1/NR2A | Glu | 1.50 ± | 450 nM | −6.34 ± | 1.15 ± 0.04 | (4) |
| | Glu (PS) | 2.3 ± 0.2** | 300 nM**| −6.52 ± | 0.98 ± 0.06 | (4) |
| | NMDA | 1.36 ± 0.04 | 73 μM | −4.14 ± 0.04 | 1.13 ± 0.04 | (11) |
| | NMDA (PS) | 1.60 ± | 39 μM**| −4.41 ± | 1.20 ± 0.06 | (6) |
| | Gly | 1.58 ± 0.04 | 1.1 μM | −5.96 ± 0.06 | 1.58 ± 0.04 | (9) |
| | Gly (PS) | 2.34 ± | 960 nM | −6.02 ± 0.03 | 1.03 ± 0.05 | (4) |
| B. NR1/NR2B | Glu | 1.23 ± 0.04 | 250 nM | −6.59 ± 0.05 | 1.14 ± 0.10 | (4) |
| | Glu (PS) | 1.34 ± 0.07 | 84 nM**| −7.08 ± | 1.05 ± 0.02 | (3) |
| | NMDA | 1.00 ± 0.02 | 25 μM | −4.59 ± 0.01 | 1.28 ± 0.08 | (4) |
| | NMDA (PS) | 1.47 ± | 12 μM**| −4.92 ± | 1.32 ± 0.11 | (4) |
| | Gly | 1.49 ± 0.03 | 200 nM | −6.69 ± 0.05 | 1.09 ± 0.04 | (10) |
| | Gly (PS) | 1.63 ± 0.04* | 80 nM | −7.09 ± | 1.15 ± 0.03 | (4) |
| C. NR1/NR2C | Glu | 1.31 ± 0.02 | 75 nM | −7.13 ± 0.03 | 1.27 ± 0.06 | (4) |
| | Glu (PS) | 0.87 ± | 60 nM | −7.23 ± 0.04 | 1.18 ± 0.06 | (6) |
| | NMDA | 1.05 ± 0.01 | 24 μM | −4.62 ± 0.02 | 1.18 ± 0.02 | (4) |
| | NMDA (PS) | 0.69 ± | 15 μM**| −4.81 ± | 1.33 ± 0.03 | (3) |
| | Gly | 1.31 ± 0.01 | 360 nM | −6.45 ± 0.02 | 1.18 ± 0.05 | (4) |
| | Gly (PS) | 0.87 ± | 190 nM**| −6.72 ± | 1.11 ± 0.12 | (5) |

TABLE 4-continued

| Subunits | Agonist | $E_{max}$ | $EC_{50}$ | log $EC_{50}$ | $n_H$ | (#) |
|---|---|---|---|---|---|---|
| D. NR1/NR2D | Glu | 1.10 ± 0.03 | 25 nM | −7.61 ± 0.06 | 1.26 ± 0.12 | (5) |
| | Glu (PS) | 0.80 ± | 37 nM | −7.43 ± 0.11 | 1.35 ± 0.15 | (5) |
| | NMDA | 1.02 ± 0.01 | 8.0 μM | −5.09 ± 0.01 | 1.26 ± 0.09 | (4) |
| | NMDA (PS) | 0.71 ± | 6.2 | −5.21 ± | 1.17 ± 0.01 | (5) |
| | Gly | 1.22 ± 0.05 | 100 nM | −7.00 ± 0.08 | 1.12 ± 0.08 | (5) |
| | Gly (PS) | 0.74 ± | 70 nM | −7.17 ± 0.02 | 0.95 ± 0.01 | (3) |

Effect of PS on agonist concentration-response relationships. Peak agonist-induced currents from each oocyte were separately fitted to the logistic equation to estimate $EC_{50}$, $E_{max}$, $n_H$. Values reported are mean parameter values ± SEM of the number of oocytes given in the far right column. Responses (and therefore $E_{max}$ estimates) are normalized to the magnitude of the peak 200 μM NMDA plus 10 μM glycine-induced current from the same oocyte.
**Indicates a statistically significant (p < 0.05) change compared to the parameter value in the absence of PS.
*Indicates a significant effect of PS on the glycine concentration-response curve but it could not be distinguished whether effect was on $EC_{50}$ or $E_{max}$ (see Methods).

Figures 28C, 28D:
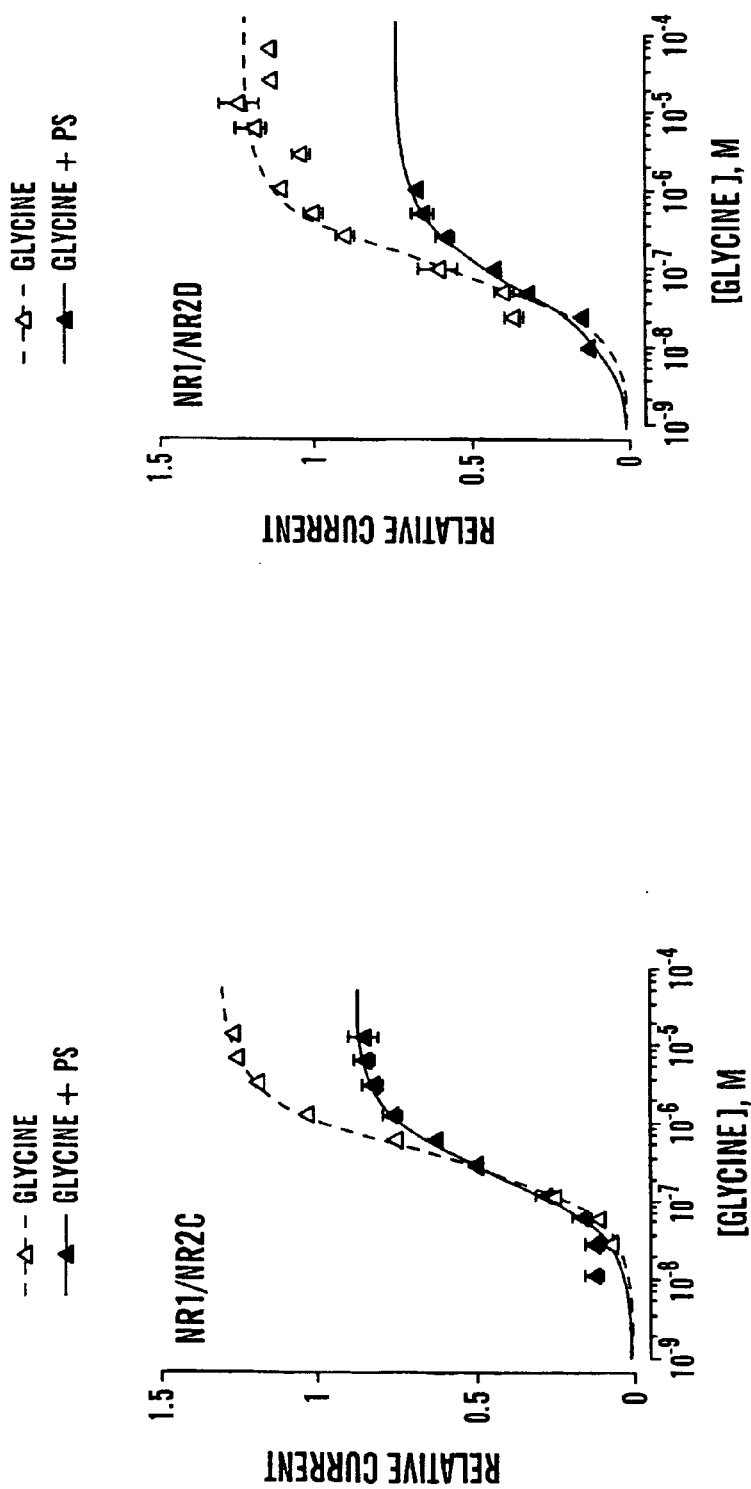
Figure 29B:
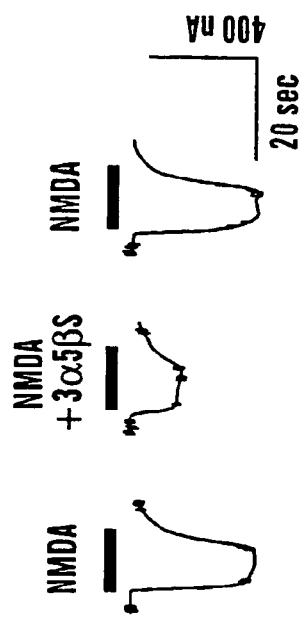
FIG. 29 contains graphical representations of data indicating the choice of NR2 subunit influences 3α5βS inhibition of the NMDA response. A–D are examples of traces obtained from *oocytes* previously injected with NR1/NR2A, NR1/NR2B, NR1/NR2C, or NR1/NR2D mRNAs, respectively. The bar indicates the period of drug application. Interval between consecutive current traces was 45 s. The receptors were activated by co-application of 10 μM glycine plus 80 μM NMDA (NR1/NR2A, A), 25 μM NMDA (NR1/NR2B, B and NR1/NR2C, C), or 10 μM NMDA (NR1/NR2D, D). E is concentration-response curves for 3α5βS effect on NR1/NR2 receptors. Data points are averaged values of normalized steady-state current responses from *oocytes* injected with NR1/NR2A (1, n=4), NR1/NR2B (○, n=3), NR1/NR2C (■, n=6) or NR1/NR2D (□, n=4) RNAs. Current responses are expressed relativeto the current response in the absence of PS. Error bars represent SEM. F is a graph of data indicating dependence of 3α5βS effect on membrane potential. Points are averaged relative current obtained in the presence of 100 μM 3α5βS (1, NR1/NR2A, n=5; ○, NR1/NR2B, n=10) or 10 μM 3α5βS (■, NR1/NR2C, n=4; □, NR1/NR2D, n=10). G is a concentration response curve showing the effect of 3α5βS on glutamate. Data points are averaged normalized peak current responses to glutamate from *oocytes* injected with NR1/NR2A subunits obtained in the presence of 10 μM glycine and in the absence (1, n=4) or presence (○, n=3) of 100 μM 3α5βS. The data for each *oocyte* were normalized to standard current responses induced by co-application of 200 μM NMDA and 10 μM glycine. Concentration response data for glutamate alone is the same as in FIG. 27, and is repeated for comparison. H indicates the effect of 3α5βS on glycine concentration-response curve. Data points are averaged normalized peak current responses to glycine from *oocytes* injected with NR1/NR2A subunits obtained in the presence of 10 μM glutamate and in the absence (s) or presence (Δ) of 100 μM 3α5βS. The data for each *oocyte* were normalized to standard current responses induced by co-application of 200 μM NMDA and 10 μM glycine. Concentration response data for glycine alone is the same as in FIG. 28, and is repeated for comparison.
Figure 29D:
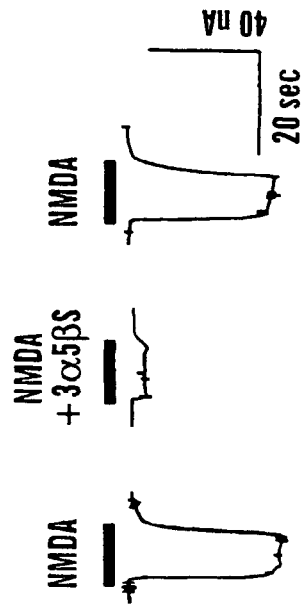
Figure 29A:
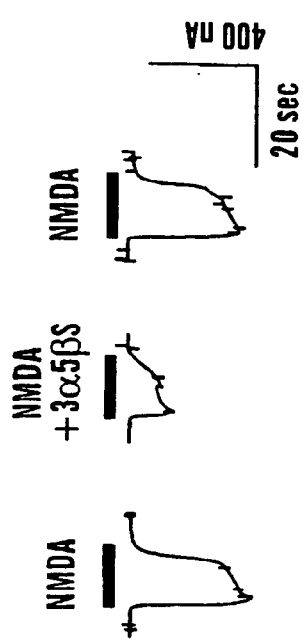
Figure 29C:
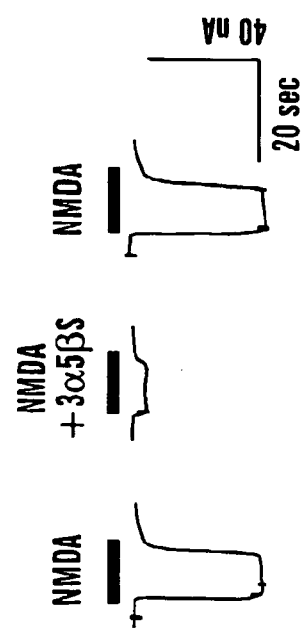
Figure 29F:
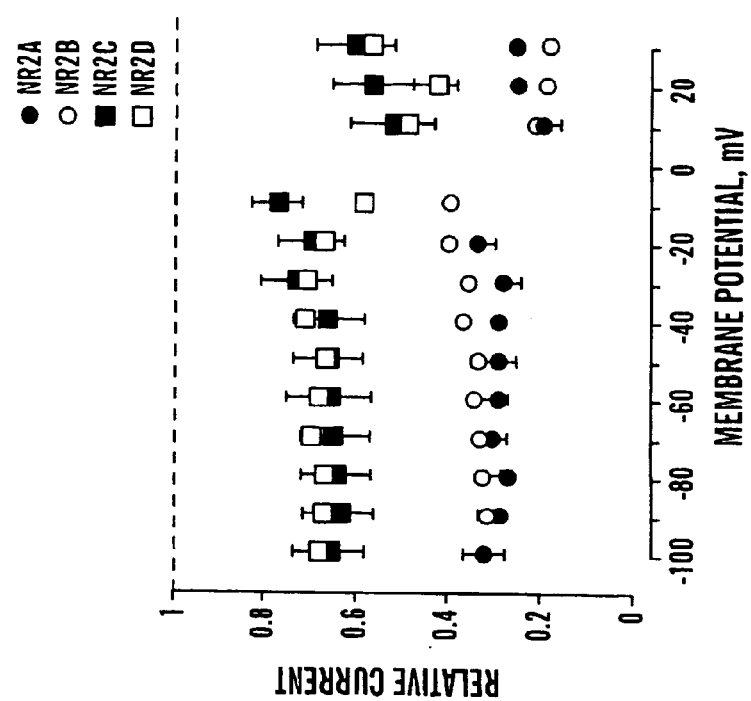
Figure 29E:
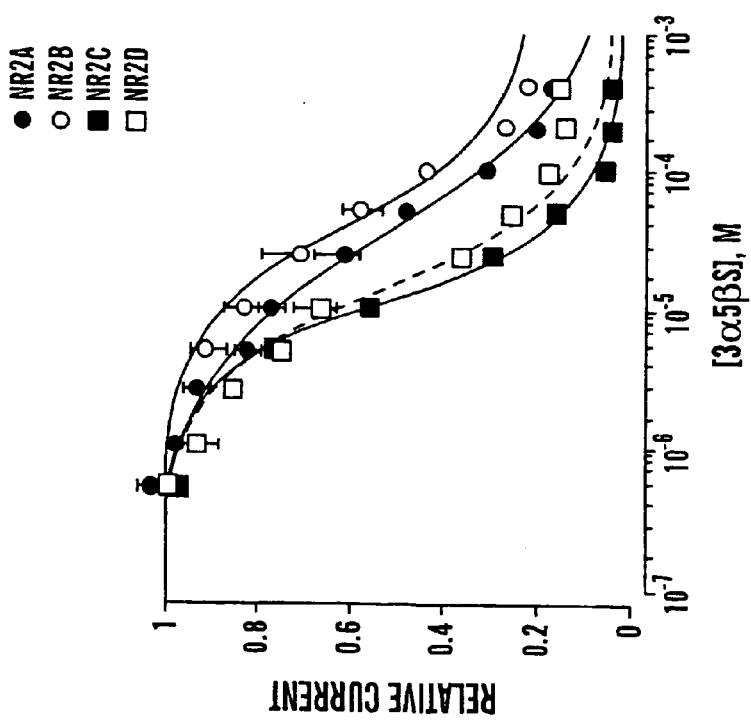
Figure 29H:
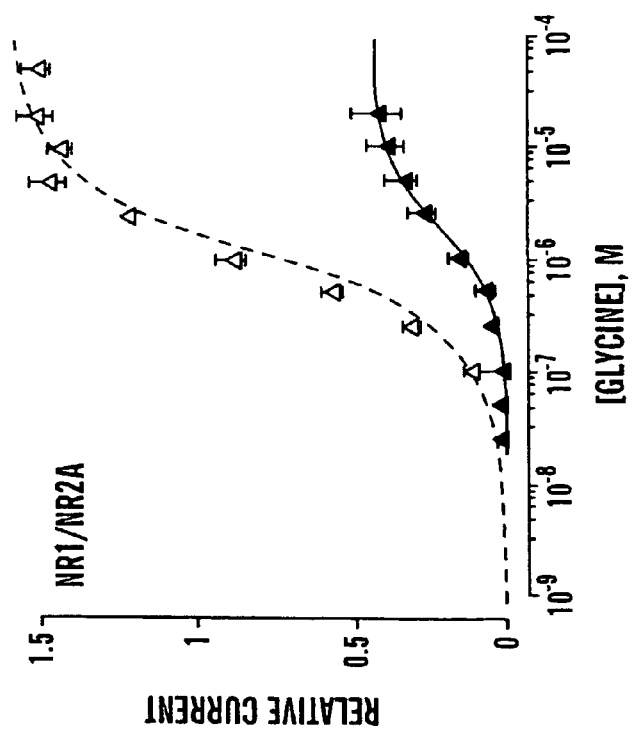
Figure 29G:
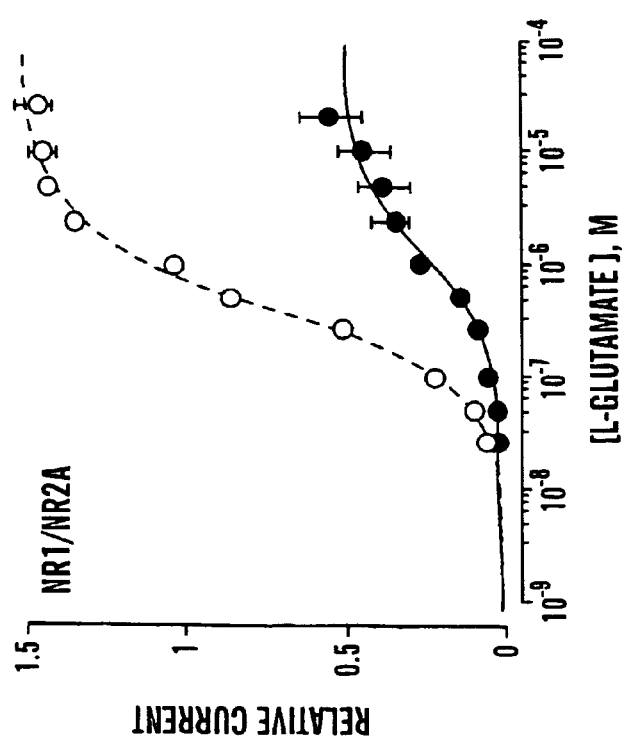
Figure 29J:
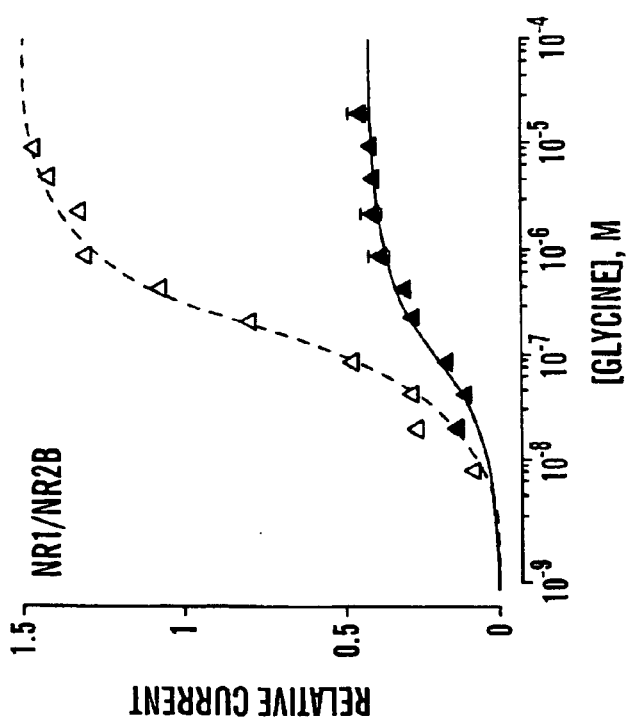
Figure 29I:
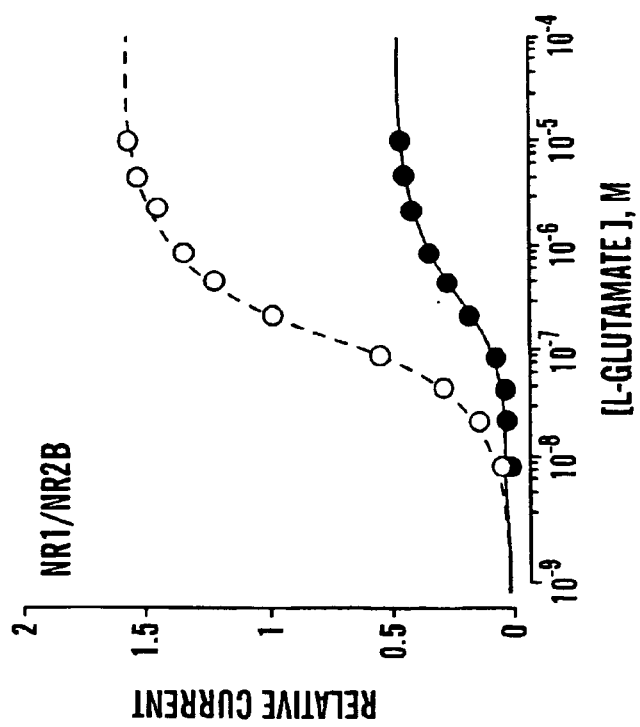
Figure 29K:
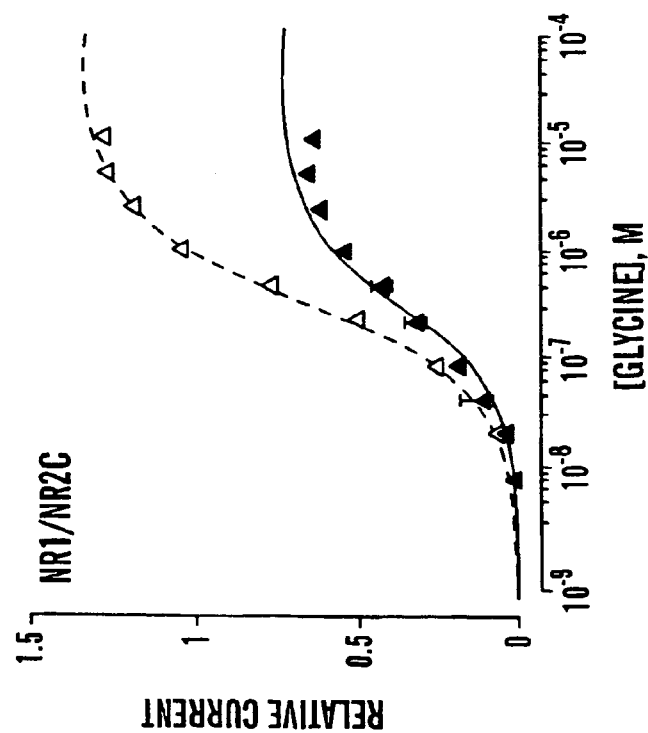
Figure 29L:
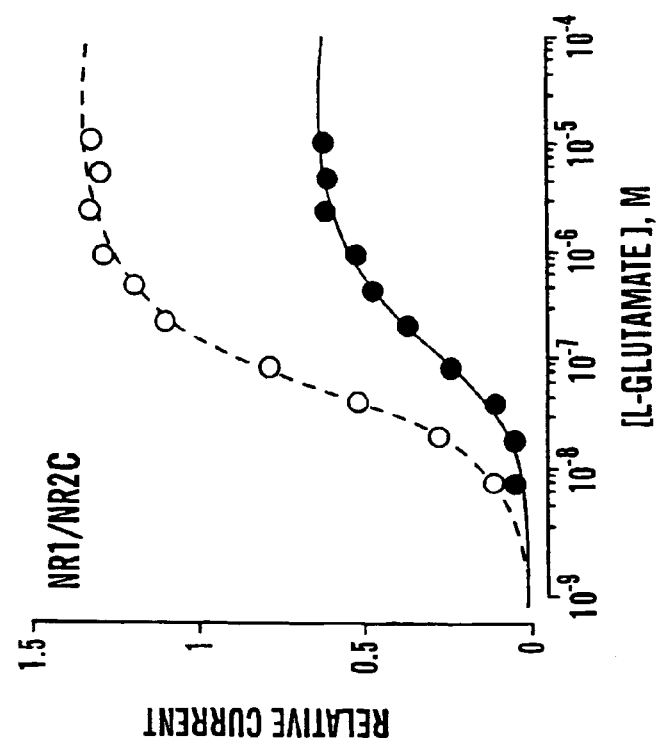
Figure 29N:
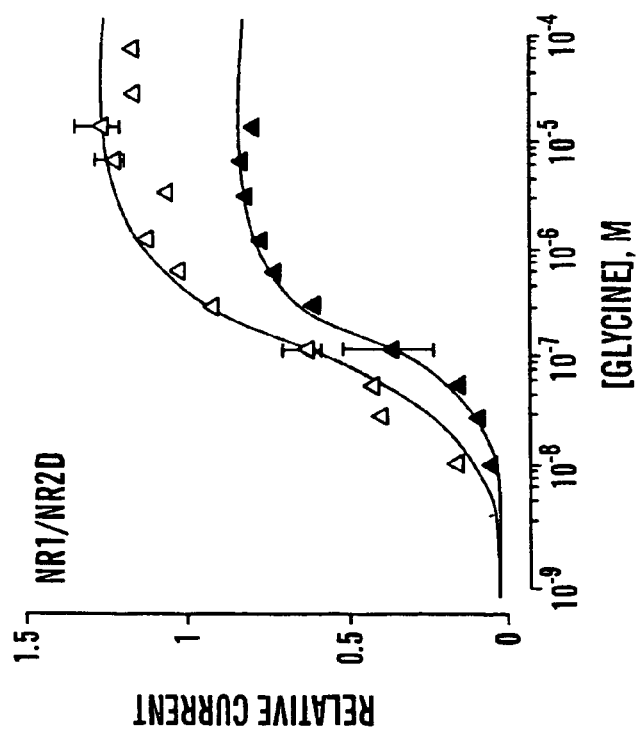
Figure 29M:
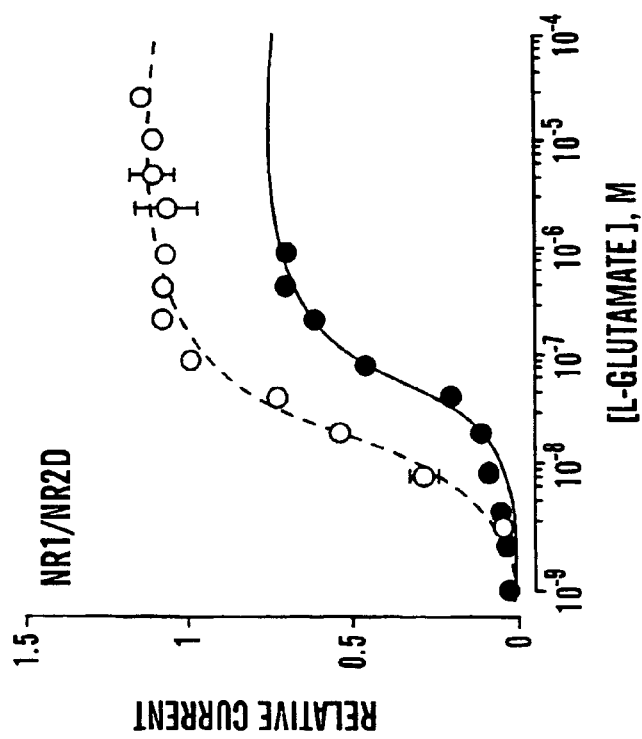

The inhibitory effect of PS on NR1/NR2C and NR1/NR2D was a consequence of a decrease in the efficacies of glutamate, NMDA (FIG. 27C–D), and glycine (FIG. 28C–D). Agonist potency was not decreased, and in fact appeared to be somewhat increased, with the result that percentage inhibition by PS tended to be greater at high than at low agonist concentrations (Table 4C and 4D). Thus, PS did not compete for either the glutamate or glycine recognition site.

Inhibitory Potency of 3α5⊕S Depends Upon the NR2 Subunit

As shown in FIG. 29A–D, 100 μM 3α5βS reversibly inhibited NMDA-induced currents of Xenopus oocytes expressing NR1/NR2A (FIG. 28A), NR1/NR2B (FIG. 28B), NR1/NR2C (FIG. 28C), or NR1/NR2D (FIG. 28D) receptors. However, the extent of inhibition was significantly greater with NR1/NR2C and NR1/NR2D receptors than with NR1/NR2A and NR1/NR2B receptors. Concentration-response analysis (FIG. 28E, Table 5) indicated that this difference was primarily due to an approximately 4-fold lower potency of 3α5βS at NR1/NR2A and NR1/NR2B receptors than at NR1/NR2C and NR1/NR2D receptors (see Table 5 for $EC_{50}$). Inhibition of the NMDA induced current by 3α5βS exhibited little if any voltage dependence from −100 to +20 mV (FIG. 28F).

TABLE 5

Concentration dependence of 3α5βS modulation of the NMDA plus glycine response. Results from each oocyte (number given in far right column) were independently fitted to the logistic equation. $E_{max}$ is expressed as percentage change (inhibition) relative to the response induced in the same oocyte by an approximate $EC_{50}$ concentration of NMDA in the presence of 10 μM glycine. Concentration of NMDA was 80, 25, 25, and 10 μM for NR1/NR2A, NR1/NR2B, NR1/NR2C, and NR1/NR2D, respectively (see Methods).

| Subunits | 3α5βS $E_{max}$ (% Change) | 3α5βS $EC_{50}$ | log 3α5βS $EC_{50}$ | $n_H$ | (#) |
|---|---|---|---|---|---|
| NR1/NR2A | −81 ± 5% | 62 μM | −4.20 ± 0.06 | 1.39 ± 0.07 | (3) |
| NR1/NR2B | −82 ± 1% | 38 μM | −4.42 ± 0.11 | 1.06 ± 0.04 | (3) |
| NR1/NR2C | −99 ± 2% | 12 μM | −4.93 ± 0.03 | 1.34 ± 0.04 | (6) |
| NR1/NR2D | −98 ± 7% | 14 μM | −4.85 ± 0.03 | 1.14 ± 0.16 | (4) |

To determine how 3α5βS inhibits the glutamate response, concentration-response curves were constructed for glutamate (in the presence of 10 μM glycine) and glycine (in the presence 10 μM glutamate) in the presence and absence of 100 μM 3α5βS. As shown in FIG. 29, 3α5βS decreased the efficacy with which glutamate and glycine activate NR1/NR2A (FIG. 29G–H), NR1/NR2B (FIG. 29I–J), NR1/NR2C (FIG. 29K–L), and NR1/NR2D (FIG. 29M–N) receptors.

Methods of the Invention

Preparation of RNA

Plasmids containing the $NR1_{100}$ (NR1G) and NR2A cDNA inserts were kindly provided by Dr. Nakanishi (Kyoto University Faculty of Medicine, Kyoto, Japan). Plasmids containing the NR2B, NR2C and NR2D cDNA inserts were kindly provided by Dr. P. Seeburg (Heidelberg University, Heidelberg, Germany). Plasmids were linearized with appropriate restriction enzyme prior to in vitro transcription using the Message Machine kit (Ambion, Inc., Austin, Tex.).

NMDA Receptor Expression in Xenopus oocytes

Female, oocyte-positive Xenopus laevis frogs were purchased from Xenopus I (Dexter, Mich.). Following 45 min of 0.15% Tricaine anesthesia, ovarian sections containing the follicular oocytes were removed from the frog through a lateral abdominal incision and were immediately placed in a calcium-free solution (NaCl 96 mM, $MgCl_2$ 1 mM, KCl 2 mM, Hepes 50 mM, pyruvate 2.5 mM, 0.1.mg/ml gentamycin, pH 7.4). Following 1.5.–2 hours incubation in 0.2% collagenase (type II, Sigma Chemical Co., St. Louis, Mo.) at room temperature, individual defolliculated Dumont stage V and VI oocytes were transferred to an incubator and maintained overnight in Barth's solution (NaCl 84 mM, $NaHCO_3$ 2.4 mM, $MgSO_4$ 0.82 mM, KCl 1 mM, $Ca(NO_3)_2$ 0.33 mM, $CaCl_2$ 0.41 mM, Tris/HCl 7.5 mM, pyruvate 2.5 mM, 0.1 mg/ml gentamycin, pH 7.4) at 18–20° C. Oocytes were injected with 50 nL of RNA solutions using an electronic microinjector (Drummond Inc., Broomall, Pa.). The transcripts were injected at a ratio of 0.125/1.25 ng mRNA per oocyte for NR1/NR2A receptors and 0.5/5 ng mRNA per oocyte for NR1/NR2B, NR1/NR2C, and NR1/NR2D receptors. The injected oocytes were used for experiments following 1–5 days of incubation in Barth's solution at 18–20° C.

Electrophysiology

Measurements of ion currents from oocytes expressing NMDA receptors were performed using an Axoclamp-2A voltage clamp amplifier (Axon Instruments, Inc., Foster City, Calif.) in two-electrode voltage clamp mode. The microelectrodes were fabricated from borosilicate glass capillaries with a programmed puller (Sutter Instrument Co., Calif.). Microelectrode resistance was 1–3 MΩ_when filled with 3 M KCl. The oocyte recording chamber was continuously perfused with $Mg^{2+}$-free Ba-Ringer solution (NaCl 96 mM, KCl 2 mM, $BaCl_2$ 1.8 mM, Hepes 5 mM). Ba-Ringer was used to prevent NMDA receptor currents from being complicated by activation of $Ca^{2+}$ dependent $Cl^-$ channels (Leonard and Kelso, Neuron. 4: 53–60 (1990)). Potentiation of the NMDA-induced current of $NR1_{100}$/NR2A receptors by PS in Ba-Ringer tended to be less than previously observed with using $Ca^{2+}$-containing solution (Yaghoubi et al., *Brain Res.* 803: 153–160 (1998)), possibly reflecting a nonlinear contribution of $Ca^{2+}$ dependent $Cl^-$ channels to the NMDA induced current.

Except where otherwise stated, *oocytes* were clamped at a holding potential of −70 mV during data acquisition. The membrane current was filtered at 500 Hz and sampled at 100 Hz. Drugs were applied using a gravity-driven external perfusion system. The working volume of the recording chamber was 30 µl and the rate of the perfusion was 50 µl/sec. The drug application lasted 10 sec and was followed by 60 s wash. Data acquisition and external perfusion were controlled using custom-written software implemented in the SuperScope II development environment (GW Instruments, Mass.). All experiments were performed at room temperature of 22–24° C. Peak or steady-state current measurements were normalized and expressed as a fraction of the peak or steady-state control current measurements, which were performed before and after application of every single concentration of agonists or steroids.

Data Analysis

Concentration-response data were analyzed by nonlinear regress ion using the logistic equation Response=$E_{max}/(1+(EC_{50}/c)^{n_H})$, where c is concentration, $E_{max}$ is the maximum response, $n_H$ is the Hill coefficient. The data are presented as mean±SEM. $EC_{50}$ values are averaged as logarithms (De Lean et al., *Am. J. Physiol.* 235: E97–E102 (1978))±the SEM of the log $EC_{50}$. Hence, the reported mean $EC_{50}$ values are geometric means. PS-induced changes in $E_{max}$ and $EC_{50}$ for NMDA, glutamate, and glycine were tested for statistical significance by two methods: 1) Concentration-response data from each *oocyte* were fitted to the logistic equation, and parameter estimates for $E_{max}$ and $EC_{50}$ in the presence and absence of PS were compared by unpaired, 2-tailed t-test. 2) The normalized (to the 200 µM NMDA response) responses at each concentration from multiple *oocytes* were averaged to construct pooled concentration-response curves (points in FIG. 27) in the presence and absence of PS. The pooled data were simultaneously fitted to the logistic equation, either with $E_{max}$ and $EC_{50}$ constrained to be identical in the presence and absence of PS, or allowing one or both to vary independently. The improvement in the sum-of-squares due to the introduction of additional free parameters was tested for significance by the "extra sum-of-squares" method (Munson and Rodbard, *Anal. Biochem.* 107: 220–239 (1980)). In one case, allowing either $E_{max}$ or $EC_{50}$ to vary independently produced a significant improvement in the fit, but allowing both parameters to vary did not produce a significant further improvement. This was regarded as indicating a significant treatment effect of PS, but the change in $EC_{50}$ and $E_{max}$ was not considered significant. The PS-induced change in $EC_{50}$ or $E_{max}$ was considered significant only if it met the p<0.05 criterion by both tests. No attempt was made to test the generally small changes in $n_H$ for statistical significance.

Chemicals

Steroids were obtained from Steraloids, Inc. (Wilton, N.H.). Other compounds were obtained from Sigma (St. Louis, Mo.). Steroid stocks were prepared in DMSO and diluted into recording medium (final DMSO concentration 0.5%). Other solutions also contained 0.5% DMSO.

EXAMPLE 7

Differential Effects of PS on NMDA Receptors

Pregnenolone Sulfate (PS), an endogenous neurosteroid, differentially modulates different subtypes of the NMDA receptor. PS potentiates heteromeric NR1/NR2A and NR1/NR2B, while inhibits NR1/NR2C and NR1/NR2D containing receptors. Following 1–5 days after mRNA injection, a 10 sec application of a specific agonist of the NMDA receptor, 80 µM NMDA, plus the co-agonist, 10 µM glycine, gave rise to inward currents in voltage-clamped *oocytes* that expressed NMDA receptors consisting of NR1/NR2A receptor subunits. Co-application of 100 µM PS resulted in 59±4% (n=33) potentiation of the NMDA responsive membrane current. The observed effect of PS was reversible, as washout of PS for 60 sec led to complete recoveryof the initial response. Similar to the effect on the NR1/NR2A receptor, co-application of 100 µM PS to *oocytes* expressing NR1/NR2B receptors resulted in reversible potentiation (95±6%, (n=20)) of the membrane current induced by a 10 sec application of 25 µM NMDA and 10 µM glycine. However, in contrast to the potentiating effect of PS on NR1/NR2A and NR1/NR2B receptors, co-application of 100 µM PS to voltage-clamped *oocytes* injected with NR1/NR2C or NR1/NR2D mRNAs resulted in reversible inhibition (32±3%, n=11 and 29±2%, n=16 respectively) of NMDA-induced membrane currents after a 10 sec application of 10 µM glycine and 25 µM NMDA for NR1/NR2C or 10 µM glycine and 10 µM NMDA for NR1/NR2D receptors.

Figure 30:
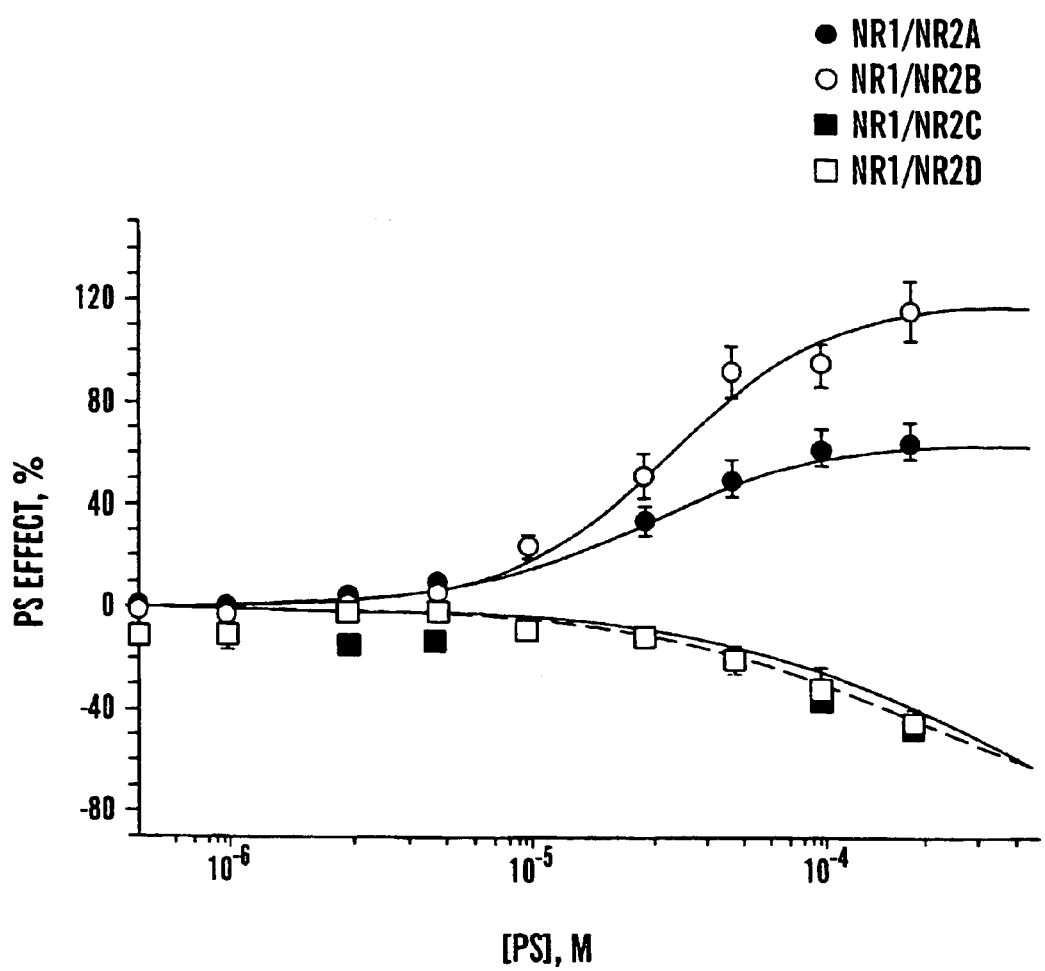
FIG. 30 is a graphical representation of data in the form of dose-response curves for Pregnenolone Sulfate (PS) effect on NR1/NR2 receptors. Data points are averaged values of percent changes in peak current response in presence of increasing concentrations of PS, from *oocytes* injected with NR1/NR2A (n=8), NR1/NR2B (n=8), NR1/NR2C (n=4) or NR1/NR2D (n=4) mRNAs. Current response were normalized relative to control response obtained by application of 10 μM glycine and 80 μM NMDA (NR2A), 25 μM NMDA (NR2B, NR2C) or 10 μM NMDA (NR2D). Error bars are standard errors of the means. Lines were drawn using equation $1+E_{max}/(1+EC_{50}/[agonst])^h)$. $E_{max}$, $EC_{50}$ and h were obtained by averaging maximum responses, EC50 and Hill coefficients of individual experimental dose-response relationships.

Different concentrations of PS in the range from 0.5 to 200 µM were co-applied with 10 µM glycine and 10, 25 or 80 µM NMDA to *oocytes* injected with NR1/NR2D, NR1/NR2B (or NR1/NR2C) or NR1/NR2A respectively to study the relationship of PS concentration to potentiation of the NMDA response. The concentration of NMDA chosen to activate the receptor was close to the $EC_{50}$ for NMDA obtained in the absence of steroids. The PS effect on the NMDA receptors was concentration dependent (FIG. 30) with maximum potentiation of 67±7% (n=8) and 119±9% (n=8) for NR1/NR2A and NR1/NR2B respectively and maximum inhibition of 63±9% (n=4) and 70±6% (n=4) for NR1/NR2C and NR1/NR2D respectively.

Identification of a Region on the NR2 Subunit Conferring Modulation by PS

Figure 31:
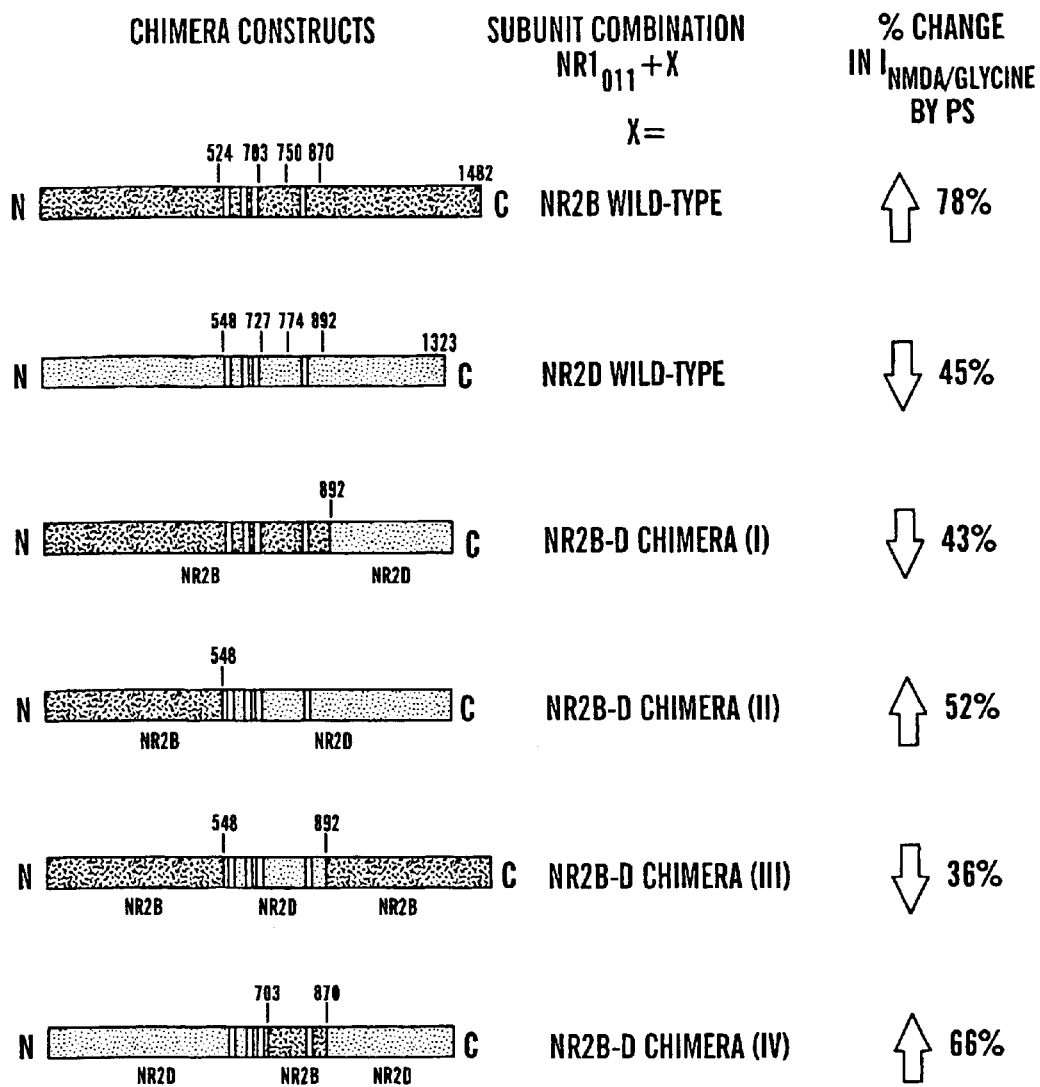
FIG. 31 contains schematic representations of wild-type NMDAR NR2B, NR2D subunits, and the NR2 chimera constructs. Fragments from NR2B are in black and fragments from NR2D are in grey. Vertical bars correspond to the three transmembrane domains and the re-entrance domain. The numbers are the positions of the ligation junctions.
Figure 32:
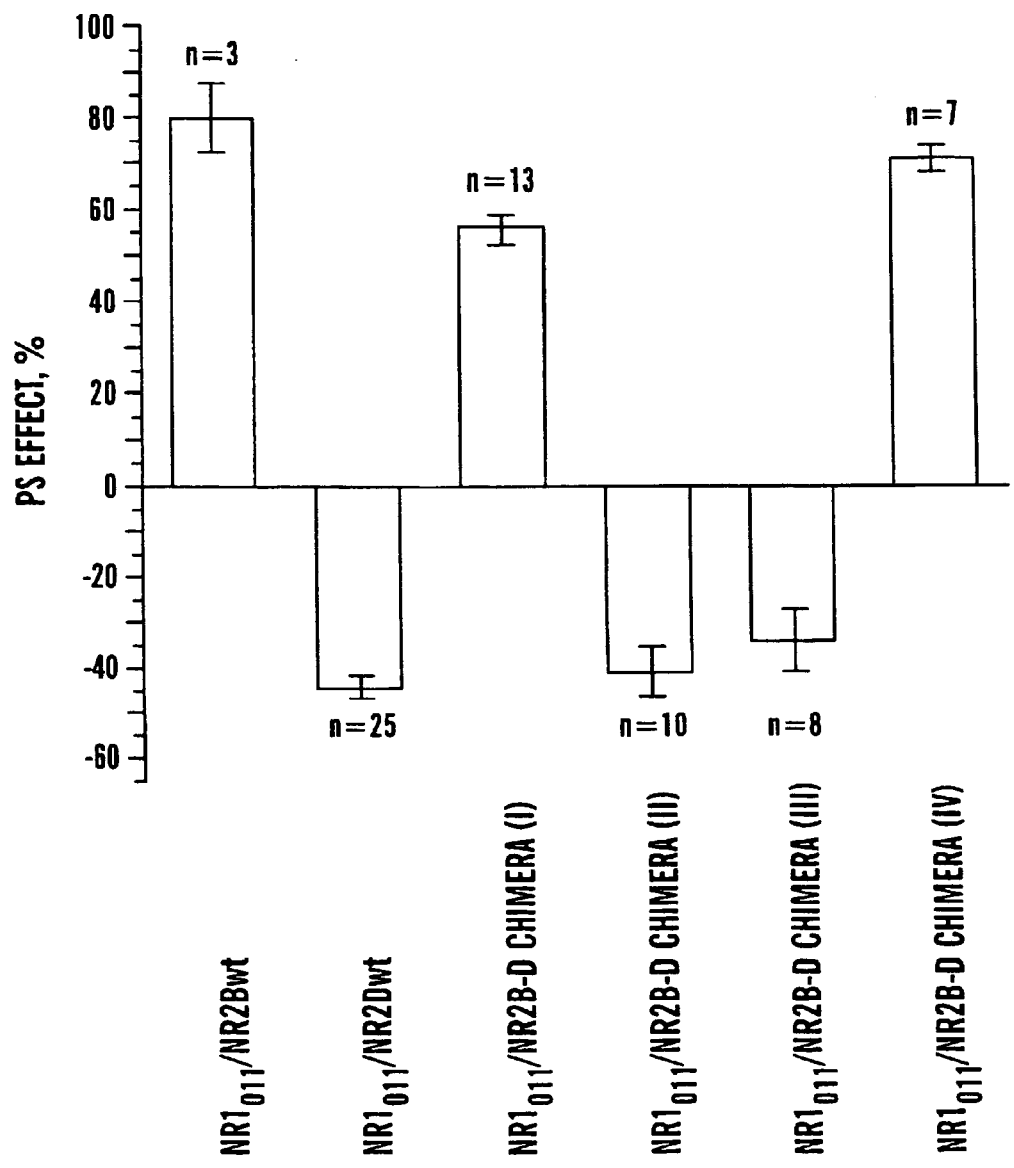
FIG. 32 is a bar graph of data indicating 100 μM Pregnenolone Sulfate modulates the inward currents elicited by 300 μM NMDA and 50 μM Glycine from *Xenopus oocytes* expressing recombinant heteromeric $NR1_{011}$/NR2 NMDA receptors. PS potentiates $NR1_{011}$/NR2Bwt by 78.36±7.89% (mean±SEM), $NR1_{011}$/NR2B-D Chimera(I) by 52.69±3.58%, NR1011/NR2B-D chimera(IV) by 66.05±2.76%; inhibits $NR1_{011}$/NR2Dwt by 45.18±2.62%, $NR_{011}$/NR2B-D Chimera(II) by 43.04±5.44%, and $NR1_{011}$/NR2B-D Chimera (III) by 36.74±6.54%. The error bar shows standard error. n is the number of *oocytes* recorded. The currents were recorded at −70 mV, in $Ba^{2+}$-Ringer's solution (in mM): 96 NaCl, 2 KCl, 1.8 $BaCl_2$, 5 HEPES, pH=7.5.

To identify domains on the NMDA receptor responsible for the differential modulatory effects bf PS, four chimeric NR2 subunits were constructed (FIG. 31). To produce the first subunit, 96% of the cytoplasmic COOH-terminal region of the NR2B subunit (residues 870 to 1482) were replaced with the corresponding region of the NR2D subunit (residues 892 to 1323). Like the wild-type, NR1a/NR2B (NR1a is also referred to as $NR1_{011}$) PS potentiated the NMDA-induced response of receptors containing NR1a/NR2 Chimera (I) subunits. 100 uM PS increased NR1a/NR2 Chimera(I) responses by 52.69±3.58% in the presence of saturating concentrations of NMDA and Glycine, 300 uM and 50 uM, respectively (FIG. 32). In contrast, when residues 524 to 1482 of the NR2B were replaced with those of NR2D, PS inhibited rather than potentiated the NMDA response. 100 uM PS inhibited the NR1a/NR2 Chimera(II) by 43.04±5.44%, similar to the wild-type NR1a/NR2D (45.18±2.62%) (FIG. 32). These results suggest that the region between residue 524 and 870 on NR2B and residues 548 to 892 on NR2D are sufficient to endow the modulatory effects of PS on the NMDA response that is characteristic to their specific subunits. To confirm this finding, a third chimera was constructed, NR2Chimera(III), in which the identified region on NR2B was replaced by the one on NR2D. Consistent with the hypothesis, PS inhibited the NMDA-induced currents from the expressed NR1a/NR2 Chimera (III) receptors (100 uM PS, 36.74±6.54%) (FIG. 32). Therefore, the region, reisdues 548 to 892, on the NR2D receptor is necessary and sufficient for the PS inhibitory effect.

In the fourth chimera receptor, NR2B-DChimera (IV), the residues 727 to 892 were replaced on NR2D with residues 703 to 870 of NR2B, which contains the second extracellular domain, the fourth hydrophobic transmembrane domain and 31 residues from the C-terminal intracellular tail. 100 μM PS potentiated the NR1011/NR2B-DChimera(IV) by 66.05±2.75%. This demonstrates that the region of residues 703 to 870 on NR2B is necessary and sufficient for the PS potentiating effect.

The above results indicate that the determinant of the modulatory effect of Pregnenolone Sulfate resides in the region between residues 703 and 870 on the NR2B subunit and residues 548 and 892 on the NR2D subunit. These findings lay the foundation for further identification of the important amino acid residues underlying the PS modulatory effect and definition of a novel modulatory site on the NR2 subunits of the NMDA receptor. Identification of these sites will lead to the development of pharmacological reagents to regulate NMDA receptor function in neurological and psychiatric diseases.

Methods of the Invention

Mutagenesis

The chimeric receptors were generated by first introducing a series of silent restriction sites in both the NR2B and NR2D cDNA. The chimeric cDNAs were then constructed by replacing corresponding regions of one cDNA with that of the other. The silence site mutations were generated by a method involving PCR. In brief, oligonucleotides were synthesized containing the mutation, and these oligonucleotides were used in combination with other oligonucleotides in PCR amplifications of fragments of the cDNA. The products of the PCR reactions were cut with two different restriction enzymes to generate A cassette containing the mutation. This cassette was then ligated into the cDNA cut with the same two restriction enzymes. For all of the mutations, single isolates were selected, and the entire region of the amplified cassette was sequenced to check for the mutation and insure against second-site mutations.

Preparation of RNA

Same as in Example 5.

Expression in *Xenopus oocytes*

Same as in Example 5.

Electrophysiology

Same as in Example 5.

Chemicals

Same as in Example 5.

What is claimed is:

1. A method for identifying a subunit specific modulator of the N-methyl-D-aspartate (NMDA) receptor, comprising:

a) providing a plurality of recombinant NMDA receptors which differ in their subunit identity, wherein the plurality of NMDA receptors have identical NR2 subunits and differ in NR1 subunits, and wherein at least one NR1 subunit is an isoforrn with amino acid substitution mutations that correspond to mutations R182A, K193A, K202A, R233A, and R252A of NR1011I;

b) contacting the NMDA receptors of step a) with a neurotransmitter recognition site ligand in the presence and absence of a candidate modulator, wherein the candidate modulator is a steroid-based molecule; and c) assaying for receptor activity following step b), wherein an increase or decrease in activity in at least one, but not all members of the plurality of NMDA receptors, in the presence but not the absence of a candidate modulator, is an indication that the candidate modulator is a subunit specific modulator.

2. The method of claim 1 further comprising comparing the subunit identity of the at least one NMDA receptor whose activity is increased or decreased to the members of the plurality of NMDA receptors whose activity is not increased or decreased to determine the subunit specificity ofn the candidate modulator.

3. The method of claim 1, wherein the identical NR2 subunits are selected from the group consisting of NR2A, NR2B, NR2C, and NR2D.

4. The method of claim 1 wherein at least one of the NR1 subunits is a chimeric isoform.

5. The method of claim 1 wherein assaying step c) is with an *oocyte* expression system.

6. The method of claim 1 wherein the neurotrasmitter recongition site ligand is an agonist.

7. The method of claim 6 wherein the agonist is selected from the group consisting of NDMA, glutamate, and glycine.

8. The method of claim 1 wherein the neurotransmitter recognition site ligand is an antagonist.

9. The method of claim 1 wherein the candidate modulator is obtained from a library of small molecules.

10. The method of claim 1 wherein the candidate modulator is a known neuromodulator.

* * * * *

SEQUENCE LISTING

<160> NUMBER OF SEQ ID NOS: 6

<210> SEQ ID NO 1
<211> LENGTH: 101
<212> TYPE: PRT
<213> ORGANISM: Homo sapiens

<400> SEQUENCE: 1

```
Ile Leu Glu Ala Glu Leu Ala Val Glu Pro Lys Thr Glu Thr Tyr Val
  1               5                  10                  15

Glu Ala Asn Met Gly Leu Asn Pro Ser Pro Asn Asp Pro Val Thr
             20                  25                  30

Asn Ile Cys Gln Ala Ala Asp Lys Gln Leu Phe Thr Leu Val Glu Trp
         35                  40                  45

Ala Lys Arg Ile Pro His Phe Ser Glu Leu Pro Leu Asp Asp Gln Val
     50                  55                  60

Ile Leu Leu Arg Ala Gly Trp Asn Glu Leu Leu Ile Ala Ser Phe Ser
 65                  70                  75                  80

His Arg Ser Ile Ala Val Lys Asp Gly Ile Leu Leu Ala Thr Gly Leu
                 85                  90                  95

His Val His Arg Asn
            100
```

<210> SEQ ID NO 2
<211> LENGTH: 93
<212> TYPE: PRT
<213> ORGANISM: Homo sapiens

<400> SEQUENCE: 2

```
Leu Cys Gln Leu Gly Lys Tyr Thr Thr Asn Ser Ser Ala Asp His Arg
  1               5                  10                  15

Val Gln Leu Asp Leu Gly Leu Trp Asp Lys Phe Ser Glu Leu Ala Thr
             20                  25                  30

Lys Cys Ile Ile Lys Ile Val Glu Phe Ala Lys Arg Leu Pro Gly Phe
```

-continued

```
                35                  40                  45
Thr Gly Leu Ser Ile Ala Asp Gln Ile Thr Leu Leu Lys Ala Ala Cys
            50                  55                  60

Leu Asp Ile Leu Met Leu Arg Ile Cys Thr Arg Tyr Thr Pro Glu Gln
 65                  70                  75                  80

Asp Thr Met Thr Phe Ser Asp Gly Leu Thr Leu Asn Arg
                85                  90

<210> SEQ ID NO 3
<211> LENGTH: 98
<212> TYPE: PRT
<213> ORGANISM: Homo sapiens

<400> SEQUENCE: 3

Ile Asn Leu Leu Met Ser Ile Glu Pro Asp Val Ile Tyr Ala Gly His
  1               5                  10                  15

Asp Asn Thr Lys Pro Asp Thr Ser Ser Leu Leu Thr Ser Leu Asn
                20                  25                  30

Gln Leu Gly Glu Arg Gln Leu Leu Ser Val Val Lys Trp Ser Lys Ser
                35                  40                  45

Leu Pro Gly Phe Arg Asn Leu His Ile Asp Asp Gln Ile Thr Leu Ile
            50                  55                  60

Gln Tyr Ser Trp Met Ser Leu Met Val Phe Gly Leu Gly Trp Arg Ser
 65                  70                  75                  80

Tyr Lys His Val Ser Gly Gln Met Leu Tyr Phe Ala Pro Asp Leu Ile
                85                  90                  95

Leu Asn

<210> SEQ ID NO 4
<211> LENGTH: 98
<212> TYPE: PRT
<213> ORGANISM: Homo sapiens

<400> SEQUENCE: 4

Val Ser Leu Leu Glu Val Ile Glu Pro Glu Val Leu Tyr Ala Gly Tyr
  1               5                  10                  15

Asp Ser Ser Val Pro Asp Ser Thr Trp Arg Ile Met Thr Thr Leu Asn
                20                  25                  30

Met Leu Gly Gly Arg Gln Val Ile Ala Ala Val Lys Trp Ala Lys Ala
                35                  40                  45

Ile Pro Gly Phe Arg Asn Leu His Leu Asp Asp Gln Met Thr Leu Leu
            50                  55                  60

Gln Tyr Ser Trp Met Phe Leu Met Ala Phe Ala Leu Gly Trp Arg Ser
 65                  70                  75                  80

Tyr Arg Gln Ser Ser Ala Asn Leu Leu Cys Phe Ala Pro Asp Leu Ile
                85                  90                  95

Ile Asn

<210> SEQ ID NO 5
<211> LENGTH: 97
<212> TYPE: PRT
<213> ORGANISM: Homo sapiens

<400> SEQUENCE: 5

Ser Ala Leu Leu Asp Ala Glu Pro Pro Ile Leu Tyr Ser Glu Tyr Asp
  1               5                  10                  15

Pro Thr Arg Pro Phe Ser Glu Ala Ser Met Met Gly Leu Leu Thr Asn
```

-continued

```
                      20                  25                  30

Leu Ala Asp Arg Glu Leu Val His Met Ile Asn Trp Ala Lys Arg Val
            35                  40                  45

Pro Gly Phe Val Asp Leu Thr Leu His Asp Gln Val His Leu Leu Glu
            50                  55                  60

Cys Ala Trp Leu Glu Ile Leu Met Ile Gly Leu Val Trp Arg Ser Met
 65                  70                  75                  80

Glu His Pro Gly Lys Leu Leu Phe Ala Pro Asn Leu Leu Leu Asp Arg
            85                  90                  95

Asn

<210> SEQ ID NO 6
<211> LENGTH: 111
<212> TYPE: PRT
<213> ORGANISM: Homo sapiens

<400> SEQUENCE: 6

Ile Ile Leu Leu Val Ser Asp Asp His Glu Gly Arg Ala Ala Gln Lys
  1               5                  10                  15

Arg Leu Glu Thr Leu Leu Glu Glu Arg Glu Ser Lys Ala Glu Lys Val
            20                  25                  30

Leu Gln Phe Asp Pro Gly Thr Lys Asn Val Thr Ala Leu Leu Met Glu
            35                  40                  45

Ala Arg Glu Leu Glu Ala Arg Val Ile Ile Leu Ser Ala Ser Glu Asp
         50                  55                  60

Asp Ala Ala Thr Val Tyr Arg Ala Ala Ala Met Leu Asn Met Thr Gly
 65                  70                  75                  80

Ser Gly Tyr Val Trp Leu Val Gly Glu Arg Glu Ile Ser Gly Asn Ala
            85                  90                  95

Leu Arg Tyr Ala Pro Asp Gly Ile Ile Gly Leu Gln Leu Ile Asn
           100                 105                 110
```